(12) United States Patent
Alani et al.

(10) Patent No.: US 9,005,670 B2
(45) Date of Patent: Apr. 14, 2015

(54) USE OF HISTONE ACETYLTRANSFERASE INHIBITORS AS NOVEL ANTI-CANCER THERAPIES

(75) Inventors: Rhoda Myra Alani, Baltimore, MD (US); Philip A. Cole, Baltimore, MD (US); Gai Yan, Baltimore, MD (US); Erin M. Bowers, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 152 days.

(21) Appl. No.: 13/520,619

(22) PCT Filed: Jan. 5, 2011

(86) PCT No.: PCT/US2011/020271
§ 371 (c)(1),
(2), (4) Date: Feb. 8, 2013

(87) PCT Pub. No.: WO2011/085039
PCT Pub. Date: Jul. 14, 2011

(65) Prior Publication Data
US 2013/0142887 A1    Jun. 6, 2013

Related U.S. Application Data

(60) Provisional application No. 61/292,207, filed on Jan. 5, 2010.

(51) Int. Cl.
| | | |
|---|---|---|
| *A61K 31/4152* | (2006.01) | |
| *A61K 31/4188* | (2006.01) | |
| *A61K 33/24* | (2006.01) | |
| *C12Q 1/02* | (2006.01) | |
| *A61K 31/4155* | (2006.01) | |
| *A61K 31/4025* | (2006.01) | |
| *A61N 5/10* | (2006.01) | |
| *C07D 405/06* | (2006.01) | |

(52) U.S. Cl.
CPC ............ *C12Q 1/025* (2013.01); *A61K 31/4152* (2013.01); *A61K 31/4155* (2013.01); *A61K 31/4188* (2013.01); *A61K 33/24* (2013.01); *A61K 31/4025* (2013.01); *A61N 5/10* (2013.01); *C07D 405/06* (2013.01)

(58) Field of Classification Search
None
See application file for complete search history.

(56) References Cited

FOREIGN PATENT DOCUMENTS

| WO | 03074550 A2 | 9/2003 |
|---|---|---|
| WO | 2007059195 A1 | 5/2007 |
| WO | 2008157680 A2 | 12/2008 |

OTHER PUBLICATIONS

Belmar et al., J. Braz. Chem. 16, 179 (2005).
Dai et al., J. Med. Chem. 50, 1584 (2007).
Feng et al., Nat. Chem. Biol. 1, 146 (2005).
Fleckenstein and Plenio, J. Org. Chem. 73, 3236 (2008).
Guidez et al., Mol. Cell. Biol. 25, 5552 (2005).
Haval and Argade, J. Org. Chem. 73, 6963 (2008).
Holbert et al., J. Biol. Chem. 282, 36603 (2007).
Hosoya et al., Bioorg. Med. Chem. 11, 663 (2003).
Kim et al., Bull. Korean Chem. Soc. 12, 376 (1991).
Langner et al., Chem. Eur. J. 11, 6254 (2005).
Lau et al., J. Biol. Chem. 275, 1953 (2000).
Liu et al., J. Med. Chem. 51, 7843 (2008).
Liu et al., Nature 451, 846 (2008).
Liu et al., Nature 456, 269 (2008).
Manetti et al., Chem. Med. Chem. 1, 973 (2006).
Moreaus et al., Bioorg. Med. Chem. Lett. 18, 4022 (2008).
Organ et al., J. Comb. Chem. 5, 118 (2003).
Poux et al., Proc. Natl. Acad. Sci. USA 99, 14065 (2002).
Shaw et al., J. Am. Chem. Soc. 79, 3561 (1957).
Shia et al., J. Biol. Chem. 280, 11987 (2005).
Singh et al., European J. of Pharm. Sciences 25, 255 (2005).
Sutton et al., J. Biol. Chem. 278, 16887 (2003).
Szewczuk et al., J. Med. Chem. 50, 5330 (2007).
Tang et al., Nat. Struct. Mol. Biol. 15, 738 (2008).
Thompson et al., J. Biol. Chem. 276, 33721 (2001).
Thompson et al., Nat. Struct. Mol. Biol. 11, 308 (2004).
Totrov et al., Proceedings of the Third Annual International Conference on Computational Molecular Biology, 312 (1999).
Trujillo-Ferrara et al., Synthetic Communications 35, 2017 (2005).
Tutalkova et al., Collection of Czechoslovak Chemical Communications 41, 1377 (1976).
Uyanik et al., J. Am. Chem. Soc. 131, 251 (2009).
Vasyunkina et al., Russ. J. Org. Chem. 41, 742 (2005).
Watanabe et al., Redox Report 8, 151 (2003).
Yu et al., Biochemistry 245, 14788 (2006).
Zheng et al., J. Am. Chem. Soc. 127, 17182 (2005).
Bowers, E., et al., "Virtual ligand screening of the p300/CBP histone acetyltransferase: identification of a selective small molecule inhibitor", Chemistry and Biology, May 28, 2010, vol. 17, No. 5, pp. 471-482.
Dayam, R., et al., "Discovery of small molecule integrin avB3 antagonists as novel anticancer agents", Journal of Medicinal Chemistry, 2006, vol. 49, No. 15, pp. 4526-4534.

*Primary Examiner* — Kamal Saeed
(74) *Attorney, Agent, or Firm* — Johns Hopkins Technology Transfer

(57) ABSTRACT

The present invention provides methods for treating cancer comprising inhibiting the activity of p300/CBP histone acetyltransferase (HAT). Also provided are p300/CBP HAT inhibitors for treating a subject having cancer. In addition, the present invention includes biomarkers for p300/CBP HAT inhibition, which are used to i) monitor the effectiveness of cancer therapy, and ii) identify anti-cancer agents for use in combination therapy.

23 Claims, 37 Drawing Sheets

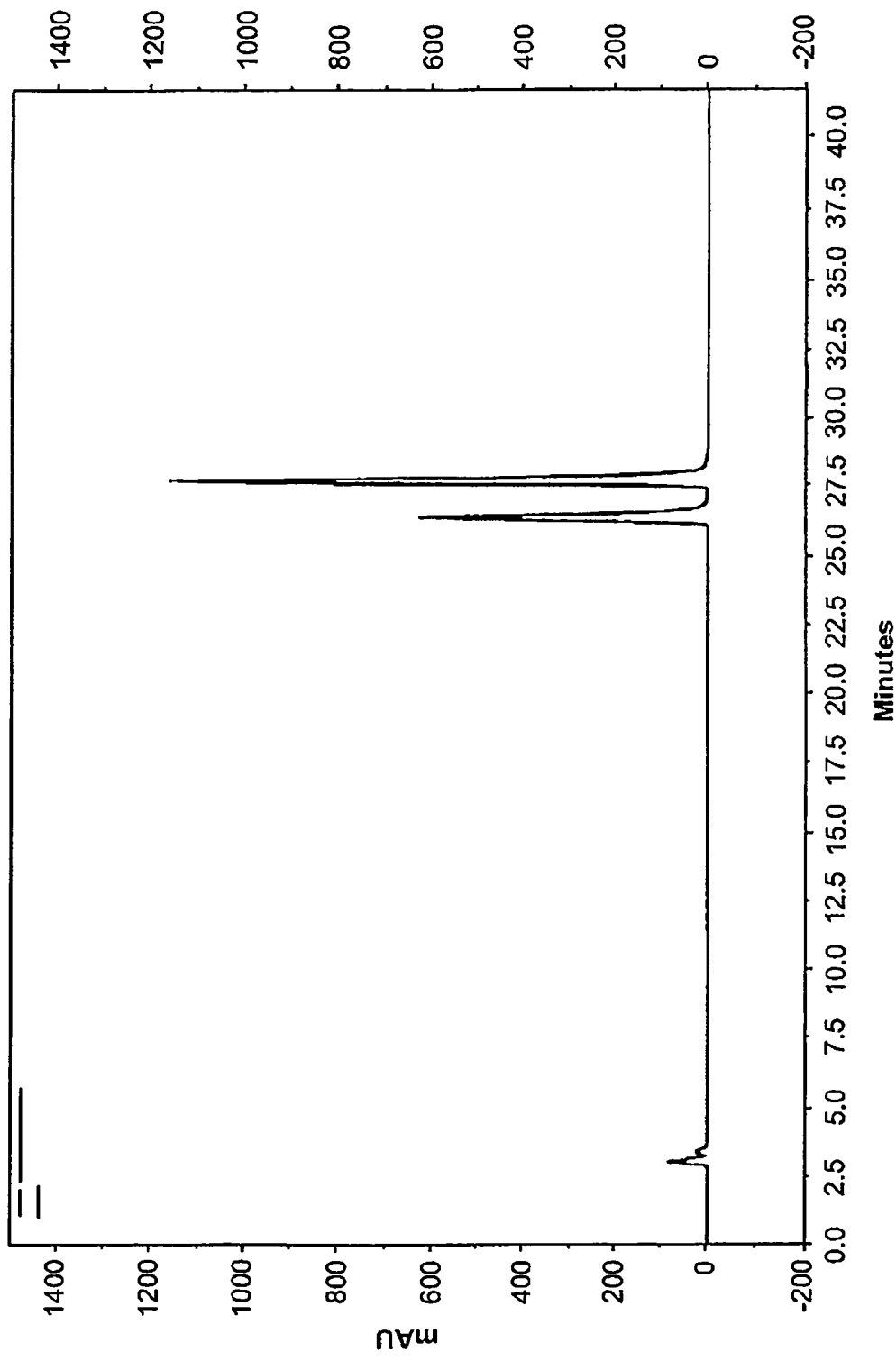

| Cpd. | R1 | R2 | R3 | R4 | R5 | IC$_{50}$ relative to C646 |
|---|---|---|---|---|---|---|
| C646 (6d) | CO$_2$H | H | NO$_2$ | Me | Me | 1 |
| 6f | SO$_3$H | H | NO$_2$ | Me | Me | 0.8 |
| 6e | H | CO$_2$H | NO$_2$ | Me | Me | 1 |
| 6m | CO$_2$H | H | CO$_2$Me | Me | Me | 1.3 |
| 6o | CO$_2$H | H | CN | Me | Me | 1.7 |
| 6a | CONH$_2$ | H | NO$_2$ | Me | Me | 1.8 |
| 6n | CO$_2$H | H | CO$_2$Et | Me | Me | 1.9 |
| C174 | CO$_2$H | H | NO$_2$ | H | Me | 2 |
| 6g | SO$_2$NH$_2$ | H | NO$_2$ | Me | Me | 2.1 |
| 6i | H | CO$_2$Me | NO$_2$ | Me | Me | 2.4 |
| 6b | CONH$_2$ | Cl | NO$_2$ | Me | Me | 2.6 |
| 6j | CONHMe | H | NO$_2$ | Me | Me | 3.5 |
| C730 | CO$_2$H | H | F | H | H | 6.5 |
| 6l | CO$_2$H | H | CH$_2$OH | Me | Me | 7.7 |
| 6h | CO$_2$Me | H | NO$_2$ | Me | Me | >15 |

FIG. 10A
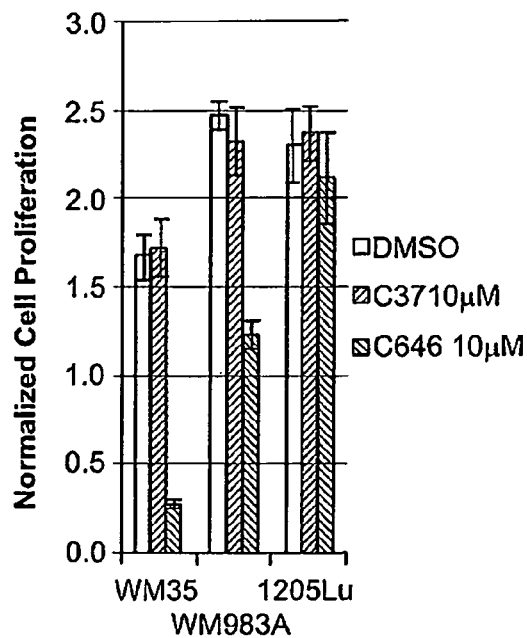
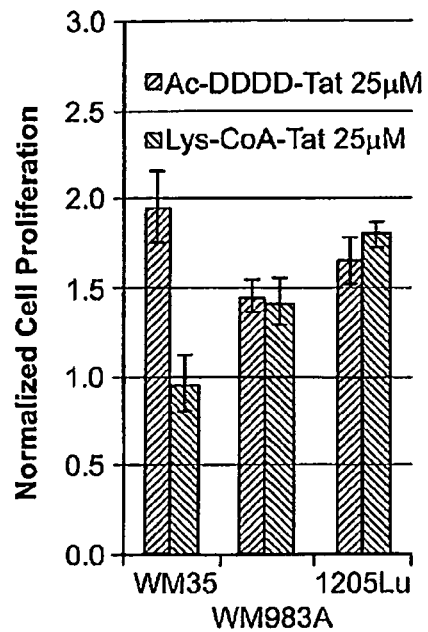
FIG. 10B
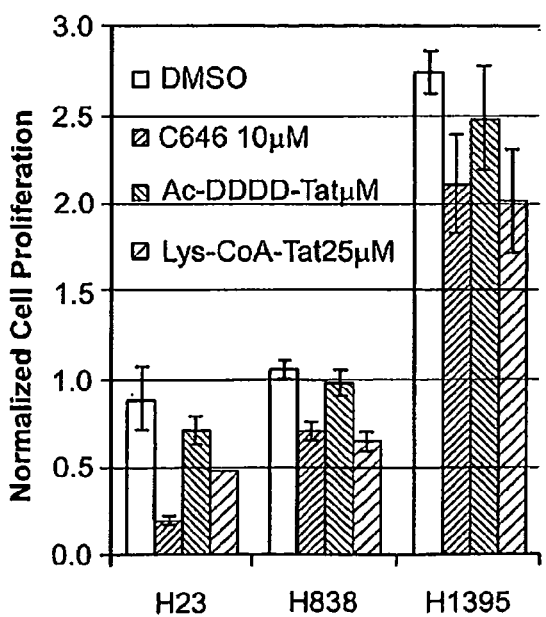
FIG. 10C
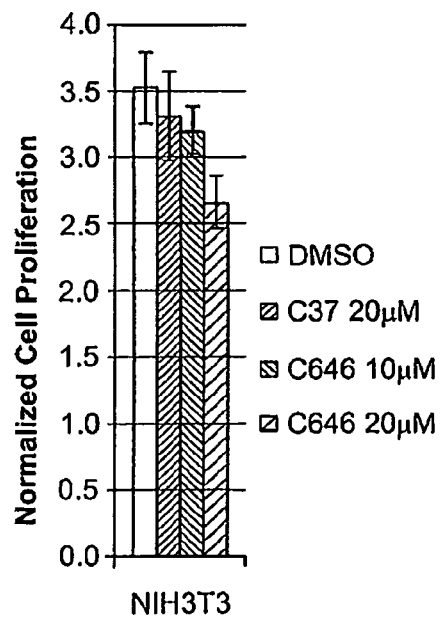

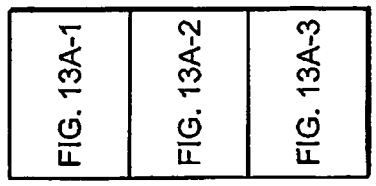
FIG. 13A
FIG. 13A-1
Developmental Therapeutics Program
One Dose Mean Graph
| Panel/Cell Line | Growth Percent | Mean Growth Percent – Growth Percent |
|---|---|---|
| Leukemia | | |
| CCRF-CEM | -5.17 | |
| ML-60(TB) | 5.53 | |
| K-562 | 13.64 | |
| MOLT 4 | 14.17 | |
| RPMI-8226 | -9.76 | |
| SR | 9.81 | |

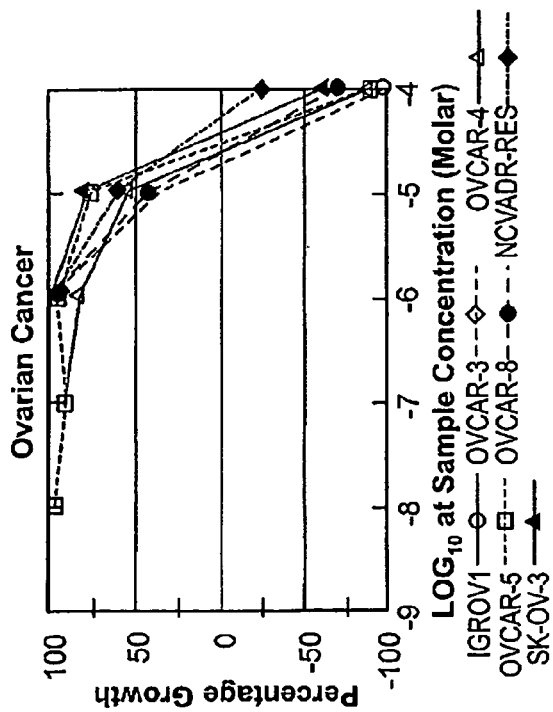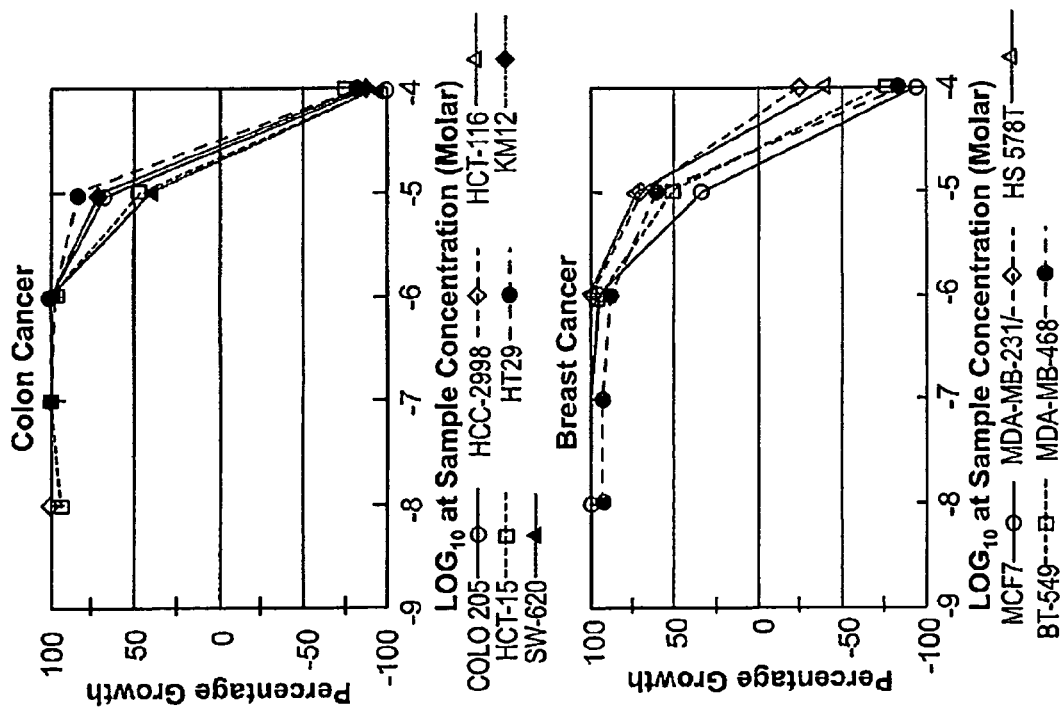
FIG. 13C

FIG. 14B
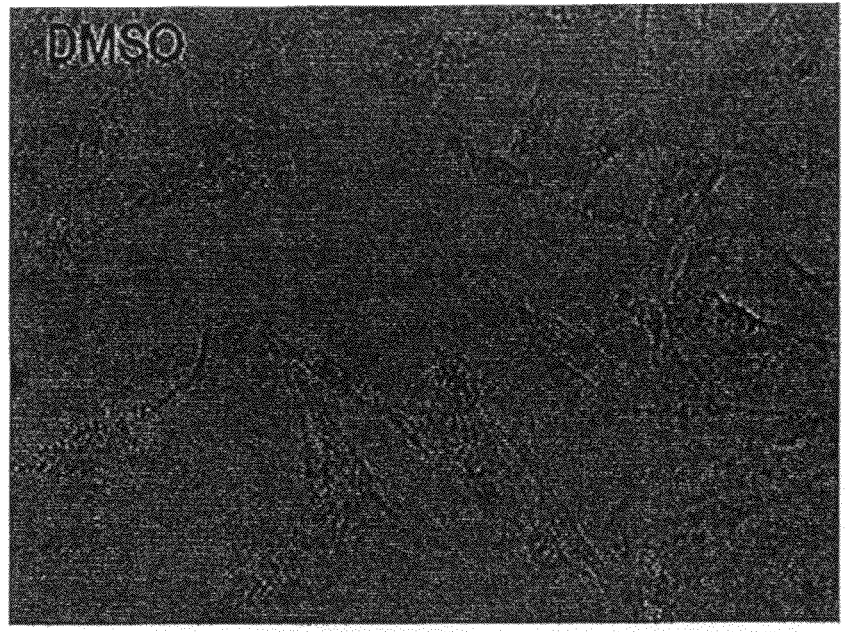
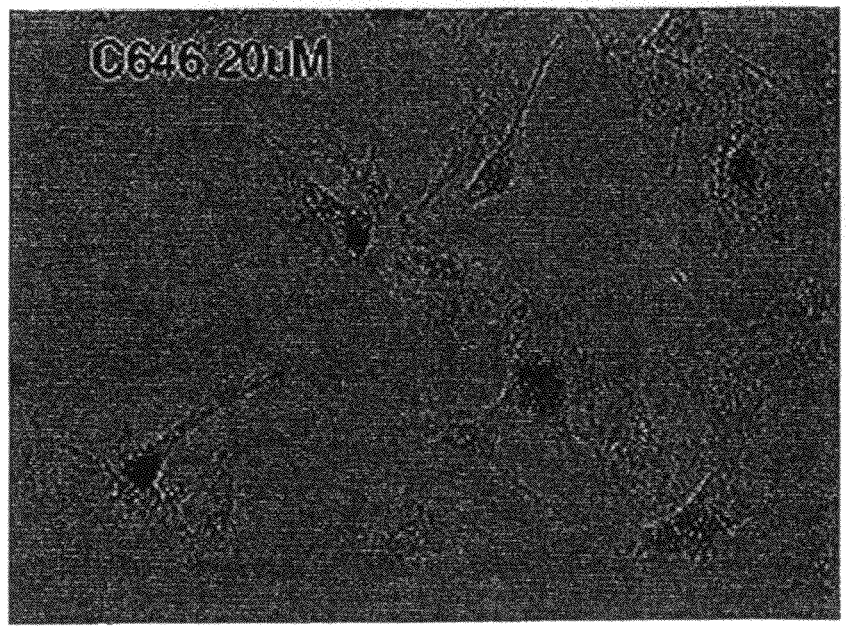

FIG. 14C
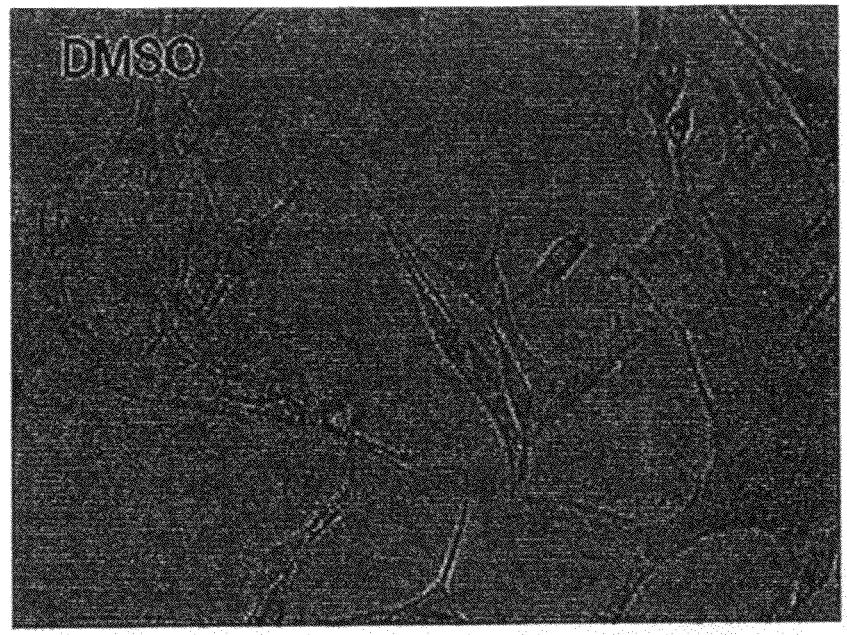
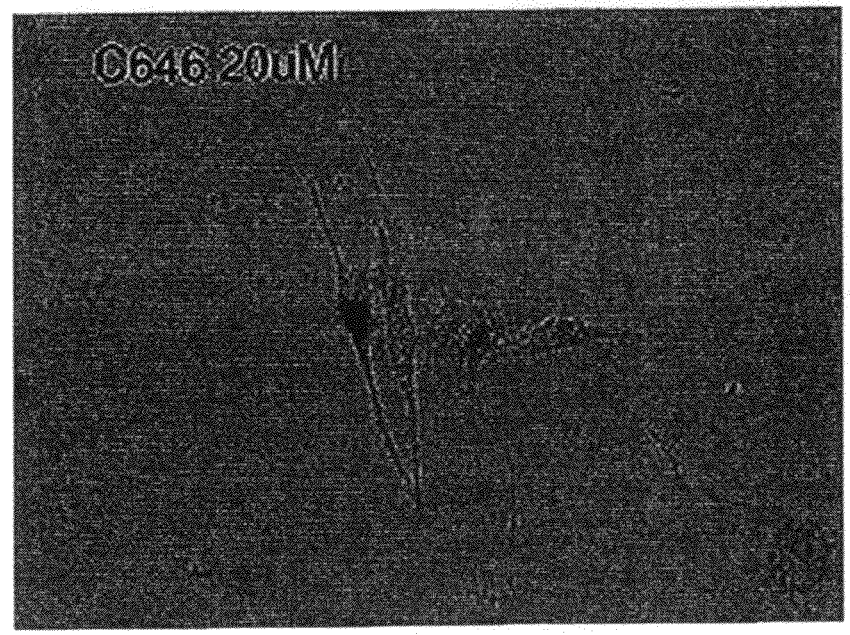

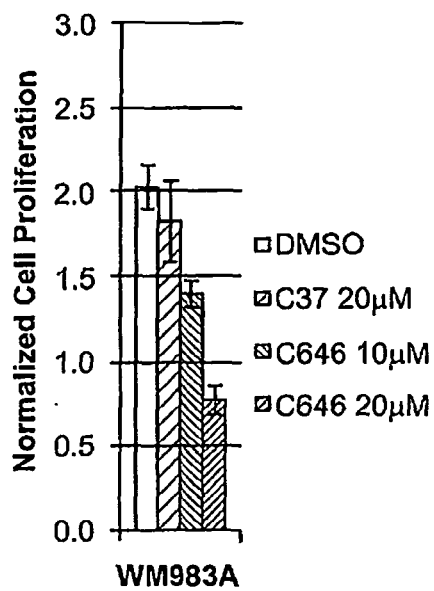
FIG. 15A
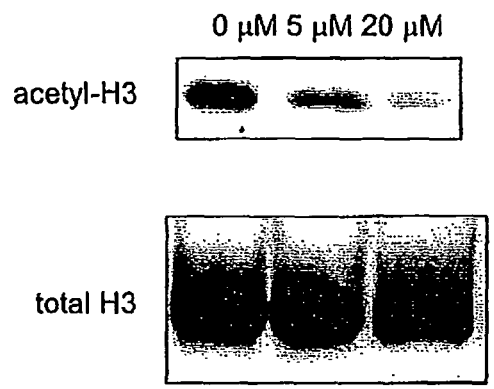
FIG. 15B
FIG. 15C
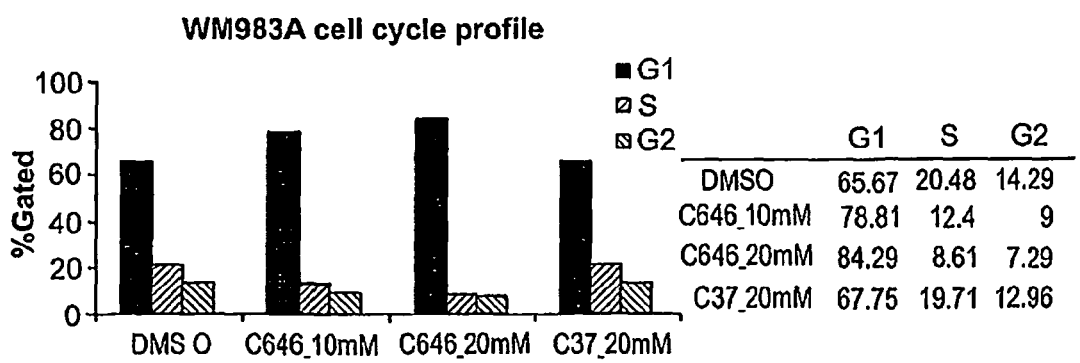

FIG. 17

Short Summary of GO analysis (genes downregulated by > 2 fold at 24h)

- Biological process
  – Negative regulation of mitotic metaphase/anaphase transition (p= 8.9e-7)
  – Regulation of cell cycle (p=2.12e-23)
  – Regulation of chromosome segregation (p=2.05e-7)
  – Regulation of microtubule-based process (p=1.31e-7)
  – G2/M transition DNA damage checkpoint (p=0.002)
  – Nucleosome assembly (p=2.88e-21)
  – DNA replication-dependent nucleosome assembly (p=4.35e-4)
  – Centromere complex assembly (p=7.81e-8)
  – Establishment of organelle localization (p=6.46e-8)

- Molecular function
  – Chromatin binding (p=6.64e-6)
  – Kinetochore binding (p=2.96e-5)
  – Damaged DNA binding (p=2.17e-5)
  – DNA bending activity (p=1.45e-3)
  – DNA clamp loader activity (p=7.29e-5)
  – Structure-specific DNA binding (p=3.29e-6)
  – ATP binding (p=1.43e-15)
  – Histone binding (p=3.46e-3)
  – Chromo shadow domain binding (p=5.48e-3)

FIG. 18C

| | PCR fold change relative to DMSO | | WM35 fold change relative to DMSO on array | |
|---|---|---|---|---|
| | WM35 | 1205LU | array probe 1 | array probe 2 |
| XRCC2 | -6.78 | -1.18 | -11.34 | -5.34 |
| CCNE2 | -16.72 | 1.02 | -12.70 | |
| UHRF1 | -24.99 | 1.04 | -14.51 | -7.72 |
| TIMP3 | 1.53 | 1.04 | 2.40 | |
| PRSS35 | 4.35 | 1.32 | 5.69 | |
| TRIM38 | 1.79 | n/a | 4.32 | 1.61 |
| DEPDC1 | -3.68 | n/a | -12.42 | -3.84 |
| FAM111B | -29.64 | n/a | -42.54 | |

FIG. 19B
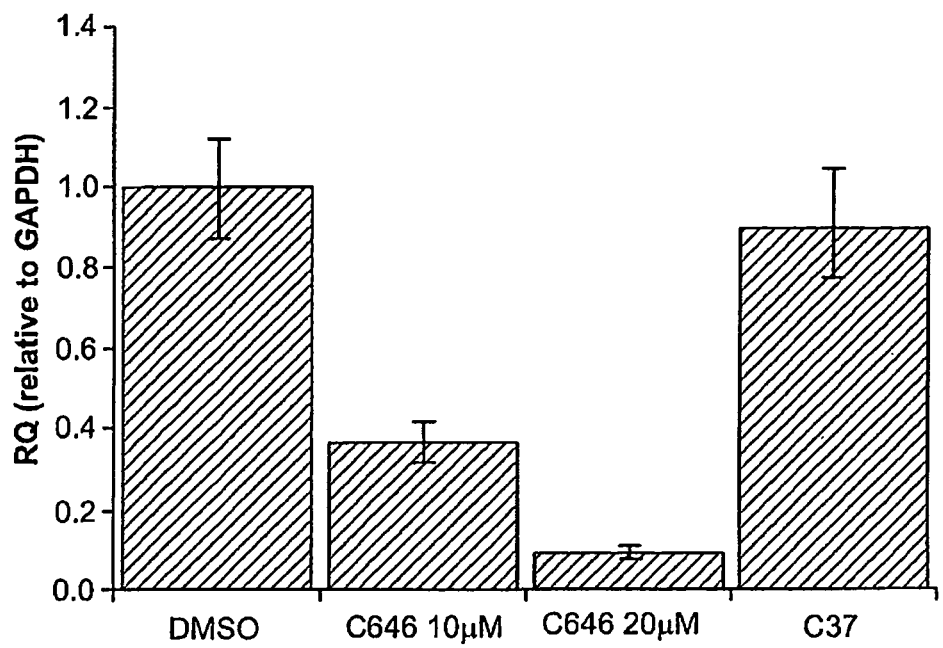
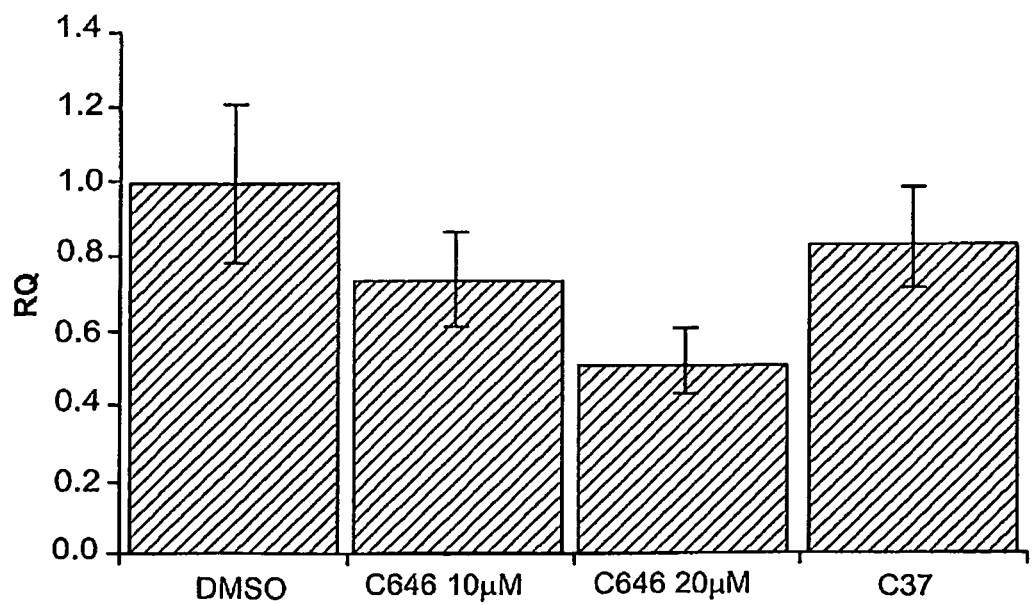

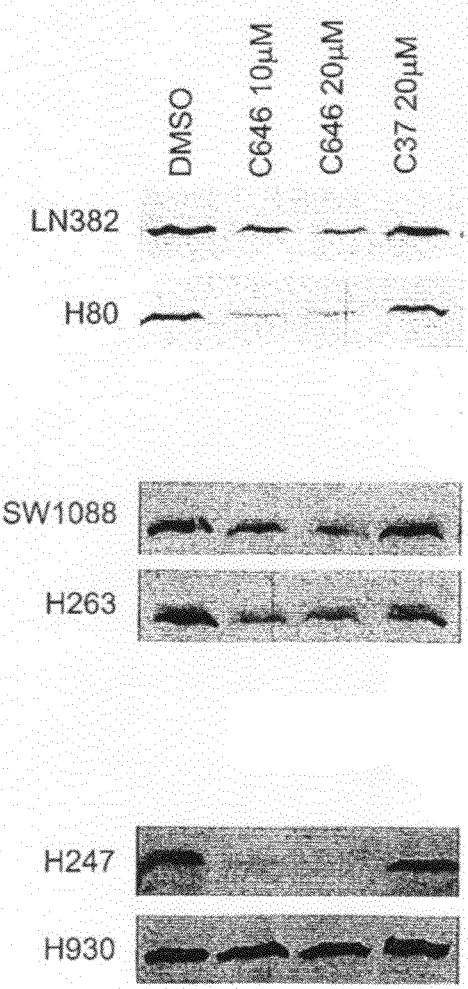

USE OF HISTONE ACETYLTRANSFERASE INHIBITORS AS NOVEL ANTI-CANCER THERAPIES

CROSS-REFERENCE TO RELATED APPLICATIONS

This application is a 35 U.S.C. 371 U.S. National Stage entry of International Application PCT/US2011/020271, having an international filing date of Jan. 5, 2011, which claims the benefit of U.S. Provisional Application 61/292,207, filed Jan. 5, 2010, the contents of both of which are incorporated herein by reference in its entirety.

BACKGROUND OF THE INVENTION

The reversible acetylation of histones and other proteins is a major mechanism for cellular regulation. Acetylation on protein lysine residues is catalyzed by histone acetyltransferases (HATs) and acetyl-Lys cleavage is performed by histone deacetylases (HDACs). These enzymes and the associated acetylation events have been implicated in a wide variety of physiological and disease processes, including tumorogenesis.

While studies on histone deacetylases have led to the discovery of highly potent compounds with clinical impact in cancer, the identification of histone acetyltransferase inhibitors has proved to be more challenging. For example, the most potent and selective compound, Lys-CoA, has been converted to a cell permeable form with Tat peptide attachment (Lys-CoA-Tat) and has been used in a variety of studies. However, the complexity of Lys-CoA-Tat limits its use in pharmacologic applications. High throughput screening experiments have led to the identification of several small molecule synthetic agents and natural product derivatives of moderate potency as p300/CBP HAT inhibitors, but their selectivity and mechanism of inhibition remains to be fully characterized.

Thus, there is a need in the art for the identification of novel HAT inhibitors. Characterization of novel HAT inhibitors are necessary to better understand the role of HATs in tumorogenesis, and as described herein, for use in treating cancers.

SUMMARY OF THE INVENTION

In one aspect, we have now discovered that inhibition of p300/CBP HAT results in inhibition of tumor cell growth. The effects of p300/CBP HAT inhibition is observed in a broad spectrum of tumor cells, including leukemia, brain cancer, lung cancer, central nervous system (CNS) cancer, melanoma, renal cancer, prostate cancer, colon cancer, ovarian cancer, and breast cancer cells. These growth effects correspond with cell arrest, apoptosis, and/or senescence. We also have identified the downstream effectors of p300/CBP HAT.

Accordingly, in one aspect, the invention provides methods for treating cancer in a subject by inhibiting the activity of p300/CBP HAT.

In another aspect, the invention provides methods for treating cancer by administering an effective amount of a p300/CBP HAT inhibitor to a subject in need thereof. In embodiments, the inhibitor is a p300-selective inhibitor. In embodiments, the inhibitor is C646, C146, or C375, or an analog or derivative thereof. In embodiments, the inhibitor is C646, or an analog or derivative thereof. In embodiments, the inhibitor is selected from the group consisting of compounds 6a-6r, or an analog or derivative thereof.

In embodiments, the subject is also administered radiation therapy or at least one additional anti-cancer agent. The radiation therapy can be any X-ray therapy or radiopharmaceutical therapy that is well-known in the art. The anti-cancer agent can be any chemotherapeutic agent that is well-known in the art, including those agents disclosed herein. In some embodiments, the anti-cancer agent is a DNA damaging chemotherapeutic agent, such as cisplatin or temozolamide.

In embodiments, the cancer is leukemia, brain cancer, lung cancer, CNS cancer, melanoma, renal cancer, prostate cancer, colon cancer, ovarian cancer, or breast cancer. In some embodiments, the cancer is brain cancer, lung cancer, or melanoma.

In embodiments, the subject is human.

In another aspect, the invention provides methods for inhibiting the growth, proliferation, or survival of a neoplastic cell by contacting the cell with an effective amount of a p300/CBP HAT inhibitor. In embodiments, the inhibitor is a p300-selective inhibitor. In embodiments, the inhibitor is C646, C146, or C375, or an analog or derivative thereof. In embodiments, the inhibitor is C646, or an analog or derivative thereof. In embodiments, the inhibitor is selected from the group consisting of compounds 6a-6r, or an analog or derivative thereof.

In embodiments, the neoplastic cell is also exposed to radiation therapy or contacted with at least one additional anti-cancer agent. The radiation therapy can be any X-ray therapy or radiopharmaceutical therapy that is well-known in the art. The anti-cancer agent can be any chemotherapeutic agent that is well-known in the art, including those agents disclosed herein. In some embodiments, the anti-cancer agent is a DNA damaging chemotherapeutic agent, such as cisplatin or temozolamide.

In embodiments, the neoplastic cell is from a leukemia, brain cancer, lung cancer, CNS cancer, melanoma, renal cancer, prostate cancer, colon cancer, ovarian cancer, or breast cancer. In some embodiments, the neoplastic cell is from brain cancer, lung cancer, or melanoma.

In embodiments, the method is carried out in vivo or in vitro.

In another aspect, the invention provides methods for selecting a treatment regimen for a subject diagnosed as having cancer. In embodiments, the method involves contacting a cancer cell of the subject with an agent and detecting an alteration in the expression of one or more of a biomarker identified in any one of Tables 4-6 in response to the agent. In embodiments, detection of an alteration indicates that the cancer is susceptible to treatment with the agent. In embodiments, the treatment regimen comprises administering the agent to the subject if the cancer is determined to be susceptible to treatment with the agent.

In embodiments, the inhibitor is a p300-selective inhibitor. In embodiments, the inhibitor is C646, C146, or C375, or an analog or derivative thereof. In embodiments, the inhibitor is C646, or an analog or derivative thereof. In embodiments, the inhibitor is selected from the group consisting of compounds 6a-6r, or an analog or derivative thereof.

In embodiments, the subject has also been treated with radiation therapy or at least one additional anti-cancer agent. The radiation therapy can be any X-ray therapy or radiopharmaceutical therapy that is well-known in the art. The anti-cancer agent can be any chemotherapeutic agent that is well-known in the art, including those agents disclosed herein. In some embodiments, the anti-cancer agent is a DNA damaging chemotherapeutic agent, such as cisplatin or temozolamide.

In embodiments, the cancer is leukemia, brain cancer, lung cancer, CNS cancer, melanoma, renal cancer, prostate cancer, colon cancer, ovarian cancer, or breast cancer. In some embodiments, the cancer is brain cancer, lung cancer, or melanoma.

In embodiments, the subject is human.

In another aspect, the invention provides methods for treating cancer in a patient in need thereof, using the treatment regimen from any of the above embodiments or any treatment regimen described herein.

In another aspect, the invention provides methods for monitoring therapeutic efficacy of a p300/CBP HAT inhibitor in a subject diagnosed as having cancer. In embodiments, the method involves detecting expression of one or more of a biomarker identified in any one of Tables 4-6 in a cancer cell of the subject before and after administration of a p300/CBP HAT inhibitor. In embodiments, the method involves comparing the expression of the biomarker before and after treatment. In some embodiments, detection of an alteration in expression indicates the therapeutic efficacy of the inhibitor.

In embodiments, the inhibitor is a p300-selective inhibitor. In embodiments, the inhibitor is C646, C146, or C375, or an analog or derivative thereof. In embodiments, the inhibitor is C646, or an analog or derivative thereof. In embodiments, the inhibitor is selected from the group consisting of compounds 6a-6r, or an analog or derivative thereof.

In embodiments, the cancer is leukemia, brain cancer, lung cancer, CNS cancer, melanoma, renal cancer, prostate cancer, colon cancer, ovarian cancer, or breast cancer. In some embodiments, the cancer is brain cancer, lung cancer, or melanoma.

In embodiments, the subject has also been treated with radiation therapy or at least one additional anti-cancer agent. The radiation therapy can be any X-ray therapy or radiopharmaceutical therapy that is well-known in the art. The anti-cancer agent can be any chemotherapeutic agent that is well-known in the art, including those agents disclosed herein. In some embodiments, the anti-cancer agent is a DNA damaging chemotherapeutic agent, such as cisplatin or temozolamide.

In embodiments, the subject is human.

In another aspect, the invention provides methods for treating cancer in a subject by administering an effective amount of a p300/CBP HAT inhibitor in combination with radiation therapy or at least one additional anti-cancer agent to a subject in need thereof. In embodiments, the inhibitor is a p300-selective inhibitor. In embodiments, the inhibitor is C646, C146, or C375, or an analog or derivative thereof. In embodiments, the inhibitor is C646, or an analog or derivative thereof. In embodiments, the inhibitor is selected from the group consisting of compounds 6a-6r, or an analog or derivative thereof.

The radiation therapy can be any X-ray therapy or radiopharmaceutical therapy that is well-known in the art. The anti-cancer agent can be any chemotherapeutic agent that is well-known in the art, including those agents disclosed herein. In some embodiments, the anti-cancer agent is a DNA damaging chemotherapeutic agent, such as cisplatin or temozolamide.

In embodiments, the cancer is leukemia, brain cancer, lung cancer, CNS cancer, melanoma, renal cancer, prostate cancer, colon cancer, ovarian cancer, or breast cancer. In some embodiments, the cancer is brain cancer, lung cancer, or melanoma.

In embodiments, the subject is human.

In another aspect, the invention provides methods for inhibiting the growth, proliferation, or survival of a neoplastic cell by contacting the cell with an effective amount of a p300/CBP HAT inhibitor in combination with exposing the cell to radiation therapy or contacting the cell with at least one additional anti-cancer agent. In embodiments, the inhibitor is a p300-selective inhibitor. In embodiments, the inhibitor is C646, C146, or C375, or an analog or derivative thereof. In embodiments, the inhibitor is C646, or an analog or derivative thereof. In embodiments, the inhibitor is selected from the group consisting of compounds 6a-6r, or an analog or derivative thereof.

The radiation therapy can be any X-ray therapy or radiopharmaceutical therapy that is well-known in the art. The anti-cancer agent can be any chemotherapeutic agent that is well-known in the art, including those agents disclosed herein. In some embodiments, the anti-cancer agent is a DNA damaging chemotherapeutic agent, such as cisplatin or temozolamide.

In embodiments, the neoplastic cell is from a leukemia, brain cancer, lung cancer, CNS cancer, melanoma, renal cancer, prostate cancer, colon cancer, ovarian cancer, or breast cancer. In some embodiments, the neoplastic cell is from brain cancer, lung cancer, or melanoma.

In embodiments, the method is carried out in vivo or in vitro.

In any of the above aspects, a related embodiment is administering a p300/CBP HAT inhibitor in combination with a pharmaceutically acceptable carrier.

In another aspect, the invention provides novel inhibitors of p300/CBP HAT. In embodiments, the inhibitor is selected from the group consisting of compounds 6a-6r, or a salt, an analog or derivative thereof. In certain embodiments, the compound is represented by Formula I:

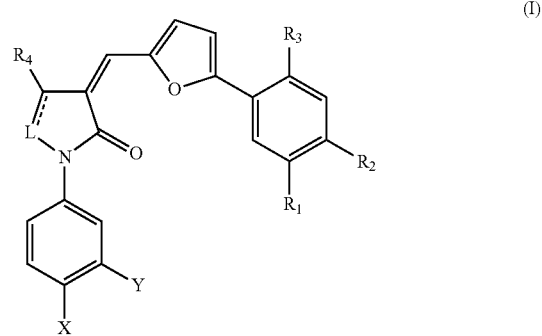

in which
X is H, C(O)-Q or S(O)$_2$-Q;
Y is H, halogen, or C(O)-Q, provided that if X is H, Y is C(O)-Q;
L is C(O) or N;
the dashed line represents a bond if L is N, and is absent if L is C(O);
$R_1$ and $R_2$ are independently H or $C_1$-$C_4$alkyl; and
$R_3$ is halogen, C(O)-Q, NO$_2$, CN, or CH$_2$OH;
$R_4$ is H or methyl;
Q is OH, O—$C_1$-$C_4$alkyl, —NH$_2$, or NH($C_1$-$C_4$alkyl); or a salt thereof;
provided that:
if X is COOH, Y is H, L is N, $R_4$ is methyl, and $R_1$ and $R_2$ are each CH$_3$, then $R_3$ is not COO-ethyl or NO$_2$;
if X is COOH, Y is H, L is N, $R_4$ is methyl, and $R_1$ and $R_2$ are each H, then $R_3$ is not COO-ethyl;
if X is COOH, Y is H, L is N, $R_4$ is methyl, and $R_1$ and $R_2$ are each H, then $R_3$ is not F;
if X is COOH, Y is H, L is N, $R_4$ is methyl, $R_1$ is CH$_3$, and $R_2$ is H, then $R_3$ is not NO$_2$;
if X is COO-ethyl, Y is H, L is N, $R_4$ is methyl, and $R_1$ and $R_2$ are each CH$_3$, then $R_3$ is not NO$_2$;

if X is H, Y is COOH, L is N, $R_4$ is methyl, and $R_1$ and $R_2$ are each $CH_3$, then $R_3$ is not $NO_2$;

if X is $SO_3H$, Y is H, L is N, $R_4$ is methyl, and $R_1$ and $R_2$ are each $CH_3$, then $R_3$ is not $NO_2$; and if X is $CONH_2$, Y is H, L is N, $R_4$ is methyl, and $R_1$ and $R_2$ are each $CH_3$, then $R_3$ is not $NO_2$.

Additional objects and advantages of the invention will be set forth in part in the description which follows, and in part will be obvious from the description, or may be learned by practice of the invention. The objects and advantages of the invention will be realized and attained by means of the elements and combinations disclosed herein, including those pointed out in the appended claims. It is to be understood that both the foregoing general description and the following detailed description are exemplary and explanatory only and are not restrictive of the invention as claimed. The accompanying drawings, which are incorporated in and constitute a part of this specification, illustrate several embodiments of the invention and, together with the description, serve to explain the principles of the invention.

DEFINITIONS

To facilitate an understanding of the present invention, a number of terms and phrases are defined below.

As used herein, the singular forms "a", "an", and "the" include plural forms unless the context clearly dictates otherwise. Thus, for example, reference to "a biomarker" includes reference to more than one biomarker.

As used herein, the term "alkyl" refers to a straight or branched chain or cyclic saturated aliphatic hydrocarbon. Alkyl groups include groups having 1 to 4 carbon atoms ($C_1$-$C_4$alkyl), such as methyl, ethyl, propyl, isopropyl, n-butyl, sec-butyl, ten-butyl, cyclopropyl, and cyclopropylmethyl. In certain embodiments, preferred alkyl groups are straight or branched chain.

The term "halogen" refers to fluorine, chlorine, bromine or iodine.

A "pharmaceutically acceptable salt" of a compound recited herein is an acid or base salt that is generally considered in the art to be suitable for use in contact with the tissues of human beings or animals without excessive toxicity, irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—$(CH_2)_n$—COOH where n is 0-4, and the like. Similarly, pharmaceutically acceptable cations include, but are not limited to sodium, potassium, calcium, aluminum, lithium and ammonium. Those of ordinary skill in the art will recognize further pharmaceutically acceptable salts for the compounds provided herein, including those listed by *Remington's Pharmaceutical Sciences,* 17th ed., Mack Publishing Company, Easton, Pa., p. 1418 (1985). In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in an appropriate solvent.

As used herein, the terms "comprises," "comprising," "containing," "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

As used herein, the terms "cancer" and "cancerous" refer to or describe the physiological condition in mammals, in which a population of cells are characterized by unregulated cell growth. Examples of cancer include, but are not limited to, carcinoma, lymphoma, blastoma, sarcoma, and leukemia. Nonlimiting examples of such cancers include squamous cell cancer, small-cell lung cancer, non-small cell lung cancer, adenocarcinoma of the lung, squamous carcinoma of the lung, lung cancer, leukemia, cancer of the peritoneum, hepatocellular cancer, gastrointestinal cancer, pancreatic cancer, glioblastoma (i.e., brain cancer), CNS cancer, cervical cancer, ovarian cancer, liver cancer, bladder cancer, hepatoma, breast cancer, colon cancer, colorectal cancer, endometrial or uterine carcinoma, salivary gland carcinoma, kidney/renal cancer, liver cancer, melanoma, prostate cancer, vulval cancer, thyroid cancer, hepatic carcinoma and various types of head and neck cancer.

The terms "proliferative disorder" and "proliferative disease" refer to disorders associated with abnormal cell proliferation, such as cancer.

"Tumor" as used herein refers to any mass of tissue that results from excessive cell growth or proliferation, either benign (noncancerous) or malignant (cancerous) including pre-cancerous lesions.

The term "neoplastic" refers to those cells having the capacity for autonomous growth, i.e., an abnormal state or condition characterized by rapidly proliferating cell growth. A neoplastic disease state may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness.

As used herein, the term "inhibit tumor growth" and its grammatical equivalents refer to any mechanism by which tumor cell growth can be inhibited. In certain embodiments, tumor cell growth is inhibited by slowing proliferation of tumor cells. In certain embodiments, tumor cell growth is inhibited by halting proliferation of tumor cells. In certain embodiments, tumor cell growth is inhibited by killing tumor cells. In certain embodiments, tumor cell growth is inhibited by inducing apoptosis of tumor cells. In certain embodiments, tumor cell growth is inhibited by preventing migration of tumor cells. In certain embodiments, tumor cell growth is inhibited by preventing invasion of tumor cells.

As used herein, the term "p300/CBP HAT inhibitor" refers to an agent that inhibits the histone acetyltransferase activity of p300/CBP HAT as measured by an inhibition assay that is well-known in the art, including the coupled spectrophotometric assay, the direct radioactive assay, and the HAT assays described in detail herein. The inhibitor can be any small molecule chemical compound or fragments thereof, including analogs of such compounds or fragments. A p300/CBP HAT inhibitor is not required to produce 100% inhibition. An agent is a p300/CBP HAT inhibitor if addition of the agent in an inhibition assay corresponds with a measurable decrease in histone acetyltransferase activity.

Terms such as "treating," "treatment," "to treat," "alleviating," and "to alleviate" refer to both 1) therapeutic measures that cure, slow down, lessen symptoms of, and/or halt progression of a diagnosed pathologic condition or disorder, and 2) prophylactic or preventative measures that prevent or slow the development of a targeted pathologic condition or disorder. Thus, those in need of treatment include those already with the disorder; those prone to have the disorder; and those in whom the disorder is to be prevented. A subject is successfully "treated" according to the methods of the present invention if the patient shows one or more of the following: a reduction in the number of or complete absence of cancer cells; a reduction in the tumor size; inhibition of or an absence of cancer cell infiltration into peripheral organs, including the spread of cancer into soft tissue and bone; inhibition of or an absence of tumor metastasis; inhibition or an absence of tumor growth; relief of one or more symptoms associated with the specific cancer; reduced morbidity and mortality; and improvement in quality of life. The term "treatment" is intended to encompass prophylaxis, therapy, and cure.

By "ameliorate" is meant decrease, suppress, attenuate, diminish, arrest, or stabilize the development or progression of a disease or a symptom thereof.

"Administering" is defined herein as a means of providing an agent or a composition containing the agent to a subject in a manner that results in the agent being inside the subject's body. Such an administration can be by any route including, without limitation, oral, subcutaneous, intradermal, intravenous, intra-arterial, intraperitoneal, and intramuscular.

The term "sample" is defined herein as blood, blood product, biopsy tissue, serum, and any other type of fluid or tissue that can be extracted from a subject or a mammal. The terms "sample" and "biological sample" are used interchangeably in this application.

The term "subject" or "patient" refers to an animal which is the object of treatment, observation, or experiment. By way of example only, a subject includes, but is not limited to, a mammal, including, but not limited to, a human or a non-human mammal, such as a bovine, equine, canine, ovine, or feline.

By "effective amount" is meant the amount of an agent required to ameliorate the symptoms of a disease relative to an untreated patient or to produce some desired therapeutic effect. The effective amount of active compound(s) used to practice the present invention for prevention or treatment of a disease varies depending upon the manner of administration, the age, body weight, and general health of the subject. Ultimately, the attending physician or veterinarian will decide the appropriate amount and dosage regimen. Such amount is referred to as an "effective" amount.

A physician or veterinarian having ordinary skill in the art can readily determine and prescribe the "effective amount" ($ED_{50}$) of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

Typically a therapeutically effective dosage should produce a serum concentration of compound of from about 0.1 ng/ml to about 50-100 µg/ml. The pharmaceutical compositions typically should provide a dosage of from about 0.001 mg to about 2000 mg of compound per kilogram of body weight per day. For example, dosages for systemic administration to a human patient can range from 1-10 µg/kg, 20-80 µg/kg, 5-50 µg/kg, 75-150 µg/kg, 100-500 µg/kg, 250-750 µg/kg, 500-1000 µg/kg, 1-10 mg/kg, 5-50 mg/kg, 25-75 mg/kg, 50-100 mg/kg, 100-250 mg/kg, 50-100 mg/kg, 250-500 mg/kg, 500-750 mg/kg, 750-1000 mg/kg, 1000-1500 mg/kg, 1500-2000 mg/kg, 5 mg/kg, 20 mg/kg, 50 mg/kg, 100 mg/kg, 500 mg/kg, or 1000 mg/kg. Pharmaceutical dosage unit forms are prepared to provide from about 1 mg to about 1000 mg, for example from about 10 to about 500 mg of the compound or a combination of essential ingredients per dosage unit form.

The terms "prediction," "predicting," "prognostic," or "prognosis" are used herein to refer to the likelihood that a subject will respond either favorably or unfavorably to an agent (e.g., an anti-cancer compound) or set of agents, and also the extent of those responses. The predictive methods described herein are valuable tools in predicting if a patient suffering from a cancer is likely to respond favorably to a p300/CBP HAT inhibitor compound treatment regimen alone or in combination with another therapeutic agent (e.g., a second anti-cancer compound).

By "agent" is meant any small molecule chemical compound, antibody, nucleic acid molecule, or polypeptide, or fragments thereof.

"Marker" or "biomarker" in the context of the present invention refer to a polypeptide or nucleic acid whose activity or expression is quantitatively correlated to a phenotypic state of interest (e.g., a cell after treatment with a p300/CBP inhibitor). The term "biomarker" is used interchangeably with the term "marker."

By "analog" is meant a molecule that is not identical, but has analogous functional or structural features. For example, an amide, ester, carbamate, carbonate, ureide, or phosphate analog of a compound is a molecule that either: 1) does not destroy the biological activity of the compound and confers upon that compound advantageous properties in vivo, such as uptake, duration of action, or onset of action; or 2) is itself biologically inactive but is converted in vivo to a biologically active compound.

As used herein, the terms "polynucleotide" and "nucleic acid" refer to a polymer composed of a multiplicity of nucleotide units (ribonucleotide or deoxyribonucleotide or related structural variants) linked via phosphodiester bonds, including but not limited to, DNA or RNA. The term encompasses sequences that include any of the known base analogs of DNA and RNA.

The term "gene" refers to a nucleic acid (e.g., DNA) molecule that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA.

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified. Amino acid analogs refers to compounds that have the same basic chemical structure as a naturally occurring amino acid, e.g., an alpha carbon that is bound to a hydrogen, a carboxyl group, an amino group, and an R group, e.g., homoserine, norleucine, methionine sulfoxide, methionine methyl sulfonium. Such analogs can have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

The term "gene expression profiling" and its grammatical equivalents, unless otherwise specified, are used in the broadest sense, and include methods of quantification of a gene's mRNA or nucleic acids derived therefrom, and/or protein levels or peptides derived therefrom and/or protein functions in a biological sample.

The terms "differentially expressed gene," "differential gene expression," and their grammatical equivalents, are used interchangeably and refer to a gene whose expression is upregulated or downregulated in a first cell population relative to the expression of the same gene in a second population of cells. Such differences are evidenced by, e.g., a change in mRNA levels, surface expression, secretion or other partitioning of a polypeptide. Differential gene expression includes, in some embodiments, a comparison of expression between two or more genes or their gene products, or a comparison of the ratios of the expression between two or more genes or their gene products, or even a comparison of two differently processed products of the same gene, which differ between two populations of cells. Differential expression includes both quantitative, as well as qualitative, differences in the temporal or cellular expression pattern in a gene or its expression products among, for example, normal and diseased cells, among cells which have undergone different disease events or exposure to different agents/compounds, or cells that are significantly sensitive or resistant to certain therapeutic drugs.

The term "microarray" refers to an ordered arrangement of hybridizable array elements, preferably polynucleotide probes, on a substrate.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

DESCRIPTION OF THE DRAWINGS

FIG. 2 shows the inhibitory characteristics of C646.

FIG. 3A is a graph showing the pattern of inhibition of C146 vs. acetyl-CoA. [H4-15]. 100 μM. Data were fit to a noncompetitive inhibition model. C146 $K_{is}$=-4.7±0.8 μM, $K_{ii}$=34±5 μM, apparent acetyl-CoA $K_m$=8.4±0.8 μM, and apparent $k_{cat}$=24±1 min$^{-1}$. FIG. 3B is a graph showing the pattern of inhibition of C375 vs. acetyl-CoA. [H4-15]=100 μM. Data were fit to a noncompetitive inhibition model. C375 $K_{is}$=$K_{ii}$=4.8±0.5 μM, apparent acetyl-CoA $K_m$=12±2 μM, and apparent $k_{cat}$=11±1 min$^{-1}$. FIG. 3C is a graph showing the pattern of inhibition of C146 vs. H4-15. [acetyl-CoA]=10 μM. Data were fit to a competitive inhibition model. C146 $K_i$=5.9±0.5 μM, apparent H4-15 $K_m$=190±17 μM, and apparent $k_{cat}$=57±2 min$^{-1}$.

FIGS. 4A and 4B show the NMR and HPLC results for C646. FIG. 4A is a 2D-1H-1H COSY and NOESY spectra. The spectra shows an NOE between the vinyl proton and the methyl group (highlighted in red and green) in the major E-isomer. FIG. 4B includes HPLC results. Reversed phase HPLC analysis of C646 shows two well-defined isomers (elution with a water:acetonitrile gradient, 0.05% trifluoroacetic acid). The NMR and HPLC analysis of C646 reveals two interconverting olefinic stereoisomers.

FIG. 9A includes an SDS gel. Histones were extracted and analysed by Western blotting to visualize total H3 and H3K9ac. FIG. 9B includes an acid-urea gel. Histones were extracted and analysed by western blotting to visualize F13, H3K9ac, and H4K12ac. Acid-urea gels separate histones on the basis of charge. Each acetylation event incrementally retards migration to produce a 'ladder' of bands. The numbers on either side of the blot indicates the extent of modification. (lane 1, untreated control cells; lane 5, TSA-treated cells).

FIGS. 10A-10C show the growth inhibitory effect of C646 on melanoma and lung cancer cells. FIG. 10A is a graph showing that C646 has a more potent effect on cell growth than Lys-CoA-Tat. Cells were treated for 24 hours and proliferation was measured via $^3$H-thymidine incorporation pre- and post-treatment. Data for each cell line were normalized to $^3$H counts measured pre-treatment. C37 is an inactive derivative of C646. DMSO serves as a vehicle control for C37 and C646. Ac-DDDD-Tat is a control peptide for Lys-CoA-Tat. WM35, WM983A, and 1205Lu are melanoma cell lines representing three stages of cancer progression: radial, vertical, and metastatic, respectively. FIG. 10B is a graph showing that two out of three non-small cell lung adenocarcinoma cell lines demonstrate significant growth inhibition after treatment with C646 and Lys-CoA-Tat for 24 hours. FIG. 10C is a graph showing that C646 does not have a significant inhibitory effect on NIH3T3 cell proliferation.

FIGS. 13A-13C show the effects of C646 on the NCI-60 panel of tumor cell lines. 60 tumor cell lines from the NCI-60 panel were treated with varying doses of C646. Cell growth was assessed after 48 hours. FIG. 13A includes a bar graph. Bars to the RIGHT of zero indicate cell death, while bars to the LEFT of zero indicate cell growth inhibition. FIG. 13B shows the dose response curves for the leukemia, lung cancer, CNS cancer, melanoma, renal cancer, and prostate cancer cell lines. FIG. 13C shows the dose response curves for the colon cancer, ovarian cancer, and breast cancer cell lines.

FIGS. 14A-14C show the ability of C646 to induce apoptosis or senescence in tumor cells. FIG. 14A includes scatter plots. WM35 melanoma cells were treated with C646 or DMSO (control) for 72 hours, stained with annexin V and propidium iodide, and assessed by FACS. WM35 melanoma cells were also treated with camptothecin as a positive control for apoptosis. FIGS. 14B and 14C include images of the treated cells stained for senescence-associated beta galactosidase. In FIG. 14B, the WM35 melanoma cells were treated with C646 or DMSO (control) for 72 hours in the presence of 10% serum. In FIG. 14C, the WM35 melanoma cells were treated with C646 or DMSO (control) for 72 hours in the presence of 2% serum.

FIGS. 15A-15E show the effects of C646 on WM983A melanoma cells. FIG. 15A is a graph showing inhibition of WM983A melanoma cell proliferation after treatment with C646. Cells were treated with each compound for 24 hours, and proliferation was measured via $^3$H-thymidine incorporation. FIG. 15B is a Western blot showing that C646 blocks H3 acetylation in WM983A cells. Cells were treated for 6 hours with increasing doses of C646. Nuclear lysates were subjected to Western blot analysis for acetylated H3 (Upstate 06-599). Total H3 (Abeam ab1791) was blotted as a loading control. FIGS. 15C, 15D, and 15E include bar graphs showing that C646 causes growth arrest in the melanoma cell lines WM983A, WM35, and 1205Lu, respectively. Cells were treated for 48 hours with C646 or DMSO (control), collected and stained with propidium iodide, and then analyzed by FACS.

FIG. 16A is a graph showing the effects of C646 in combination with cisplatin or temozolamide on Mel-1 melanoma cells. Cells were grown in the presence of 2 µM C646 for 24 hours. The cells were given fresh medium (i.e., no C646) and either 1 µM cisplatin or 200 µM of temozolamide was added. Total cell number was counted on Day 0, 24 hours after addition of C646, and 48 hours after addition of cisplatin or temozolamide. FIG. 16B is a graph showing the effects of cisplatin or temozolamide on Mel-1 melanoma cells in the absence of C646. The cells were grown for 24 hours in medium. The cells were given fresh medium and either 1 µM of cisplatin or 200 µM of temozolamide was added. Total cell number was counted on Day 0, at 24 hours, and 48 hours after addition of cisplatin or temozolamide.

FIG. 17 is a summary of the gene profiling experiments performed on WM35 melanoma cells treated with 20 µM C646 for 24 hours.

FIGS. 18A-18C show expression of genes in WM35 melanoma cells as determined by quantitative PCR. WM35 melanoma cells, and the melanoma cells from a less sensitive cell line, 1205Lu, were treated with 20 µM C646 or DMSO (control) for 24 hours. Gene expression was measured by qualitative PCR. FIG. 18A shows the expression data for several genes that were downregulated in the corresponding microarray experiment. FIG. 18B shows the expression data for several genes that were upregulated in the corresponding microarray experiment. FIG. 18C includes a table comparing the expression data obtained from the PCR and the microarray experiments.

FIGS. 19A and 19B show the effects of p300/CBP HAT inhibition on cyclin A protein expression in melanoma cells. FIG. 19A is a Western blot showing the effect of C646 on cyclin A expression in melanoma cells. Four cell lines, three of which demonstrate potent growth inhibition after treatment with C646 (WM35, W983A, and W983B) and one that does not (1205Lu), were treated with 10-20 µM C646 or 20 µM C37, a compound that does not detectably block p300 HAT activity. The drug-sensitive cell lines exhibited lower levels of cyclin A expression, indicating that cyclin A protein expression correlates with melanoma cell sensitivity to C646. FIG. 19B is a graph showing the levels of cyclin A transcript in WM35 and 1205 melanoma cells after 24 hours treatment with 10-20 µM C646.

FIGS. 20A and 20B show the effects of p300/CBP HAT inhibition on cyclin A protein expression in glioblastoma cells. FIG. 20A is a Western blot showing the effect of C646 on cyclin A expression in the glioblastoma cells. Six cell lines were treated with 10-20 µM C646 or 20 µM C37, a compound that does not detectably block p300 HAT activity. Five of the cell lines exhibited lower levels of cyclin A expression, indicating that cyclin A protein expression correlates with glioblastoma cell sensitivity to C646. FIG. 20B is a graph showing the levels of cyclin A transcript in the glioblastoma cells after 24 hours treatment with 10-20 µM C646. The $IC_{50}$ of C646 for the cells ranged from 14.4 µM (H247) to 35.5 µM (LN382).

DETAILED DESCRIPTION OF THE INVENTION

Figure 1:
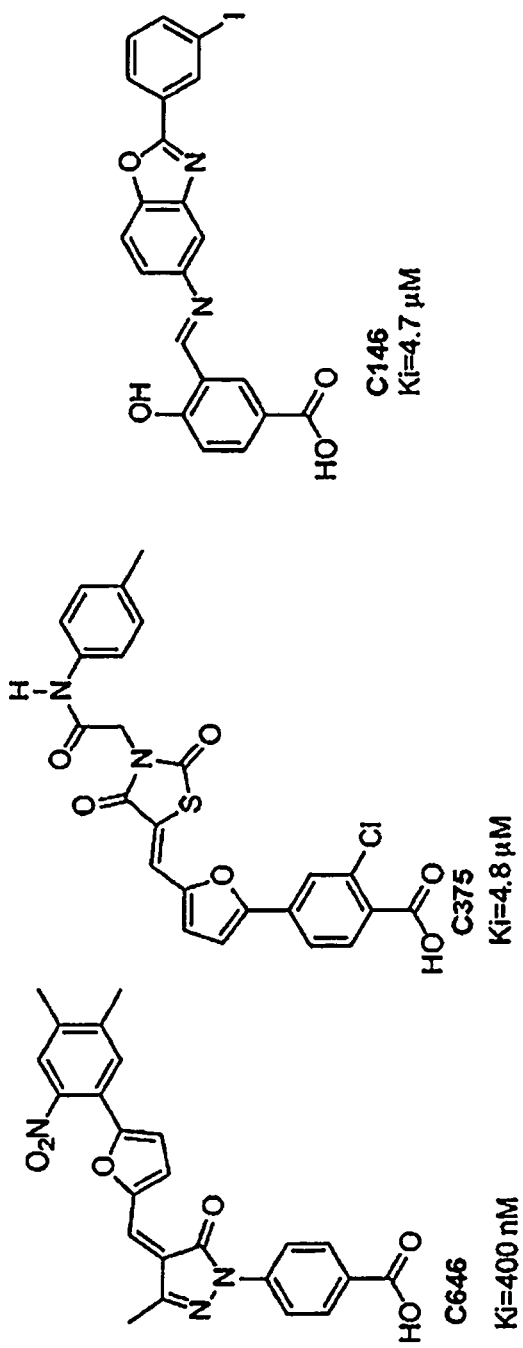
FIG. 1 shows the structures of the p300/CBP HAT small molecule inhibitors C646, C375, and C146, and their inhibitory constants identified from the virtual ligand screen.

The transcriptional coactivator p300/CBP is a histone acetyltransferase (HAT) that regulates gene expression by acetylating histones and other transcription factors. Dysregulation of p300/CBP HAT activity contributes to various diseases, including cancer. As described herein, it has now been demonstrated that p300/CBP HAT inhibition results in inhibition of tumor cell growth. Accordingly, the present invention provides methods for treating cancer or inhibiting the growth of tumor cells by administering to a subject in need thereof an effective amount of a p300/CBP HAT inhibitor. The invention also relates to combination therapies, as well as methods for monitoring the effectiveness of treatment.

p300/CBP Histone Acetyltransferase (HAT) Inhibitors and Analogs Thereof

In general, the invention includes an agent that inhibits the activity of p300/CBP HAT. The inhibitor can be any small molecule chemical compound or fragments thereof that is capable of inhibiting the activity of p300/CBP HAT.

For example, as described in detail below and in International Application No. PCT/US2008/067477 (published as WO 2008/157680), the entirety of which is herein incorporated by reference, information about the Lys-CoA/p300 HAT structure can be used in a virtual ligand screening assay to screen and identify agents that will likely be effective p300 HAT inhibitors. The selected candidates can then be screened using an inhibition assay that is well-known in the art, including the coupled spectrophotometric assay, the direct radioactive assay, and the HAT assays described in detail herein.

The present invention therefore includes p300/CBP HAT inhibitors. In embodiments, the inhibitor is one of the small molecule chemical compounds described herein that is capable of inhibiting p300/CBP activity. An exemplary p300/CBP HAT inhibitor is the small molecule C646.

As p300/CBP HAT inhibition results in inhibition of tumor cell growth, the present invention includes p300/CBP HAT inhibitors that are capable of inhibiting tumor cell growth. In embodiments, the inhibitor is one of the small molecule chemical compounds described herein that is capable inhibiting tumor cell growth. An exemplary p300/CBP HAT inhibitor is C646.

In certain embodiments, the compound is represented by Formula I:

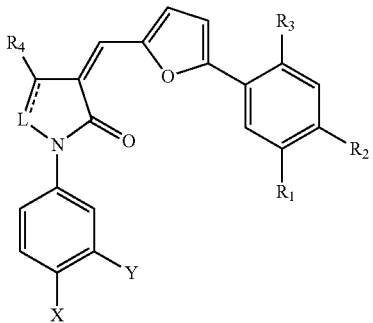

(I)

in which
X is H, C(O)-Q or S(O)$_2$-Q;
Y is H, halogen, or C(O)-Q, provided that if X is H, Y is C(O)-Q;
L is C(O) or N;
the dashed line represents a bond if L is N, and is absent if L is C(O);
$R_1$ and $R_2$ are independently H or $C_1$-$C_4$alkyl; and
$R_3$ is halogen, C(O)-Q, NO$_2$, CN, or CH$_2$OH;
$R_4$ is H or methyl;
Q is OH, O—$C_1$-$C_4$alkyl, NH$_2$, or NH($C_1$-$C_4$alkyl);
or a salt (e.g., a pharmaceutically acceptable salt) thereof; provided that:
if X is COOH, Y is H, L is N, $R_4$ is methyl, and $R_1$ and $R_2$ are each CH$_3$, then $R_3$ is not COO-ethyl or NO$_2$;
if X is COOH, Y is H, L is N, $R_4$ is methyl, and $R_1$ and $R_2$ are each H, then $R_3$ is not COO-ethyl;
if X is COOH, Y is H, L is N, $R_4$ is methyl, and $R_1$ and $R_2$ are each H, then $R_3$ is not F;
if X is COOH, Y is H, L is N, $R_4$ is methyl, $R_1$ is CH$_3$, and $R_2$ is H, then $R_3$ is not NO$_2$;
if X is COO-ethyl, Y is H, L is N, $R_4$ is methyl, and $R_1$ and $R_2$ are each CH$_3$, then $R_3$ is not NO$_2$;
if X is H, Y is COOH, L is N, $R_4$ is methyl, and $R_1$ and $R_2$ are each CH$_3$, then $R_3$ is not NO$_2$;
if X is SO$_3$H, Y is H, L is N, $R_4$ is methyl, and $R_1$ and $R_2$ are each CH$_3$, then $R_3$ is not NO$_2$; and if X is CONH$_2$, Y is H, L is N, $R_4$ is methyl, and $R_1$ and $R_2$ are each CH$_3$, then $R_3$ is not NO$_2$.

In certain embodiments of Formula I, $R_3$ is C(O)-Q, such as C(O)—O—$C_1$-$C_4$alkyl, and more preferably C(O)O-ethyl. In certain embodiments of Formula I, $R_3$ is NO$_2$. In certain embodiments of Formula I, $R_3$ is CN. In certain embodiments of Formula I, $R_3$ is CH$_2$OH. In certain embodiments of Formula I, $R_3$ is F.

In certain embodiments of Formula I, X is C(O)-Q, such as COOH or C(O)—O—$C_1$-$C_4$alkyl. In certain embodiments of Formula I, X is S(O)$_2$-Q, such as SO$_3$H, S(O)$_2$NHMe or S(O)$_2$NH$_2$.

In certain embodiments of Formula I, if X is H, then Y is C(O)—O—$C_1$-$C_4$alkyl.

In certain embodiments of Formula I, Y is H. In certain embodiments, Y is Cl.

In certain embodiments of Formula I, L is N. In other embodiments of Formula I, L is C(O).

In certain embodiments of Formula I, $R_1$ and $R_2$ are independently $C_1$-$C_4$alkyl, more preferably methyl.

In certain embodiments of Formula I, if L is N, then $R_4$ is methyl. In certain embodiments of Formula I, if L is C(O), then $R_4$ is H.

In certain embodiments, the compound is represented by Formula II:

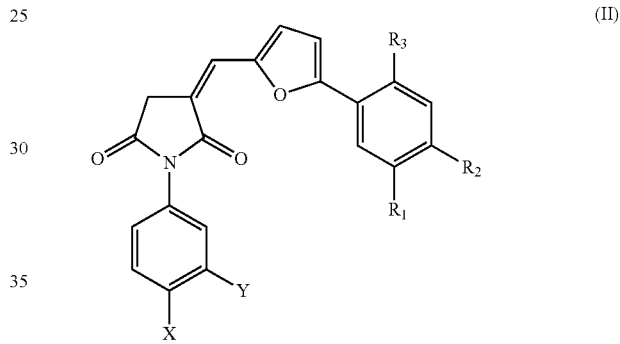

(II)

in which
X is H, C(O)-Q or S(O)$_2$-Q;
Y is H, halogen, or C(O)-Q;
$R_1$ and $R_2$ are independently H or $C_1$-$C_4$alkyl; and
$R_3$ is halogen, C(O)-Q, NO$_2$, CN, or CH$_2$OH;
Q is OH, O—$C_1$-$C_4$alkyl, —NH$_2$, or NH($C_1$-$C_4$alkyl); or a salt (e.g., a pharmaceutically acceptable salt) thereof.

In certain embodiments of Formula II, X is COOH.
In certain embodiments of Formula II, Y is H.
In certain embodiments of Formula II, $R_1$ and $R_2$ are each methyl.
In certain embodiments of Formula II, $R_3$ is COOMe.
In certain embodiments, the compound is represented by Formula III:

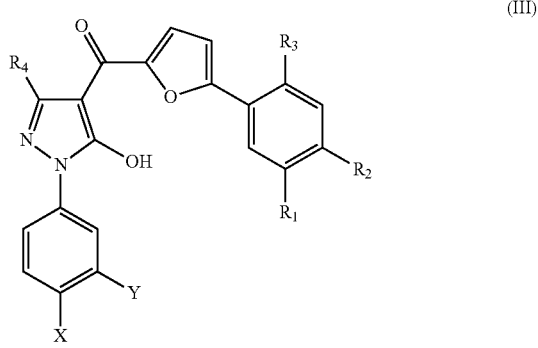

(III)

in which

X is H, C(O)-Q or S(O)$_2$-Q;

Y is H, halogen, or C(O)-Q;

R$_1$ and R$_2$ are independently H or C$_1$-C$_4$alkyl; and

R$_3$ is halogen, C(O)-Q, NO$_2$, CN, or CH$_2$OH;

R$_4$ is H or methyl;

Q is OH, O—C$_1$-C$_4$alkyl, —NH$_2$, or NH(C$_1$-C$_4$alkyl);

or a salt (e.g., a pharmaceutically acceptable salt) thereof.

In certain embodiments of Formula III, X is COOH.

In certain embodiments of Formula III, Y is H.

In certain embodiments of Formula III, R$_1$ and R$_2$ are each methyl.

In certain embodiments of Formula III, R$_3$ is NO$_2$.

In certain embodiments of Formula III, R$_4$ is methyl.

In certain embodiments, the compound is a compound disclosed herein as Compound 6b, Compound 6c, Compound 6g, Compound 6h, Compound 6i, Compound 6j, Compound 6k, Compound 6l, Compound 6m, Compound 6n, Compound 6o, Compound 6p, Compound 6q, or Compound 6r.

In certain embodiments, the compound is selected from the following compounds:

| Compound | Structure |
|----------|-----------|
| 6b | |
| 6g | |
| 6i | |
| 6j | 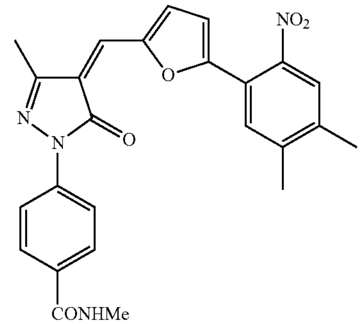 |
| 6l | 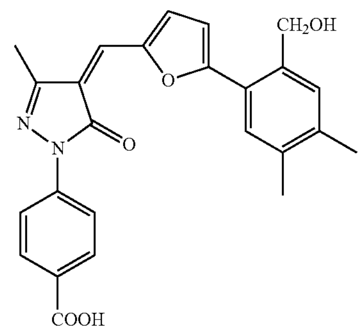 |
| 6m | 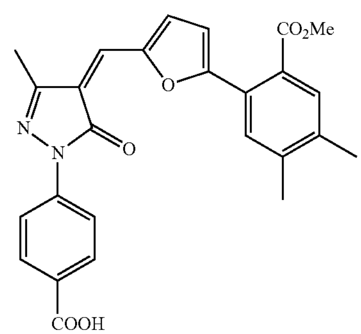 |
| 6n | 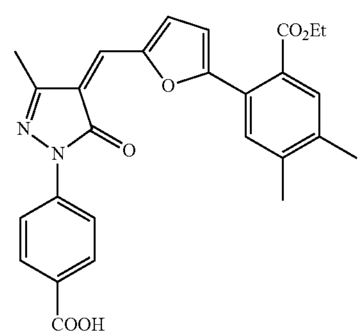 |

-continued
| Compound | Structure |
|---|---|
| 6o | 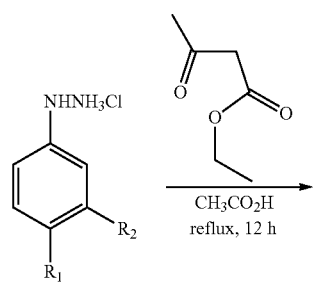 |
| 6q | 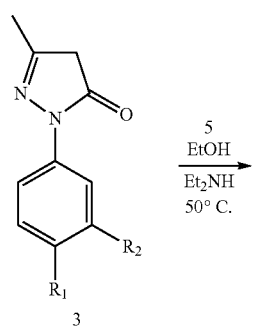 |
| 6r | 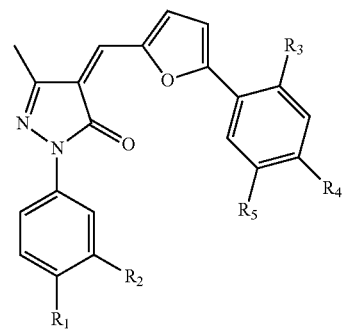 |
or a pharmaceutically acceptable salt thereof.
Methods for making and testing analogs are well-known in the art. As such, also included in the invention are analogs of the p300/CBP HAT inhibitors.
For example, analogs of C646 were synthesized as follows.
1. General Synthetic Approach
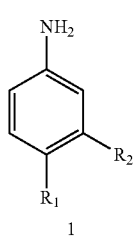
1
-continued
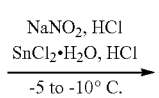
2
3
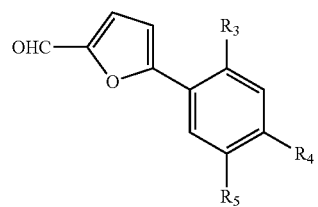
6
C646 analogs
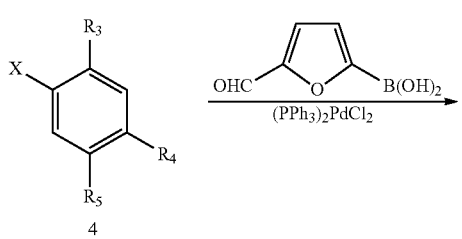
4
5

2. Synthesis of 3-methyl-1-phenyl-1H-pyrazol-5(4H)-one (3a, b, d-i)

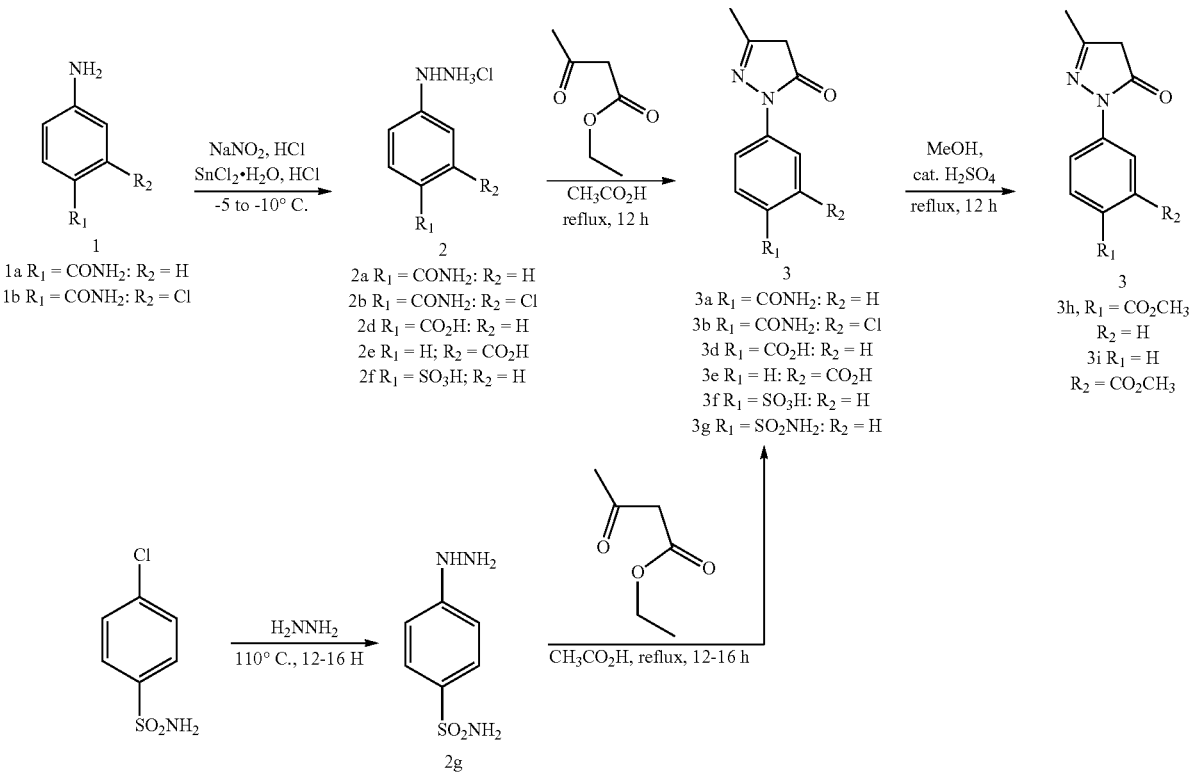

Synthesis of 3-methyl-1-phenyl-1H-pyrazol-5(4H)-one (3a, b, d-i)

3-Methyl-1-aryl-1H-pyrazol-5(4H)-ones (3a, b, d-i) were synthesized following a modified literature procedure.[1] Ethyl acetoacetate (39.3 mmol) Was added to a solution of the arylhydrazine (2, 32.8 mmol) in glacial acetic acid (30 ml). After addition, the reaction was heated at reflux With stirring for 12-16 h. Once the reaction was allowed to cool to room temperature reaction mixture was concentrated in vacuo resulting in the formation of a precipitate. The solid was filtered and washed with dichloromethane, and the crude pyrazolones were further purified by silica gel flash column chromatography eluting with a gradient oil 1-5% MeOH/DCM (DCM contains 0.5 to 1% AcOH).

3h and 3i were synthesized by esterification of pyrazolones 3d and 3e (1.44 mmol), respectively, by refluxing in anhydrous methanol (40 ml) and a catalytic amount of concentrated sulfuric acid. After heating to reflux with stirring for 12 h, the reaction mixture was allowed to cool to room temperature and was concentrated under reduced pressure. Crude products were purified by column chromatography using 0-4% MeOH/DCM as an eluent.

The arylhydrazines 2d-f were commercially available while compounds 2a[2] and 2b[3] were synthesized by diazotization followed by reduction of the diazonium salts using reaction protocols known in literature. Briefly, to a cold suspension of the corresponding aniline 1a-b (33.5 mmol) in conc. HCl (40 ml) at −5 to −10° C., an ice-cold isolation of sodium nitrite (50.2 mmol) in water (10 ml) as added and stirred cold for 30 min. A freshly prepared solution of tin(II) chloride dihydrate (100 mmol) in conc. HCl (10 ml) as added slowly with the observation of gas evolution from the reaction. The resulting mixture as stirred at −5° C. far 1-2 h. During that time a precipitate formed and was filtered, washed with water, washed with ethyl acetate, dried (in vacuo) and used for the next step without further purification. Compound 2b was purified by column chromatography using 2-8% MeOH (7 N $NH_3$)/DCM as eluent.

4-Hydrazino benezenesulfonamide 2 g was obtained from 4-chloro sulfonamide. A mixture of 4-chlorosulfonamide (2.0 g, 10.7 mmol) and hydrazine (3 ml, 94.2 mmol) was heated at 110° C. for 12 h. Water (50 ml) was added and the solid was filtered and washed with methanol to give 2g (71%) as a colorless solid.

To a solution of 2g (1.39 g, 7.4 mmol) in glacial acetic acid (20 ml) was added ethyl acetoacetate (1 ml; 8.1 mmol) in one portion. The resulting solution was heated to reflux for 16 h. As the reaction was cooled to room temperature, a precipitate formed and was filtered, washed with DCM and dried (in vacuo) to give 3g as reported in literature.[4]

4-(4,5-dihydro-3-methyl-5-oxopyrazol-1-yl)benzamide (3a) was obtained as a colorless solid (40%).[5] mp: 237-240° C., $^1$H NMR (400 MHz, DMSO-$d_6$): δ 2.06 (s, 3H), 3.30 (s, 2H), 7.29 (hrs, 1H), 7.75 (d, J=8.0 Hz, 2H), 7.87 (d, J=7.2 Hz, 2H), 7.91 (brs, 1H); HRMS (m/z): [M+H]$^+$ calcd for $C_{11}H_{12}N_3O_2$, 218.0935; found, 218.0931.

2-chloro-4-(4,5-dihydro-3-methyl-5-oxopyrazol-1-yl)benzamide (3h) was obtained as a colorless solid (60%) mp: 180-182° C.; $^1$H NMR (400 MHz, CDCl$_3$). δ 2.22 (S, 3H), 3.46 (s, 2H), 5.94 (brs, 1H) 6.53 (brs 1H), 7.93 (m, 2H), 8.07 (d, J=2.0 Hz, 1H); $^{13}$C NMR (100 MHz, CDCl$_3$). δ17.32, 43.35, 116.57, 119.46, 128.91, 132.26, 140.98, 157.46, 158.30, 167.43, 170.96; HRMS (m/z): [M+H]$^+$ calcd for $C_{11}H_{11}ClN_3O_2$, 252.0534; found, 252.0537.

4-(4,5-dihydro-3-methyl-5-oxopyrazol-1-yl)benzoic acid (3d) was obtained as a solid (73%).[6] mp: 284-286° C.; $^1$H NMR (400 MHz. DMSO-$d_6$): δ 2.12 (s, 3H), 5.38 (s, 1H), 7.88 (d, J=8.4 Hz, 2H), 7.98 (d, J=8.8 Hz, 2H), 12.86 (brs, 1H).

3-(4,5-dihydro-3-methyl-5-oxopyrazol-1-yl)benzoic acid (3e) was Obtained as a solid (40%).[7] mp: 203-205 $^1$H NMR (400 MHz, DMSO-$d_6$): δ 2.39 (s, 3H), 2.44 (brs, 1H), 5.91 (s, 1H), 7.64 (t, J=8.0 Hz, 1H) 7.88 (d=J=8.0 Hz, 1H), 8.00 (d, J=8.0 Hz, 1H), 8.30 (d, J=20 Hz, 1H), 13.23 (brs, 1H); HRMS (m/z): [M+H]⁺ calcd for $C_{11}H_{11}N_2O_3$, 219.0764; found, 219.0758.

4-(4,5-dihydro-3-methyl-5-oxopyrazol-1-yl)benzenesulfonic acid (3f) was obtained as a colorless solid (63%).[8] mp: 249-251° C.; $^1$H NMR (400 MHz, DMSO-$d_6$): δ 2.42 (s, 2H), 2.45 (s 3H), 3.65 (s, 2H), 7.43 (d, J=7.2 Hz, 2H), 7.69 (d, J=8.0 Hz, 2H), 12.44 (brs, 1H); HRMS (m/z): [M+H]⁺ calcd for $C_{10}H_9N_2O_4S$, 253.0289; found, 253.0284.

4-(4,5-dihydro-3-methyl-5-oxopyrazol-1-yl)benzenesulfonamide (3g) was obtained as a solid (59%).[9] mp: 236-238° C.; $^1$H NMR (400 MHz, DMSO-$d_6$): δ 2.10 (s, 3H), 3.73 (s, 1H), 5.37 (s, 1H), 7.33 (s, 2H) 7.83 (d, J=8.4 Hz, 2H), 7.90 (d, J=8.8 Hz, 2H); HRMS (m/z): [M–H]⁻ calcd for $C_{10}H_{10}N_3O_3S$, 252.0448; found, 252.045.

Methyl 4-(4,5-dihydro-3-methyl-5-oxopyrazol-1-yl)benzoate (3h) was obtained as a solid (44%).[16] mp: 144-146° C., $^1$H NMR (400 MHz CDCl₃): δ 2.19 (s, 3H), 3.44 (s, 2H), 3.89 (s, 3H), 7.98 (d, J=8.8 Hz, 2H), 8.04 (d, J=8.8 Hz, 2H); HRMS (m/z): [M+H]⁺ calcd for $C_{12}H_{13}N_2O_3$, 233.092; found, 233.0925.

Methyl 3-(4,5-dihydro-3-methyl-5-oxopyrazol-1-yl)benzoate (3i) was obtained as an oil (94%).[7] $^1$H NMR (400 MHz, CDCl₃): δ 2.17 (s, 3H), 3.42 (s, 2H), 3.89 (s, 3H), 7.42 (t, J=8.0 Hz, 1H) 7.81 (d, J=8.0 Hz, 1H), 8.09 (m, 1H), 8.45 (s, 1H); HRMS (m/z): [M+H]⁺ calcd for $C_{12}H_{13}N_2O_3$, 233.0921; found, 233.0918.

3. Synthesis of 3-(4,5-dihydro-3-methyl-5-oxopyrazol-1-yl)propanoic acid (3j)

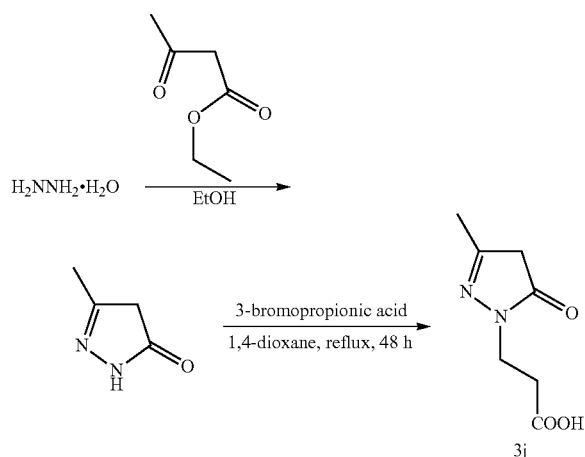

Synthesis of 3-(4,5-dihydro-3-methyl-5-oxopyrazol-1-yl)propanoic acid (3j)

To a solution of hydrazine monohydrate (5.00 g, 99.88 mmol) in ethanol (20 ml) was added ethyl acetoacetate (4.85 ml, 99.88 mmol) dropwise at room temperature. During addition, the reaction became warm to the touch. After addition was complete, the reaction mixture was stirred for 3 h at room temperature. The reaction mixture was concentrated under reduced pressure, and during concentration a precipitate formed which was filtered and dried to give 3-methyl-pyrazol-5-one 3j in 94% yield. mp: 214-216° C. (Lit, mp: 218° C.)[11]; $^1$H NMR (DMSO-$d_6$): δ 2.06 (s, 3H), 5.20 (s, 1H); 10.34 (hrs, 1H); HRMS (m/z): [M+H]⁺ calcd for $C_4H_6N_2O$, 98.0480; found, 99.1.

To a solution of 3-methyl-pyrazol-5-one (5.7 g, 58.0 mmol) in anhydrous 1,4-dioxane was added 3-bromopropionic acid, and the resulting mixture was heated to reflux for 48 h.[12] The reaction mixture was concentrated under reduced pressure, and the crude product was purified by column chromotography using 5-10% MeOH/DCM as an eluent to give 3j (22%) as a solid.[13] mp: 210-215° C. (Lit. mp 178-180° C.); $^1$H NMR (400 MHz, CDCl₃): δ 2.21 (s, 3H), 2.76 (m, 2H), 3.14 (s, 2H), 4.14 (m, 2H), 8.01 (brs, 1H); HRMS (m/z): [M–H]⁻ calcd for $C_7H_4N_2O_3$, 169.0619; found, 169.0622.

4. Synthesis of 4-(2,5-dioxo-2H-pyrrol-1(5H)-yl) benzoic acid (3k)

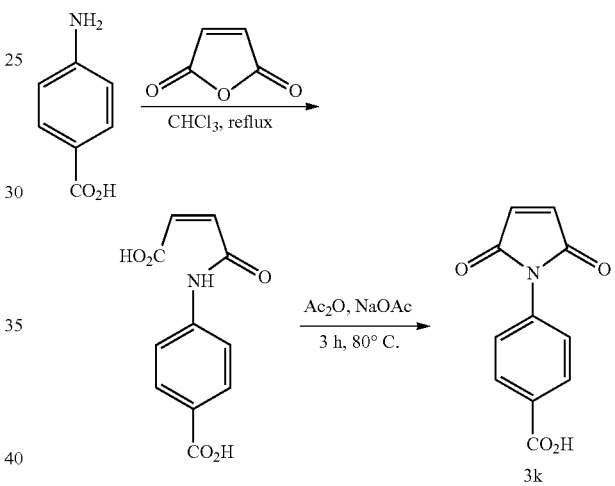

Synthesis of 4-(2,5-dioxo-2H-pyrrol-1(5H)-benzoic acid (3k)

To a mixture of maleic anhydride (5.0 g. 50.9 mmol) in chloroform (100 ml) was added p-aminophenyl maleamic acid (6.99 g, 50.9 mmol). The resulting mixture was heated to reflux for 3 h. The solution was then cooled and a precipitate formed. The precipitate was filtered, washed with ethyl acetate and dried, to give 2N-(4-carboxyphenyl)maleamic acid (99%) as a solid.[14] mp: 218-220° C. $^1$H NMR (DMSO-$d_6$): δ 6.30 (d, J=12.0 Hz, 1H), 6.47 (d, J=1.20 Hz, 1H), 7.71 (d, J=8.4 Hz, 2H), 7.88 (d, J=8.8 Hz, 2H), 10.59 (s, 1H), 12.83 (brs, 1H); HRMS (m/z): [M–H]⁻ calcd for $C_{11}H_8NO_5$, 234.0408; found, 234.0406.

A mixture of N-(4-carboxyphenyl)maleamic acid (5.0 g, 21.2 mmol), acetic anhydride (4 ml, 42.5 mmol) and sodium acetate (3.48 g, 42.5 mmol) Was heated at 80° C. for 3h. After heating, excess acetic anhydride was removed under reduced pressure and the residue purified by column chromatography using 0-4%. MeOH/DCM as an eluent to give 3k (33%) as a solid.[15] mp: 165-168° C.; $^1$H NMR (400 MHz, DMSO-$d_6$): δ 7.20 (s, 2H), 7.47 (d, J=8.4 Hz, 2H), 8.02 (d, 8.0 Hz, 2H), 12.75 (brs, 1H); HRMS (m/z): [M–H]⁻ calcd for $C_{11}H_6NO_4$, 216.0302; found, 216.0296.

5. Synthesis of 5-aryl/heteroaryl-furan-2-aldehyde (5a, 5b, 5d, 5e, 5g, 5h)

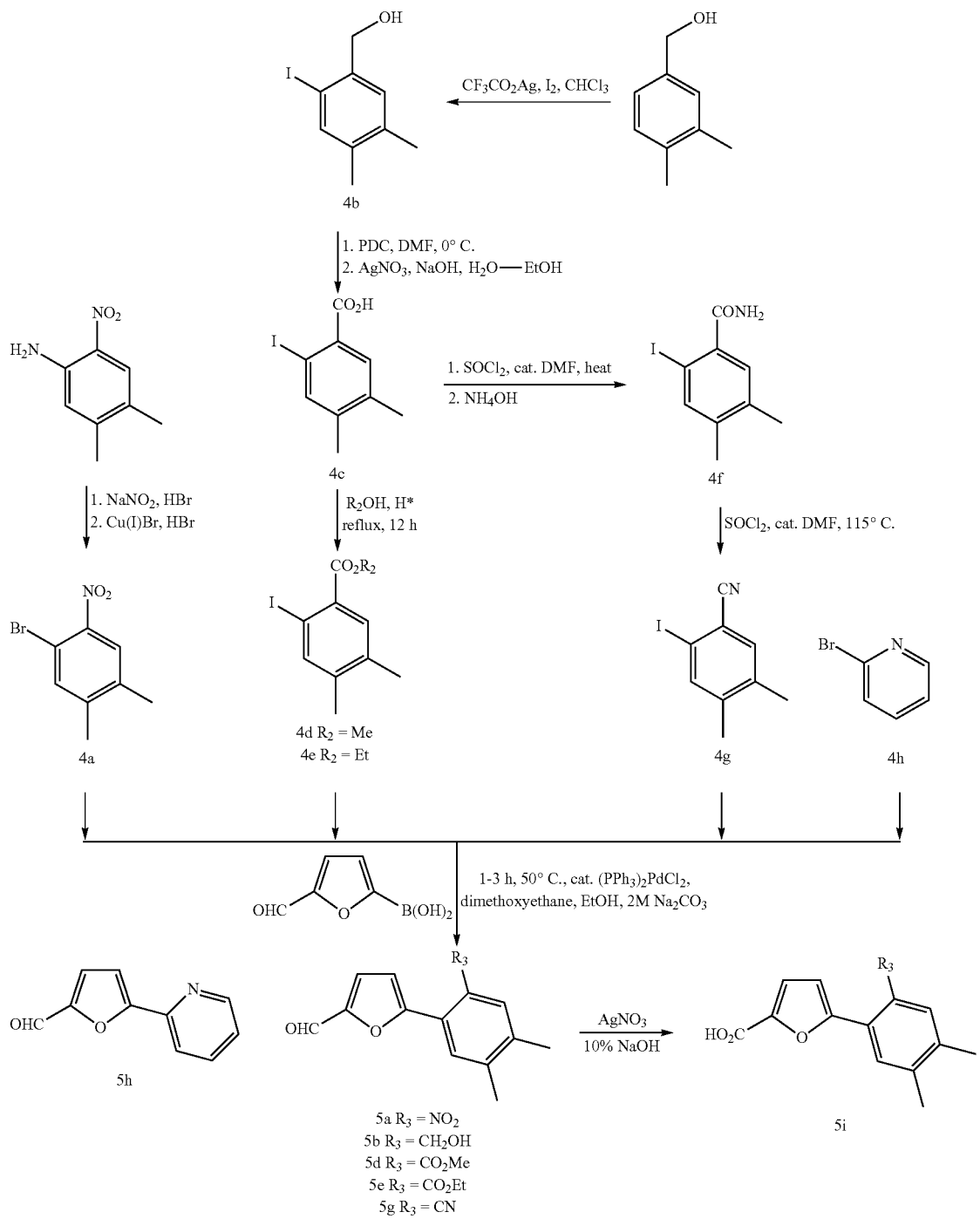

Synthesis of 5-aryl/heteroaryl-furan-2-aldehyde (5a, 5h, 5d, 5c, 5g, 5h)

1-Bromo-4,5-dimethyl-2-nitrobenzene 4a was obtained from 4,5-dimethyl-2-nitroaniline via the Sandmeyer reaction following a literature procedure.[16] 4,5-dimethyl-2-hydroxymethyl iodoenzene 4b was obtained in 91% yield from 3,4-dimethylbenzyl alcohol using silver trifluoroacetate and iodine in chloroform following a literature procedure.[17] 4c was obtained from 4b using a two-step oxidation with pyridinium dichromate in dimethylformamide followed by a mixture of silver nitrate and sodium hydroxide in water ethanol.[17] The methyl ester 4d and ethyl ester 4e were obtained by dissolving 4,5-dimethyl-2-iodobenzoic acid 4c in either anhydrous methanol or anhydrous ethanol followed by heating to reflux in the presence of catalytic sulfuric acid. Upon completion of the reaction, the mixture was concentrated, and the crude product purified by column chromatography using 5-40% EtOAc/hexane as an eluent.

Methyl (4,5-dimethyl-2-iodo)benzoate (4d) was obtained as an oil (90%). $^1$H NMR (400 MHz, CDCl$_3$): δ 2.22 and 2.23 (2s, 6H), 3.89 (s, 3H), 7.61 (s, 1H), 7.76 (s, 1H); $^{13}$C NMR (100 MHz, CDCl$_3$): δ 19.54 (2C), 52.50, 91.06, 132.00, 132.49, 136.98, 142.43, 142.84, 166.97; HRMS (m/z): [M+H]$^+$ calcd for C$_{19}$H$_{12}$O$_2$I, 299.9877; found, 290.9884.

Ethyl 2-iodo-4,5-dimethylbenzoate (4e) was obtained as an oil (37%). $^1$H NMR (400 MHz, CDCl$_3$): δ 1.40 (t, J=8.0 Hz, 3H), 2.23 (s, 6H), 4.37 (q, J=6.4 Hz, 2H), 7.60 (s, 1H), 7.75 (s, 1H); $^{13}$C NMR (100 MHz, CDCl$_3$): δ 14.52, 19.52 (2C), 61.66, 90.62, 132.35, 132.43, 136.95, 142.33, 142.62, 166.62; HRMS (m/z): [M+H]$^+$ calcd for C$_{11}$H$_{14}$IO$_2$, 305.0033; found, 305.0041.

4,5-Dimethyl-2-iodobenzamide (4f) was obtained from 4,5-dimethyl-2-iodobenzoic acid 4c in two steps. To a solution of 2-iodo-4,5-dimethylbenzo ic acid 4c (1.2 g, 4.34 mmol) in thionyl chloride (20 ml) was added a catalytic amount of DMF, and the resulting solution was heated to redox for 2-3 hours. Excess thionyl chloride was removed under reduced pressure, and the crude acid chloride was dissolved in dry THF (10 ml) and transferred to a pressure vessel. After the addition of 38% aqueous ammonium hydroxide (20 ml), the pressure vessel was sealed and the reaction stirred at room temperature for 12 h. The reaction mixture was then concentrated and diluted with water (75 ml). The product was filtered and washed with water followed by washing with hexanes, and drying (in vacuo) to give the amide 4f (75%) as solid. mp 195-197° C., $^1$H NMR (400 MHz, DMSO-d$_6$): δ 2.15 and 2.16 (2s, 6H), 7.11 (s, 1H), 7.40 (s, 1H), 7.61 (s, 1H), 7.70 (s, 1H); $^{13}$C NMR (100 MHz, DMSO-d$_6$): δ 19.23, 19.48, 90.12, 129.62, 136.92, 140.18, 140.26, 140.91, 171.25; HRMS (m/z): [M+H]$^+$ calcd for C$_9$H$_{11}$INO, C$_9$H$_{11}$INO, 275.9880; found, 275.9878.

4,5-Dimethyl-2-iodobenzonitrile (4g) was obtained from 4f using thionyl chloride in DMF as reported.[18] To a solution of amide (1.0 g 3.63 mmol) in DMF (20 ml) was added thionyl chloride (1.5 ml, 18.1 mmol) dropwise. Upon complete addition, the resulting solution was heated at 115° C. for 2 h. Once the reaction was complete, the mixture was allowed to cool to room temperature, poured on ice and extracted with ethyl acetate (3×50 ml). The organic layer was dried over anhydrous MgSO$_4$, concentrated, and the crude product purified by column chromatography using 9-40% EtOAC/hexane as an eluent to give 4g (55%) as a solid. $^1$H NMR (400 MHz, CDCl$_3$): δ 2.23 (s, 3H), 2.27 (s, 3H), 7.34 (s, 1H), 7.66 (s, 1H); HRMS (m/z): [M+H]$^+$ calcd for C$_9$H$_9$NI, 257.9774; found, 257.9781.

5-Aryl/heteroaryl-2-furaldehydes 5a, 5h, 5d, 5e, 5g, 5h were synthesized by heating a mixture of 5-formyl-2-furanboronic acid (1.0 mmol), the corresponding aryl/heteroaryl halides 4a, 4b, 4d, 4e, 4g, 4h (1.0 mmol), and bis(triphenylphosphine)palladium(II)chloride (0.05 mmol) in dimethoxyethane:2M sodium carbonate (1:1) and ethanol heated to 50° C. according to a literature method.[19] The crude products were purified by column chromatography using 10-60% EtOAc/hexane as an eluent.

5-(4,5-dimethyl-2-nitrophenyl)furan-2-aldehyde (5a) was obtained as a yellow solid (86%). mp: 94-95° C.; $^1$H NMR (400 MHz, CDCl$_3$): δ 2.37 (s, 6H), 6.73 (d, J=4.0 Hz, 1H); 7.30 (d, J=4.0 Hz, 1H), 7.56 (s, 1H); 7.65 (s, 1H), 9.65 (s, 1H); $^{13}$C NMR (100 MHz, CDCl$_3$): δ 19.92, 19.99, 111.96, 120.84, 122.58, 125.70, 131.27, 140.13, 142.66, 146.05, 152.82, 154.40, 177.88; HRMS (m/z): [M+H]$^+$ calcd for C$_{13}$H$_{12}$NO$_4$, 246.0761; found, 246.0764.

5-(2-(hydroxymethyl)-4,5-dimethylphenyl)furan-2-aldehyde (5b) was obtained as a (68%) brown oil. $^1$H NMR (400 MHz, CDCl$_3$): δ 2.25 and 2.26 (2s, 6H), 4.72 (s, 2H), 6.86 (d, J=3.2 MHz, 1H), 7.25 (s, 1H) 7.29 (d, J=3.6 Hz, 1H), 7.53 (s, 1H), 9.56 (s, 1H); $^{13}$C NMR (400 MHz, CDCl$_3$): δ 19.58, 19.87, 63.65, 111.03, 125.52, 129.70, 131.54, 135.85, 136.86, 139.14, 151.99, 159.37, 177.39; HRMS (m/z): [M+H]$^+$ calcd for C$_{14}$H$_{15}$O$_3$, 231.1016; found, 231.1018.

Methyl 2-(5-formylfuran-2-yl)-4,5-dimethylbenzoate (5d) was obtained as a colorless solid (84%). mp: 81-82° C.; $^1$H NMR (400 MHz, CDCl$_3$): δ2.31 and 2.32 (2s, 6H), 3.82 (s, 3H), 6.68 (d, J=4.0 Hz, 1H), 7.29 (d, J=3.2 Hz, 1H), 7.45 (s, 1H), 7.56 (s, 1H), 9.61 (s, 1H); $^{13}$C NMR (100 MHz, CDCl$_3$): δ 19.80, 19.96, 5267, 110.79, 123.19, 126.39, 128.26, 130.66, 131.33, 138.88, 140.81, 152.35, 158.71, 168.66, 177.55; HRMS (m/z): [M]$^+$ calcd for C$_{15}$H$_{15}$O$_4$, 259.0971; found 259.0965.

Ethyl 2-(5-formylfuran-2-yl)-4,5-dimethylbenzoate (5e) Was obtained as a (39%) solid. mp: 68-69° C. $^1$H NMR (400 MHz, CDCl$_3$): δ 1.22 (m, 3H), 2.31 (s, 6H), 4.26 (m, 2H), 6.66 (d, J=4.0 Hz, 1H), 7.29 (d, J=3.6 Hz, 1H), 7.42 (s, 1H), 7.56 (s, 1H), 9.61 (s, 1H); $^{13}$C NMR (100 MHz, CDCl$_3$): δ 14.32, 19.79; 19.94, 61.62, 110.77, 126.42, 128.70, 130.80, 131.39, 138.88, 140.72, 152.35, 159.02, 168.20, 177.58; HRMS (m/z): [M+H]$^+$ calcd for C$_{16}$H$_{17}$O$_4$, 273.1121; found 273.1122.

2-(5-formylfuran-2-yl)-4,5-dimethylbenzonitrile (5g) was obtained as a colorless solid (69%). mp: 169-171° C.; $^1$H NMR, (400 MHz, CDCl$_3$); δ 2.32 (s, 3H), 2.38 (s, 3H), 7.35 (d, J=4.0 Hz; 1H), 7.43 (d, J=4.0 Hz, 1H), 7.50 (s, 1H), 7.85 (s, 1H), 9.69 (s, 1H); $^{13}$C NMR (100 MHz, CDCl$_3$): δ 19.66, 20.37, 105.98, 111.88, 118.93, 123.59, 128.53, 129.17, 135.23, 139.17, 143.48, 152.18, 155.19, 177.70; HRMS (m/z): [M+H]$^+$ calcd for C$_{14}$H$_{12}$NO$_2$. 226.0863; found, 226.0865.

5-(pyridin-2-yl)furan-2-aldehyde (5h) was obtained as a yellow solid (74%).[20] mp: 63-65° C.; $^1$H NMR (400 MHz, DMSO-d$_6$) δ: 7.35 (d, J=4.0 Hz, 1H), 7.42 (m, 1H), 7.66 (d, J=4.0 Hz, 1H), 7.91 (m, 3H), 8.65 (m, 1H), 9.65 (s, 1H); $^{13}$C NMR (100 MHz, CDCl$_3$): δ 110.95, 120.42, 123.42, 124.12, 137.24, 148.04, 150.25, 152.80, 158.59, 178.01; HRMS (m/z): [M+H]$^+$ calcd for C$_{10}$H$_8$NO$_2$, 174.0550; found, 174.0545.

Synthesis of 5-(4,5-dimethyl-2-nitrophenyl)furan-2-carboxylic acid (5i). To 5-(4,5-dimethyl-2-nitrophenyl)furan-2-aldehyde (5a) (0.69 g, 2.81 mmol) was added solid NaOH (0.12 g, 3.09 mmol) and 10% NaOH solution (6.2 ml). Silver nitrate (0.47 g, 2.81 mmol) was added, and the reaction mixture heated to 60° C. for 3 h. After cooling to room temperature the resulting mixture was poured into 2N HCl (50 ml) during which the product precipitated out of solution and was collected by filtration. The crude solid was purified by column chromatography using 0-2% MeOH/DCM as eluent. (5i) was obtained yellow solid (41%). mp 231-233° C. $^1$H NMR (400 MHz, DMSO-d$_6$): δ 2.34 and 2.35 (6H, 2s), 6.93 and 6.94 (dd, J=1.6 and 3.6 Hz, 1H), 7.31 and 7.32 (dd, J=1.2 and 3.2 Hz, 1H) 7.63 (s, 1H), 7.80 (s, 1H) 13.20 (brs, 1H); $^{13}$C NMR (100 MHz, DMSO-d$_6$): δ 19.63, 19.84, 111.67, 120.01, 120.63, 125.62, 131.19, 140.48, 143.26, 145.82, 145.91, 152.59, 159.71; HRMS (m/z): [M+H]$^+$ calcd for C$_{13}$H$_{12}$NO$_5$, 262.0710; found, 262.0714.

6. Synthesis of 6a, 6b, and 6d-6p
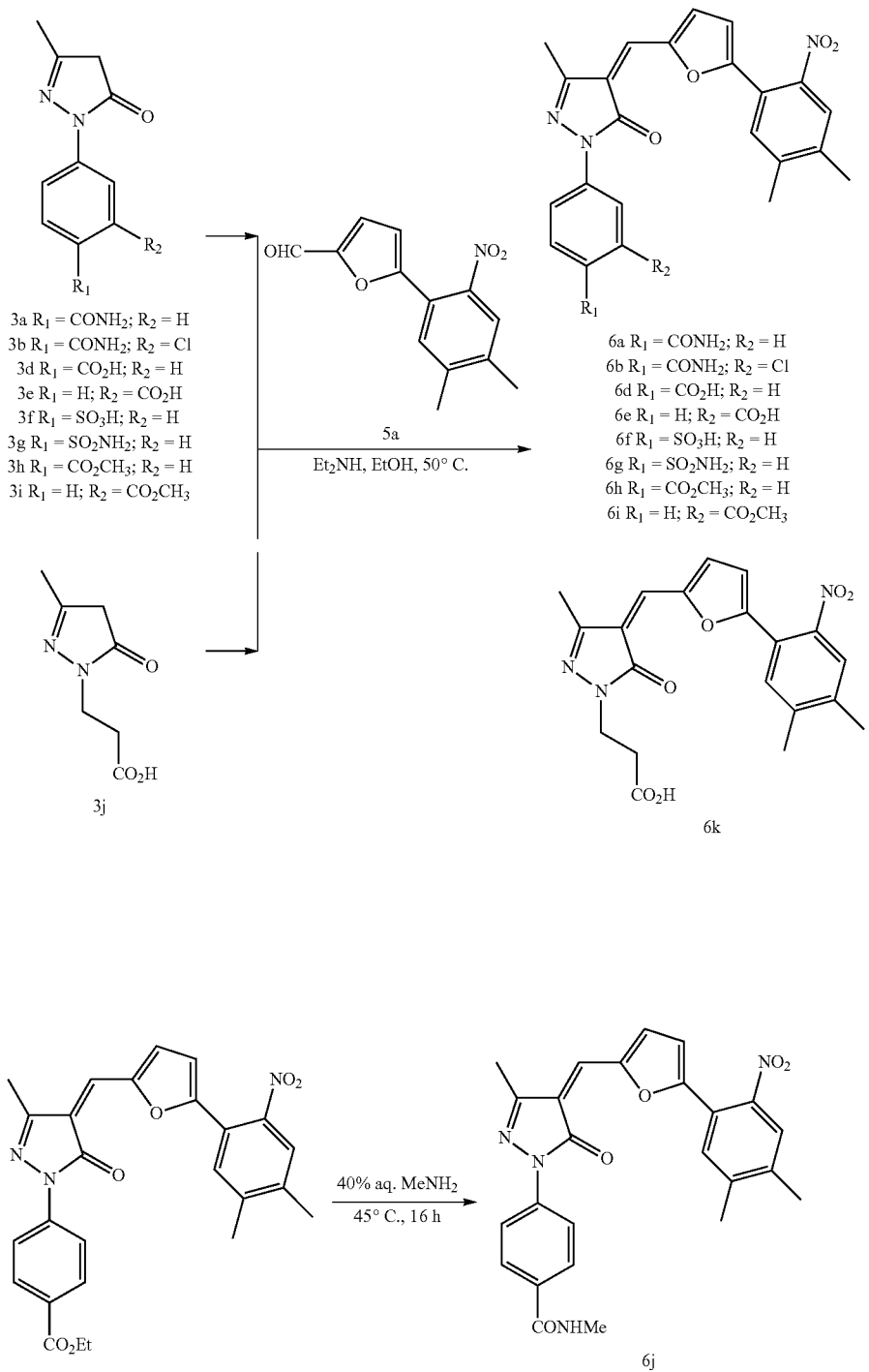

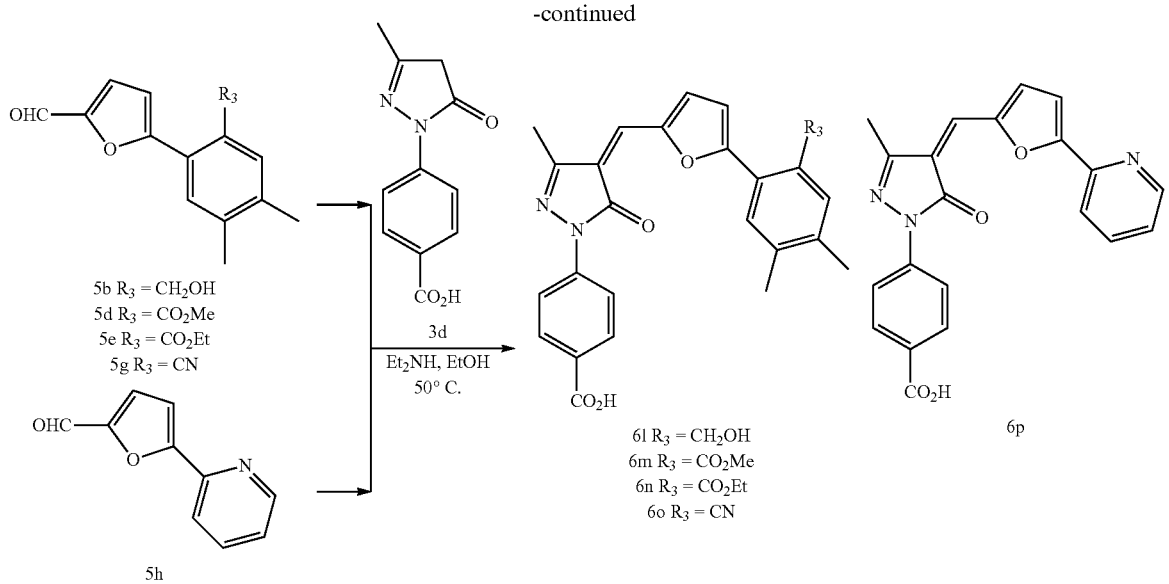

Synthesis of 1-Aryl-3-methyl-4-[[5-aryl/heteroaryl-2-furanyl]methylene]-pyrazol-5-one (6a-p)

Compounds 6a-p were synthesized following a modified literature procedure.[22] An equimolar solution of 1-aryl-3-methyl-pyrazol-5-one, 5-aryl-2-furaldehyde and diethylamine in ethanol was stirred at 50° C. for 1-3 h. Upon cooling the product precipitated and was collected by filtration and further purified by column chromatography using 3-8% MeOH/DCM as an eluent (DCM contains 0.5-1.0%, AcOH).

4-(4,5-dihydro-3-methyl-4-((5-(4,5-dimethyl-2-nitrophenyl)furan-2-yl)methylene)-5-oxopyrazol-1-yl)benzamide (6a) as obtained as a red solid (40%). mp: 273-275° C.; $^1$H NMR (400 MHz, DMSO-$d_6$): δ 2.24, 2.27 and 2.30 (3s, 9H), 7.11 (d, J=4.0 Hz, 1H), 7.32 (brs, 1H), 7.41 (s, 1H), 7.62 (s, 1H), 7.74 (s, 1H), 7.91 (m, 5H), 8.58 (d, J=4.0 Hz, 1H); $^{13}$C NMR (100 MHz, DMSO-$d_6$): δ 13.46, 19.66, 19.87, 114.69, 117.23, 117.40, 119.81, 122.23, 125.76, 127.14, 129.07, 129.78, 130.27, 131.00, 140.99, 143.21, 145.58, 151.20, 151.81, 155.29, 162.26, 167.97; HRMS (m/z): [M+H]$^+$ calcd for $C_{24}H_{21}N_4O_5$, 445.1506; found, 445.1507.

4-(4,5-dihydro-3-methyl-4-((5-(4,5-dimethyl-2-nitrophenyl)furan-2-yl)methylene)-5-oxopyrazol-1-yl)-2-chlorobenzamide (6b) was obtained as a red solid (35%). mp: 267-269° C.; $^1$H NMR (400 MHz, DMSO-$d_6$): δ 2.30 (s, 3H), 2.34 and 2.35 (2s, 6H), 7.21 (d, J=4.0 Hz, 1H), 7.54 (m, 3H), 7.75 (s, 1H), 7.83 (s, 2H), 7.89 (d, J=8.8 Hz, 1H), 8.04 (s, 1H), 8.65 (d, J=4.0 Hz, 1H); $^{13}$C NMR (100 MHz, DMSO-$d_6$): δ 12.74, 18.94, 19.08, 114.07, 115.56, 117.85, 119.27, 121.38, 125.12, 126.71, 129.56, 129.71, 130.29, 130.57, 132.15, 139.38, 140.46, 142.63, 145.05, 150.54, 151.64, 154.92, 161.73, 167.54; HRMS (m/z): [M+H]$^+$ calcd for $C_{24}H_{20}N_4O_5Cl$, 479.1117; found, 479.1114.

4-(4,5-dihydro-3-methyl-4-((5-(4,5-dimethyl-2-nitrophenyl)furan-2-yl)methylene)-5-oxopyrazol-1-yl)benzoic acid (6d) was obtained as a red solid (56%), mp: 224-226° C.; $^1$H NMR (400 MHz, DMSO-$d_6$) δ 2.30, 2.32 and 2.33 (3s, 9H), 7.18 (d, J=4.0 Hz, 1H); 7.51 (s, 1H), 7.71 (s 1H), 7.81 (s, 1H), 7.97 (d, J=8.8 Hz, 2H), 8.03 (d, J=8.4 Hz, 2H); 8.64 (d, J=4.0 Hz, 1H); 12.79 (brs, 1H); $^{13}$C NMR (100 MHz, DMSO-$d_6$): δ 18.71, 24.91, 25.08, 119.98, 122.69, 122.86, 125.18, 127.48, 131.05, 132.03, 132.47, 135.26, 136.25, 136.33, 136.39, 146.32, 147.53, 148.49, 150.99, 156.50, 157.38, 160.67, 167.73, 172.73; HRMS (m/z): [M+H]$^+$ calcd for $C_{24}H_{20}N_{20}N_3O_6$, 446.1347; found, 446.1344.

3-(4,5-dihydro-3-methyl-4-((5-(4,5-dimethyl-2-nitrophenyl)furan-2-yl)methylene)-5-oxopyrazol-1-yl)benzoic acid (6e) was obtained as a red solid (64%). mp: 260-262° C.; $^1$H NMR (400 MHz, DMSO-$d_6$): δ 2.33, 2.34 and 2.36 (3s, 9H), 7.22 (d, J=4.0 Hz, 1H), 7.54 (m, 2H), 7.75 (m, 2H), 7.84 (s, 1H), 8.15 (d, J=8.4 Hz, 1H), 8.54 (s, 1H), 8.71 (d, J=4.0 Hz, 1H), 13.12 (brs, 1H); $^{13}$C NMR (100 MHz, DMSO-$d_6$): δ 13.44, 19.68, 19.81; 114.74, 119.36, 120.11, 122.48, 122.63, 125.76, 125.83, 127.10, 129.77, 130.00, 131.31, 132.59, 139.11, 141.10, 143.32, 145.88, 151.34, 151.71, 155.38, 162.37, 167.82; HRMS (m/z): [M+H]$^+$ calcd for $C_2H_{20}N_3O_6$, 446.1347; found, 446.1349.

4-(4,5-dihydro-3-methyl-4-((5-(4,5-dimethyl-2-nitrophenyl)furan-2-methylene)-5-oxopyrazol-1-yl)benzenesulfonic acid (6f) was obtained as a red solid (58%), mp: 210-213° C.; $^1$H NMR (400 MHz, DMSO-$d_6$): δ 2.31, 2.33 and 2.35 (3s, 9H), 6.93 (m, 1H), 7.20 (m, 1H), 7.50 (m, 1H), 7.67 (m, 2H), 7.76 (s 1H), 7.84 (s, 1H), 7.90 (d, 1H), 8.23 (s, 1H), 10.58 (s, 1H): $^{13}$C NMR (100 MHz, DMSO-$d_6$) δ 13.50, 19.72, 19.89, 114.74, 117.33, 117.58, 120.00, 122.60, 125.85, 126.96, 127.01, 129.89, 131.25, 138.89, 141.13, 143.42, 144.73, 151.36, 151.60, 155.35, 162.20; HRMS (m/z): [M+H]$^+$ calcd for $C_{23}H_{20}N_3O_7S$, 482.1016; found, 482.1021.

4-(4,5-dihydro-3-methyl-4-((5-(4,5-dimethyl-2-nitrophenyl)furan-2-yl)methylene)-5-oxopyrazol-1-yl)benzenesulfonic acid (6g) was obtained as a red solid (89%). mp: 152-154° C. $^1$H NMR (400 MHz, DMSO-$d_6$): δ 2.29, 2.30 and 2.32 (3s, 9H), 7.19 (d, J=4.0 Hz, 1H), 7.34 (s, 2H), 7.54 (s, 1H), 7.72 (s, 1H), 7.81 (s, 1H), 7.87 (d, J=9.2 Hz, 2H), 8.09 (d, J=8.4 Hz, 2H), 8.64 (d, J=4.0 Hz, 1H); $^{13}$C NMR (100 MHz, DMSO-$d_6$): δ 12.72, 18.91, 19.05, 114.02, 117.06, 117.25, 119.25, 121.44, 125.09, 126.55, 126.69, 126.75, 129.60, 130.54, 139.30, 140.43, 140.49, 142.61, 145.03, 150.54, 151.59, 154.84, 161.79; HRMS (m/z): [M+H]$^+$ calcd for $C_{23}H_{21}N_4O_6S$, 481.1176; found, 481.1171.

Methyl 4-(4,5-dihydro-3-methyl-4-((5-(4,5-dimethyl-2-nitrophenyl)furan-2-yl)methylene)-5-oxopyrazol-1-yl)benzoate (6h) as obtained as a red solid (43%). mp 214-216° C., $^1$H NMR (400 MHz, DMSO-$d_6$): δ 2.34 (s, 3H), 2.38 and 2.39 (2s, 6H), 3.91, (s, 3H), 6.91 (d, J=4.0 Hz, 1H), 7.27 (s, 1H), 7.52 (s, 1H), 7.64 (s, 1H) 8.10 (m, 4H), 8.81 (d, J=4.0 Hz, 1H); $^{13}$C NMR (100 MHz, CDCl$_3$): δ 13.71, 20.31, 20.42, 52.59, 114.58, 118.12, 118.27, 121.25, 123.20, 126.24, 126.42, 127.56, 129.32, 131.25, 131.40, 140.53, 142.90, 143.00, 151.31, 151.69, 155.74, 163.04, 167.43; HRMS (m/z): [M+H]$^+$ calcd for C$_{25}$H$_{22}$N$_3$O$_6$, 460.1503; found, 460.1496.

Methyl 3-(4,5-dihydro-3-methyl-4-((5-(4,5-dimethyl-2-nitrophenyl)furan-2-yl)methylene)-5-oxopyrazol-1-yl)benzoate (6i) was obtained as a red solid (75%). mp: 205-207° C.; $^1$H NMR (400 MHz, CDCl$_3$): δ 2.39 (s, 6H), 2.48 (s, 3H), 3.91 (s, 3H), 6.80 (s, 1H), 7.21 (s, 1H), 7.43 (m, 3H), 7.74 (s, 1H), 7.82, (d, J=7.2 Hz, 1H), 8.22 (d, J=7.6 Hz, 1H), 8.57 (s, 1H); $^{13}$C NMR (100 MHz, CDCl$_3$): δ 17.70, 19.98, 20.15, 52.44, 113.56, 119.63, 121.29, 121.76, 122.98, 123.19, 125.85, 126.26, 127.06, 127.56, 129.16, 131.06, 131.68, 138.73, 140.49, 143.16, 148.47, 150.78, 156.34, 165.24, 167.09; HRMS (m/z): [M+H]$^+$ calcd for C$_{25}$H$_{22}$N$_3$O$_6$, 360.1503; found, 460.1501.

4-(4,5-dihydro-3-methyl-4-((5-(4,5-diethyl-2-nitrophenyl)furan-2-yl)methylene)-5-oxapyrazol-1-yl)-N-methyl-benzamide (6j) Was obtained as and solid (30%). mp: 250-253° C.; $^1$H NMR (400 MHz, CDCl$_3$): δ 2.32 (s, 1H), 2.36 and 2.37 (1s, 6H), 3.00 (d, J=4.0 Hz, 1H), 6.13 (brs, 1H), 6.90 (d, J=4.0 Hz, 1H), 7.24 (s, 1H), 7.51 (s, 1H), 7.63 (s, 1H), 7.80 (d, J=8.4 Hz, 2H), 8.08 (d, J=8.8 Hz, 2H), 8.80 (d, J=4.0 Hz, 1H); $^{13}$C NMR (100 MHz, DMSO-d$_6$): δ 12.69, 18.89, 19.05, 26.07, 113.94, 116.90, 119.25, 121.66, 125.06, 126.35, 127.83, 129.26, 129.98, 130.48, 140.12, 140.34, 142.56, 145.00, 150.53, 151.17, 154.65, 161.63, 165.87; HRMS (m/z): [M+H]$^+$ calcd for C$_{25}$H$_{23}$N$_4$O$_5$, 459.1663; found, 459.1659.

3-(4,5-dihydro-3-methyl-4-((5-(4,5-dimethyl-2-nitrophenyl)furan-2-yl)methylene)-5-oxopyrazol-1-yl)propanoic acid (6k) was obtained as a red solid (39%), mp: 189-190° C.; $^1$H NMR (400 MHz, DMSO-d$_6$): δ 2.17 (s, 3H), 2.35 (s, 6H), 2.59 (m, 2H), 3.85 (m, 2H), 7.16 (d, J=4.0 Hz, 1H), 7.40 (s, 1H), 7.73 (s, 1H), 7.82 (s, 1H), 8.67 (d, J=4.0 Hz, 1H), 12.30 (brs, 1H); $^{13}$C NMR (100 MHz, DMSO-d$_6$): δ 12.48, 18.89, 19.05, 32.95, 41.22, 113.54, 119.37, 12.18, 124.97, 127.83, 128.09, 130.39, 140.11, 142.53, 144.96, 148.14, 150.67, 153.79, 162.08, 172.26; HRMS (m/z): [M+H]$^+$ calcd for C$_{20}$H$_{20}$N$_3$O$_6$, 398.1352; found 398.1346.

4-(4,5-dihydro-4-((5-(2-(hydroxymethyl)-4,5-dimethylphenyl)-furan-2-yl)methylene)-3-methyl-5-oxopyrazol-1-yl)benzoic acid (6l) was obtained as a red solid (68%). mp: 209-211° C.; $^1$H NMR (400 MHz, DMSO-d$_6$): δ 2.27 (s, 6H), 2.33 (s, 3H), 4.68 (s, 2H), 5.30 (brs, 1H), 7.24 (d, J=4.0 Hz, 1H), 7.38 (s, 1H), 7.68 (s, 1H), 7.72 (s, 1H), 7.98 (d, J=8.4 Hz, 2H), 8.07 (d, J=8.4 Hz, 2H), 8.70 (s, 1H), 12.64 (brs, 1H); $^{13}$C NMR (100 MHz, DMSO-d$_6$): δ 12.73, 18.77, 19.26, 61.22, 113.82, 116.83, 19.70, 124.02, 125.84, 127.63, 128.42, 129.65, 129.99, 130.32, 135.22, 137.23, 138.25, 141.75, 149.49, 151.43, 159.57, 161.97, 166.75; HRMS (m/z): [M+H]$^+$ calcd for C$_{25}$H$_{23}$N$_2$O$_5$, 431.1601; found, 431.1602.

4-(4,5-dihydro-4-((5-(4,5-dimethyl-2-methylbenzoate)furan-2-yl)methylene)-3-methyl-5-oxapyrazol-1-yl)benzoic acid (6m) was obtained as a red solid (32%). mp: 254-256° C. $^1$H NMR (400 MHz, DMSO-d$_6$): δ2.28 (s, 3H), 2.30 and 2.31 (2s, 6H), 3.78 (s, 3H), 7.12 (d, J=4.0 Hz, 1H), 7.52 (s, 1H), 7.59 (s, 1H), 7.64 (s, 1H), 7.98 (d, J=8.4 Hz, 2H), 8.06 (d, J=8.4 Hz, 2H), 8.68, (d, J=4.0 Hz, 1H), (brs, 1H); $^{13}$C NMR, (100 MHz, DMSO-d$_6$): δ 12.72, 18.95, 19.12, 51.32, 113.31, 116.74, 116.95, 120.47, 124.93, 125.99, 127.72, 129.62, 129.70, 130.32, 130.39, 138.86, 140.45, 141.68, 150.00, 151.55, 158.78, 161.95, 166.73, 167.96; HRMS (m/z): [M+H]$^+$ calcd for C$_{26}$H$_{23}$N$_2$O$_6$, 459.1551; found, 459.1560.

4-(4,5-dihydro-4-((5-(4,5-dimethyl-2-ethylbenzoate)furan-2-yl)methylene)-3-methyl-5-oxopyrazol-1-yl)benzoic acid (6n) was obtained as a red solid (41%) mp: 241-243° C., $^1$H NMR (400 MHz, DMSO-d$_6$): δ 1.14 (t, J=7.6 Hz, 3H), 2.29 and 2.30 (2s, 9H), 4.23 (q, J=7.2 Hz, 2H), 7.12 (d, J=4.0 Hz, 2H), 7.52 (s, 1H), 7.60 and 7.62 (2s, 2H); 7.98 (d, J=8.4 Hz, 2H), 8.06 (d, J=8.4 Hz, 2H), 8.69 (d, J=4.0 Hz, 1H), 12.81 (brs, 1H); $^{13}$C NMR (100 MHz, DMSO-d$_6$): δ 12.67, 13.85, 18.94, 19.10, 61.02, 113.27, 116.91, 120.37, 124.98, 128.09, 129.56, 129.79, 130.29, 130.36, 130.41, 131.04, 138.82, 140.33, 141.66, 149.94, 151.45, 159.01, 161.91, 166.74, 167.47; HRMS (m/z): [M+H]$^+$ calcd for C$_{27}$H$_{25}$N$_2$O$_4$, 473.1707; found, 473.1716.

4-(4,5-dihydro-4-((5-(4,5-dimethyl-2-benzonitrile)furan-2-yl)methylene)-3-methyl-5-oxopyrazol-1-yl)-benzoic acid (6o) was obtained as a red solid (56%). mp: 295-297° C. $^1$H NMR (500 MHz, DMSO-d$_6$) δ 2.30 (s, 1H), 2.35 and 2.38 (2s, 6H), 7.54 (s, 1H), 7.64 (s, 1H), 7.74 (s, 1H), 7.93 (s, 1H), 8.00 (d, J=9.0 Hz, 2H), 8.06 (d, J=6.5 Hz, 2H), 8.66 (s, 1H); $^{13}$C NMR, (100 MHz, DMSO-d$_6$): δ 12.59, 18.53, 19.45, 194.05, 113.32, 116.46, 118.14, 121.37, 125.71, 126.50, 127.40, 127.55, 128.50, 130.04, 134.81, 139.06, 141.36, 143.03, 149.74, 150.92, 155.03, 161.37, 166.64, HRMS (m/z): [M+H]$^+$ calcd for C$_{25}$H$_{20}$N$_3$O$_4$, 426.1448; found, 426.1447.

4-(4,5-dihydro-3-methyl-5-oxy-4-((5-(pyridin-2-yl)furan-2-yl)methylene)pyrazol-1-yl)benzoic acid (6p) was obtained as a red solid (79%). mp: 294-296° C.; $^1$H NMR (400 MHz, DMSO-d$_6$): δ 2.29 (s, 3H) 7.40 (m, 1H), 7.46 (m, 1H), 7.63 (s, 1H), 7.97 (m, 7H), 8.60 and 8.64 (2s, 2H); $^{13}$C NMR (100 MHz, DMSO-d$_6$): δ 12.68, 113.24, 116.63, 116.87, 120.04, 121.38, 124.09, 124.13, 126.95, 129.60, 130.11, 130.28, 137.29, 146.77, 150.02, 150.52, 151.39, 158.50, 161.72; HRMS (m/z): [M+H]$^+$ calcd for C$_{21}$H$_{16}$N$_3$O$_4$, 374.1135; found, 374.1136.

7. Synthesis of 6c

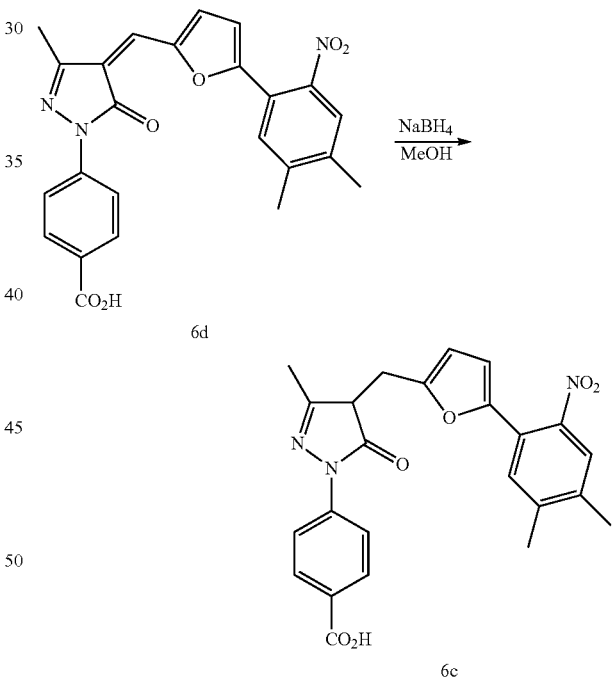

Synthesis, of 4-{4-[5-(4,5-Dimethyl-2-nitro-phenyl)-furan-2-ylmethyl]-3-methyl-5-oxo-4,5-dihydro-pyrazol-1-yl}-benzoic acid (6c). To a solution of 6d (1.00 g, 2.24 mmol) in anhydrous methanol (20 ml) was added sodium borohydride (0.08 g, 2.24 mmol) in portions. During addition gas evolution was observed, and the color of the solution changed from dark red to light yellow. The resulting solution was stirred at room temperature for 30 min, solvent was removed and pH of solution was adjusted to 7 using dilute aq. The resulting solution was extracted With EtOAc and concentrated to give 6c (80%) as an orange solid. mp: 160-163° C., $^1$H NMR (400 MHz, DMSO-d$_6$): δ 2.02 (s, 3H), 2.27 and 2.28

(2s, 6H), 3.56 (s, 2H), 6.05 (s, 1H), 6.61 (s, 1H), 7.50 (s, 1H), 7.61 (s, 1H), 7.85 (d, J=8.4 Hz, 2H), 8.04 (d, J=8.4 Hz, 2H), 12.80 (brs, 1H); $^{13}$C NMR (100 MHz, DMSO-$d_6$): δ 11.82, 18.60, 19.04, 20.66, 38.99, 107.58, 109.91, 117.83, 120.57, 124.26, 126.0, 128.72, 130.12, 137.34, 141.53, 141.96, 144.48, 146.54, 149.14, 155.69, 166.87; HRMS (m/z): $[M+H]^+$ calcd for $C_{24}H_{22}N_3O_6$, 448.1503; found, 448.1507.

8. Synthesis of 6q

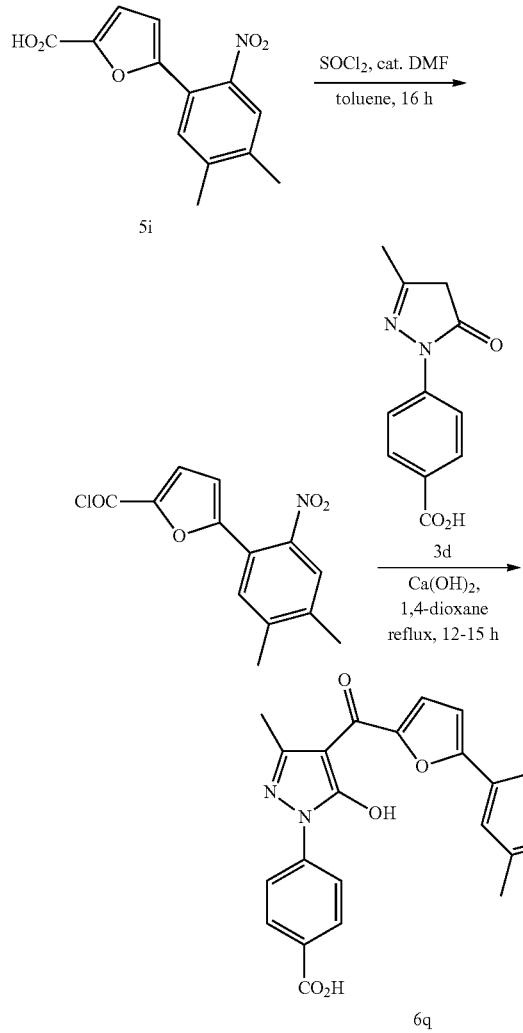

(s, 6H), 6.38 (s, 1H), 7.13 (d, J=4.0 Hz, 1H), 7.68 (s, 1H), 7.77 (s, 1H), 7.77 (d, 4.0 Hz, 1H), 7.80 (d, J=8.4 Hz, 2H), 7.86 (s, 1H), 8.05 (d, J=8.4 Hz, 2H), 13.06 (brs, $^{13}$C NMR (100 MHz, DMSO-$d_6$): δ 19.66, 24.46, 24.60, 102.60, 117.48, 124.79, 126.67, 129.07, 130.56, 134.14, 135.95, 136.08, 136.26, 146.05, 146.39, 147.02, 148.24, 149.07, 150.68, 154.69, 158.03, 159.84, 164.44, 172.01; HRMS: Calculated $[M+H]^+$ for $C_{24}H_{20}N_3O_7$, 462.1296; found, 462.1302.

8. Synthesis of 6r

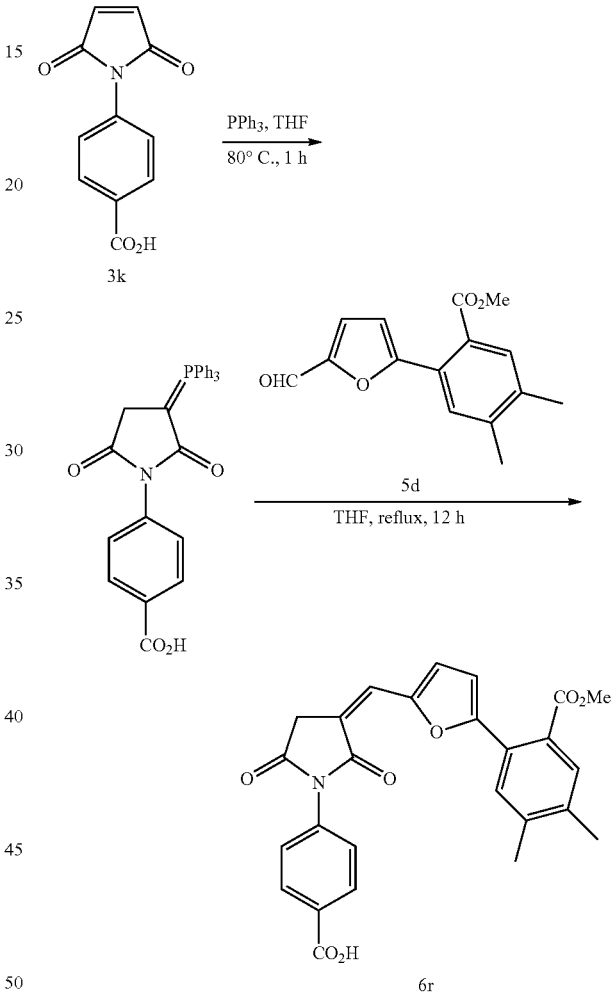

Synthesis of 6q

To a solution of 5-aryl furoic acid 5i (0.72 g, 2.76 mmol) in anhydrous toluene (40 ml) was added thionyl chloride (0.5 ink 11.0 mmol) and a catalytic amount of DMF. The reaction mixture stirred and heated to 80° C. for 16 h. Upon completion, the reaction mixture was concentrated and co-evaporated with dioxane to provide the crude acid chloride. A mixture of acid chloride (0.27 g, 1.26 mmol), pyrazolone 3d (0.35 g, 1.26 mmol) and calcium hydroxide (0.19 g, 2.52 mmol) in anhydrous dioxane (20 ml) was refluxed for 12 h. The reaction mixture was concentrated, and crude product purified by column chromatography using 2-10% MeOH/DCM as eluent to give 6q (38%) as a red solid.[23] mp: 229-232° C.; $^1$H NMR (400 MHz, DMSO-$d_6$): δ 2.27 (s, 3H), 2.35

Synthesis of 2-{5-[1-(4-Carboxy-phenyl)-2,5-dioxo-pyrrolidin-3-ylidenemethyl]-furan-2-yl}-4,5-dimethyl-benzoic acid methyl ester (6r)

To a solution of N-(4-carboxyphenyl)maleimide (3k) (4.05 mmol) in anhydrous THF (20 ml) was added triphenylphosphine (2.65 g, 10.3 mmol) under nitrogen and the reaction mixture was stirred at room temperature for 1 h. To the resulting mixture 5-aryl-furan-2-aldehyde 5d was added (6.07 mmol) and the resulting mixture refluxed for 12 h. The reaction mixture was concentrated under reduced pressure. Crude product was triturated with 50% MeOH/DCM (2×50 ml) and the product filtered, washed with hexane and dried to provide 6r as a yellow solid (32%).[24] mp 290-291° C. $^1$H NMR (400 MHz; DMSO-$d_6$): δ2.28 and 2.30 (2s, 6H), 3.64 (s, 2H), 3.79

(s, 3H), 6.94 (d, J=3.2 Hz, 1H), 7.14 (d, J=3.2 Hz, 1H), 7.37 (s, 1H), 7.50 (m, 7.55 (s, 1H), 8.05 (d, J=8.4 Hz, 2H), 13.14 (brs, 1H); $^{13}$C NMR (100 MHz, DMSO-d$_6$): δ 19.66, 19.98, 35.00, 53.12, 111.55, 120.04, 120.28, 122.20, 126.57, 127.60, 127.91, 110.21, 130.45, 130.86, 131.12, 137.16, 138.41, 141:16, 151.34, 156.21, 167.33, 168.98, 169.86, 173.91; HRMS (m/z): [M−H]$^-$ calcd for $C_{26}H_{20}N_{20}NO_7$, 458.1245; found, 458.1242.

References cited in the above synthesis schemes are as follows: [1]Kim et al., *Bull. Korean Chem. Soc.* 12, 376 (1991); [2]Shaw et al., *J. Am. Chem. Soc.* 79, 3561 (1957); [3]WO2006066937; [4]Organ et al., *J. Comb. Chem.* 5, 118 (2003); [5]WO2008157680; [6]Watanabe et al., *Redox Report* 8, 151 (2003); [7]Moreaus et al., *Bioorg. Med. Chem. Lett.* 18, 4022 (2008); [8]Trivedi et al., *Indian J. Heterocyclic Chem.* 17, 385 (2008); [9]US 2009056586; [10]Tutalkova et al., *Collection of Czechoslovak Chemical Communications* 41, 1377 (1976); [11]Singh et al., *European J. of Pharm. Sciences* 25, 255 (2005); [12]Belmar et al., *J. Braz. Chem.* 16, 179 (2005); [13]U.S. Pat. No. 2,634,262; [14]Trujillo-Ferrara et al., *Synthetic Communications* 35, 2017 (2005); [15]Liu et al., *J. Med. Chem.* 51, 7843 (2008); [16]Langner et al., *Chem. Eur. J.* 11, 6254 (2005); [17]Uyanik et al., *J. Am. Chem. Soc.* 131, 251 (2009); [18]Dai et al., *J. Med. Chem.* 50, 1584 (2007); [19]Hosoya et al., *Bioorg. Med. Chem.* 11, 663 (2003); [20]Fleckenstein and Plenio, *J. Org. Chem.* 73, 3236 (2008); [21]WO2007017687; [22]Vasyunicina et al., *Russ. J. Org. Chem.* 41, 742 (2005); [23]Manetti et al., *Chem. Med. Chem.* 1, 973 (2006); and [24]Haval and Argade, *J. Org. Chem.* 73, 6936 (2008).

Methods of Treatment

As p300/CBP HAT inhibition results in inhibition of cell growth as well as induction of cellular apoptosis, senescence, and cell cycle arrest, p300/CBP HAT is a therapeutic target molecule in cell-proliferative disorders, such as cancer.

The invention includes methods for treating a cell-proliferative disorder or inhibiting the growth of tumor cells by inhibiting the activity of p300/CBP HAT. In embodiments, the method invovles administering an effective amount of a p300/CBP HAT inhibitor. In embodiments, the inhibitor is C646.

In embodiments, the cell-proliferative disorder is cancer, including leukemia, brain cancer, lung cancer, CNS cancer, melanoma, renal cancer, prostate cancer, colon cancer, ovarian cancer, and breast cancer.

In embodiments, the tumor cells are from a leukemia, brain cancer, lung cancer, CNS cancer, melanoma, renal cancer, prostate cancer, colon cancer, ovarian cancer, or breast cancer.

When the p300/CBP HAT inhibitors are administered to a subject, the inhibitor will likely be administered as a composition in combination with a pharmaceutically acceptable carrier or excipient. Pharmaceutically acceptable carriers are physiologically acceptable and retain the therapeutic properties of the small molecules, antibodies, nucleic acids, or peptides present in the composition. Pharmaceutically acceptable carriers are well-known in the art and generally described in, for example, Remington's Pharmaceutical Sciences (18$^{th}$ Edition, ed. A. Gennaro, Mack Publishing Co., Easton, Pa., 1990). The compositions may be provided directly to tumor cells, for example, by direct injection, or may be provided systemically. Finally, suitable dose ranges and cell toxicity levels may be assessed using standard dose range experiments that are well-known in the art. Actual dosages administered may vary depending, for example, on the nature of the disorder, the age, weight and health of the individual, as well as other factors.

In embodiments, the p300/CBP inhibitors of the present invention can be administered to a subject by any convenient mute, including, for example, oral, subcutaneous, intradermal, intravenous, intra-arterial, intraperitoneal, or intramuscular injection.

Combination Therapies

The present invention also provides methods of treating a subject using a combination treatment. In embodiments, the present invention is administered in conjunction with other conventional therapies such as radiation treatment or surgery. Radiation therapy is well-known in the art and includes X-ray therapies, such as gamma-irradiation, and radiopharmaceutical therapies. The methodology of radiation treatment of cancer patients is well-known to those of skill in the art. The radiation dosage regimen is generally defined in terms of radiation absorbed dose (Gy), time and fractionation, and will be determined by an oncologist. The amount of radiation a patient receives will depend on various considerations, including the location of the tumor in relation to other critical structures or organs of the body, and the extent to which the tumor has spread. A typical course of treatment for a patient undergoing radiation therapy will be a treatment schedule over a 1 to 6 week period, with a total dose of between 10 and 80 Gy administered to the patient in a single daily fraction of about 1.8 to 2.0 Gy, 5 days a week. In related embodiments, a patient is treated simultaneously or sequentially with a p300/CBP inhibitor and radiation treatment.

In embodiments, a p300/CBP inhibitor is used with at least one additional anti-cancer agent. Anti-cancer agents contemplated by the present invention include chemotherapeutic drugs that are commercially available. Merely to illustrate, the chemotherapeutic agent can be an inhibitor of chromatin function, a topoisomerase inhibitor, a microtubule inhibiting drug, a DNA damaging agent, an antimetabolite (such as folate antagonists, pyrimidine analogs, purine analogs, and sugar-modified analogs), a DNA synthesis inhibitor, a DNA interactive agent (such as an intercalating agent), and/or a DNA repair inhibitor.

Chemotherapeutic agents may be categorized by their mechanism of action into, for example, the following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, temozolamide, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab, rituximab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers, toxins such as Cholera toxin, ricin, *Pseudomonas exotoxin, Bordetella pertussis* adenylate cyclase toxin, or diphtheria toxin, and caspase activators; and chromatin disruptors. Preferred dosages of the chemotherapeutic agents are consistent with currently prescribed dosages.

In embodiments, a p300/CBP inhibitor is used simultaneously or sequentially with radiation treatment, and in addition, at least one additional anti-cancer agent.

Biomarkers

Described herein is a series of tumor cell markers that are associated with p300/CBP HAT inhibition.

Biomarkers include any markers as identified in any one of Tables 4-6 as shown herein. In embodiments, the biomarker is the gene of a marker identified in any one of Tables 4-6. In embodiments, the biomarker is the gene product of a marker identified in any one of Tables 4-6.

The sequences of these biomarkers may be found by reference to the Affymetrix reference numbers in Tables 4-6. Primers for amplifying the biomarkers may be developed by those of skill in the art. Genes associated with the following functions are down-regulated in tumor cells that experience p300/CBP HAT inhibition: negative regulation of mitotic metaphase/anaphase transition, regulation of cell cycle, regulation of chromosome segregation, regulation of microtubule-based process, G2/M transition DNA damage checkpoint, nucleosome assembly, DNA replication-dependent nucleosome assembly, centromere complex assembly, establishment of organelle localization, chromatin binding, kinetochore binding, damaged DNA binding, DNA bending activity, DNA clamp loader activity, structure-specific DNA binding, ATP binding, histone binding, and chromo shadow domain binding.

In embodiments, the biomarkers correlate with tumor cell response to p300/CBP inhibition.

In embodiments, differential expression of the biomarker in response to an agent is indicative of the therapeutic efficacy of the agent as an inhibitor of p300/CBP HAT.

The invention includes using a biomarker to evaluate the treatment response of a subject having cancer to therapy. In embodiments, the method involves obtaining a biological sample from the subject after treatment with an inhibitor of p300/CBP HAT. In embodiments, the method involves measuring at least one biomarker in the biological sample, wherein the biomarker is selected from one or more of a marker identified in any one of Tables 4-6. In embodiments, the method involves correlating the measurement of the biomarker, e.g., expression level of the biomarker, with the treatment response of the subject.

Where the assay is used to monitor the efficacy of a treatment, the step of detecting the presence and abundance of the marker protein or its transcript in samples of interest is repeated at intervals and these values are then compared. The changes in the detected concentrations reflect changes in the status of the tissue. Where the assay is used to evaluate the efficacy of a therapy, the monitoring steps occur following administration of the therapeutic agent.

The invention includes using a biomarker to develop a combination therapy for treating a subject having cancer. In embodiments, the method involves contacting a cancer cell with an inhibitor of p300/CBP HAT, resulting in a treated cancer cell. In related embodiments, the method involves comparing gene expression of the cancer cell and the treated cancer cell. In embodiments, the method involves identifying a gene that has at least 2-fold change in expression in the treated cancer cell as compared to the cancer cell, wherein the gene is associated with cancer development or progression. In related embodiments, if there was a decrease in gene expression in the treated cells, the method involves developing a combination therapy comprising administering to the subject an effective amount of the p300/CBP HAT inhibitor and an agent that inhibits the activity of the gene product. In related embodiments, if there was an increase in gene expression in the treated cells, the method involves developing a combination therapy comprising administering to the subject an effective amount of the inhibitor p300/CBP HAT and an agent that enhances the activity of the gene product. In embodiments, the agent is a chemotherapeutic agent that is well-known in the art. In some embodiments, the agent is a chemotherapeutic agent described herein, including cisplatin or temozolamide.

Any suitable methods can be used to detect one or more of the markers described herein. These methods include, without limitation, mass spectrometry (e.g., laser desorption/ionization mass spectrometry), immunoassays, surface plasmon resonance, ellipsometry and atomic force microscopy. Methods may further include, by one or more of microarrays, PCR methods, electrospray ionization mass spectrometry (ESI-MS), ESI-MS/MS, ESI-MS/(MS)n, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), atmospheric pressure chemical ionization mass spectrometry (APC)-MS), APCI-MS/MS, APCI-(MS)n, atmospheric pressure photoionization mass spectrometry (APPI-MS), APPI-MS/MS, and APPI-(MS)n, quadrupole mass spectrometry, fourier transform mass spectrometry (FTMS), and ion trap mass spectrometry, where n is an integer greater than zero. Suitable immunoassays include competitive and noncompetitive assay systems using techniques such as BIAcore analysis, FACS analysis, immunofluorescence, immunohistochemical staining, Western blots (immunobots), radioimmunoassays, ELISA, "sandwich" immunoassays, immunoprecipitation assays, precipitation reactions, gel diffusion precipitin reactions, immunodiffusion assays, agglutination assays, complement-fixation assays, immunoradiometric assays, fluorescent immunoassays, fluorescence-activated cell sorting (FACS), protein A immunoassays, etc. Assays used in a method of the invention can be based on colorimetric readouts, fluorescent readouts, mass spectrometry, visual inspection, etc. Assays can be carried out, e.g., with suspension beads, or with arrays, in which antibodies or cell or patient samples are attached to a surface such as a glass slide or a chip.

In the above aspects and embodiments of the invention, the cancer may be leukemia, brain cancer, lung cancer, CNS cancer, melanoma, renal cancer, prostate cancer, colon cancer, ovarian cancer, or breast cancer.

EXAMPLES

It should be appreciated that the invention should not be construed to be limited to the examples that are now described; rather, the invention should be construed to include any and all applications provided herein and all equivalent variations within the skill of the ordinary artisan.

Example 1

Ranking and Selection of Compounds from Virtual Screening of p300 HAT

A recent high resolution X-ray structure of the p300 HAT in complex with the bisubstrate analog Lys-CoA was recently reported in Liu et al., *Nature* 451, 846 (2008), revealing key aspects about substrate recognition and the mechanism of catalysis. The structure shows that a narrow tunnel in p300 accommodates Lys-CoA, and the inhibitor makes a range of hydrogen bonding and Van der Waals interactions with residues in the HAT active site. Information about the Lys-CoA/p300 HAT structure was employed in a virtual ligand screening to identify novel small molecule p300 HAT inhibitors.

Compounds from a screening set of nearly 500,000 commercially available small molecules were docked into the p300 HAT structure in the Lys-CoA binding pocket and assigned a score using the ICM-VLS software version 3.5. The components of the ICM (Internal Coordinate Mechanics) score include the internal force-field energy of the ligand, conformational entropy loss of the ligand, receptor-ligand hydrogen-bond interaction, solvation electrostatic energy change, hydrogen-bond donor/acceptor desolvation and hydrophobic energy (Totrov et al., *Proceedings of the Third Annual International Conference on Computational Molecular Biology*, 312 (1999)). The score is trained to separate binders and non-binders and to rank the interaction of the compound with the receptor. The best score from each of the three docking runs was recorded, and the screened compounds were then ranked by ICM score. The 194 highest scoring compounds (representing 0.04% of the total compound database) were visually inspected and selected based on their availability and interactions with the receptor. Each of the 194 compounds was purchased from ChemBridge (San Diego, Calif.) and tested.

Example 2

Experimental p300 HAT Assays and Inhibitor Validation

After completing the computational docking screen, the top 194 inhibitors were tested in a convenient spectrophotometric assay as described in Kim et al., *Anal. Biochem.* 280, 308 (2000). In the coupled spectrophotometric assay, the acetyltransferase reaction product CoASH becomes a substrate for alpha-ketoglutarate dehydrogenase, which converts NAD to NADH, resulting in an increase of UV absorbance at 340 nm. Screening conditions for these p300 HAT assays included substrate concentrations of 200 µM histone H4-15 peptide and 50 µM acetyl-CoA, and potential small molecule inhibitors tested at 100 µM. Thirty of the original 194 compounds showed at least 50% inhibition under these conditions. To distinguish inhibitory effects related to blockade of coupling enzyme rather than p300, assays were repeated using increased (2-fold) alpha-ketoglutarate dehydrogenase. This eliminated six of the thirty hits. The remaining compounds were then assessed in a protein aggregation-related inhibition assay as described in Feng et al., *Nat. Chem. Biol.* 1, 146 (2005). The assays were performed in the presence of 0.01% Triton X-100, which attenuated inhibition of 11 of the 24 compounds. NMR and mass spectrometry confirmed the structure and purity of the thirteen potential p300 inhibitors, which were subsequently tested in a direct, radioactive assay for $IC_{50}$ measurements. In this radioactive p300 HAT assay, $^{14}C$ transfer from $^{14}C$-acetyl-CoA into peptide substrate is directly measured using Tris-Tricine SDSPAGE and phosphorimage analysis. The results of these assays are reproduced below in Table 1.

TABLE 1 p300 HAT inhibition.

| ID | % inhibition in initial screen | % inhibition with .01% Triton X-100 | % inhibition with 2x coupling enz | % inhibition at 25 uM in radioactive assay |
|---|---|---|---|---|
| 5109125 | 0.0 | | | |
| 5140276 | 0.0 | | | |
| 5150485 | 0.0 | | | |
| 5158493 | 0.0 | | | |
| 5202146 | 43.6 | 53.9 | 47.5 | 77.7 |
| 5230534 | 0.0 | | | |
| 5238739 | 68.8 | 100.0 | 0.0 | |
| 5243640 | 0.0 | | | |
| 5252622 | 0.0 | | | |
| 5310308 | 0.0 | | | |
| 5316952 | 0.0 | | | |
| 5317891 | 0.0 | | | |
| 5321334 | 100.0 | 100.0 | 100.0 | 17.1 |
| 5380287 | 83.9 | 93.9 | 50.2 | |
| 5466641 | 11.6 | | | |
| 5471129 | 13.5 | | | |
| 5475041 | 25.4 | | | |
| 5525795 | 0.0 | | | |
| 5651487 | 11.6 | | | |
| 5651711 | 0.0 | | | |
| 5654648 | 30.3 | | | |
| 5655291 | 45.4 | 52.5 | 0.0 | |
| 5659790 | 11.9 | | | |
| 5670426 | 5.7 | | | |
| 5686889 | 0.0 | | | |
| 5687670 | 21.1 | | | |
| 5741582 | 100.0 | 9.4 | | |
| 5755944 | 22.8 | | | |
| 5767379 | 24.2 | | | |
| 5768401 | 58.0 | 38.9 | | |
| 5770578 | 0.0 | | | |
| 5773966 | 11.8 | | | |
| 5774017 | 9.2 | | | |
| 5793056 | 67.6 | 96.9 | 19.3 | |
| 5838646 | 100.0 | 100.0 | 100.0 | 89.9 |
| 5906998 | 0.0 | | | |
| 5913665 | 0.0 | | | |
| 5915900 | 0.0 | | | |
| 5917216 | 38.6 | | | |
| 5920906 | 0.0 | | | |
| 5992675 | 79.5 | 83.6 | 64.2 | 11.0 |
| 6001070 | 0.0 | | | |
| 6046441 | 0.0 | | | |
| 6079531 | 0.0 | | | |
| 6086620 | 0.0 | | | |
| 6138959 | 0.0 | | | |
| 6153236 | 0.0 | | | |
| 6155974 | 0.0 | | | |
| 6159295 | 0.0 | | | |
| 6165973 | 0.0 | | | |
| 6191905 | 18.8 | | | |
| 6223625 | 53.9 | 64.4 | 30.5 | |
| 6235961 | 0.0 | | | |
| 6312870 | 0.0 | | | |
| 6331077 | 0.0 | | | |
| 6355266 | 0.0 | | | |
| 6382820 | 0.0 | | | |
| 6428671 | 0.0 | | | |
| 6430587 | 0.0 | | | |
| 6435061 | 0.0 | | | |
| 6453877 | 0.0 | | | |
| 6508796 | 0.0 | | | |
| 6635973 | 0.0 | | | |
| 6639771 | 0.0 | | | |
| 6643375 | 78.8 | 74.8 | 67.3 | 90.9 |
| 6644538 | 0.0 | | | |
| 6649979 | 0.0 | | | |
| 6656404 | 0.0 | | | |
| 6802426 | 0.0 | | | |

TABLE 1-continued p300 HAT inhibition.

| ID | % inhibition in initial screen | % inhibition with .01% Triton X-100 | % inhibition with 2x coupling enz | % inhibition at 25 uM in radio-active assay |
|---|---|---|---|---|
| 6868964 | 0.0 | | | |
| 6926722 | 0.0 | | | |
| 7112743 | 0.0 | | | |
| 7185124 | 0.0 | | | |
| 7198857 | 0.0 | | | |
| 7261568 | 0.0 | | | |
| 7409713 | 0.0 | | | |
| 7510967 | 100.0 | 100.0 | 63.6 | |
| 7643849 | 0.0 | | | |
| 7778714 | 0.0 | | | |
| 7807148 | 0.0 | | | |
| 7821005 | 0.0 | | | |
| 7821134 | 0.0 | | | |
| 7849310 | 0.0 | | | |
| 7885320 | 0.0 | | | |
| 7890191 | 0.0 | | | |
| 7891250 | 0.0 | | | |
| 7912863 | 48.9 | 82.5 | 100.0 | 0.0 |
| 7921139 | 0.0 | | | |
| 7928470 | 0.0 | | | |
| 7985549 | 0.0 | | | |
| 7986664 | 0.0 | | | |
| 7988132 | 0.0 | | | |
| 7989492 | 0.0 | | | |
| 9016834 | 0.0 | | | |
| 5105880 | 0.0 | | | |
| 5118298 | 0.0 | | | |
| 5157234 | 0.0 | | | |
| 5175587 | 0.0 | | | |
| 5186546 | 37.4 | | | |
| 5230675 | 0.0 | | | |
| 5238242 | 41.5 | 77.7 | 64.2 | 13.3 |
| 5238415 | 0.0 | | | |
| 5319310 | 0.0 | | | |
| 5563823 | 0.0 | | | |
| 5573194 | 0.0 | | | |
| 5574003 | 0.0 | | | |
| 5647087 | 0.0 | | | |
| 5682055 | 0.0 | | | |
| 5683894 | 0.0 | | | |
| 5687750 | 0.0 | | | |
| 5688622 | 0.0 | | | |
| 5854380 | 0.0 | | | |
| 5871879 | 0.0 | | | |
| 5913104 | 0.0 | | | |
| 5913142 | 0.0 | | | |
| 5913514 | 0.0 | | | |
| 5913544 | 0.0 | | | |
| 5915300 | 0.0 | | | |
| 5915918 | 0.0 | | | |
| 6048056 | 77.0 | 86.1 | 72.0 | 0.0 |
| 6084098 | 0.0 | | | |
| 6085225 | 40.4 | 0.0 | | |
| 6141533 | 31.1 | | | |
| 6161416 | 0.0 | | | |
| 6221811 | 31.8 | | | |
| 6251635 | 0.0 | | | |
| 6382958 | 81.4 | 0.0 | | |
| 6394550 | 0.0 | | | |
| 6396565 | 0.0 | | | |
| 6435118 | 0.0 | | | |
| 6448709 | 0.0 | | | |
| 6525646 | 0.0 | | | |
| 6526225 | 0.0 | | | |
| 6539062 | 0.0 | | | |
| 6630259 | 0.0 | | | |
| 6651866 | 54.4 | 61.6 | 75.3 | 0.0 |
| 6658215 | 0.0 | | | |
| 6658754 | 0.0 | | | |
| 6671323 | 0.0 | | | |
| 6764489 | 73.2 | 100.0 | 100.0 | 0.0 |
| 6786461 | 66.6 | 58.2 | 100.0 | 0.0 |
| 6801779 | 0.0 | | | |
| 6815206 | 21.6 | | | |
| 6873168 | 0.0 | | | |
| 6883862 | 44.5 | 17.5 | | |
| 6950536 | 0.0 | | | |
| 6971425 | 0.0 | | | |
| 7076620 | 0.0 | | | |
| 7103014 | 34.1 | | | |
| 7156725 | 23.7 | | | |
| 7188864 | 0.0 | | | |
| 7195131 | 0.0 | | | |
| 7255575 | 0.0 | | | |
| 7265947 | 0.0 | | | |
| 7403938 | 69.5 | 30.9 | | |
| 7457729 | 15.0 | | | |
| 7514782 | 0.0 | | | |
| 7597513 | 0.0 | | | |
| 7723697 | 27.9 | | | |
| 7727933 | 0.0 | | | |
| 7728414 | 0.0 | | | |
| 7738699 | 0.0 | | | |
| 7742383 | 50.0 | 30.0 | | |
| 7753734 | 50.8 | 12.6 | | |
| 7769952 | 27.0 | | | |
| 7783270 | 0.0 | | | |
| 7791905 | 0.0 | | | |
| 7821436 | 42.1 | 20.4 | | |
| 7848437 | 0.0 | | | |
| 7858888 | 63.1 | 18.7 | | |
| 7912130 | 0.0 | | | |
| 7913721 | 44.4 | 25.8 | | |
| 7916989 | 33.8 | | | |
| 7926342 | 34.6 | | | |
| 7928973 | 16.4 | | | |
| 7931035 | 100.0 | 98.6 | 100.0 | 0.0 |
| 7933364 | 0.0 | | | |
| 7936308 | 0.0 | | | |
| 7940467 | 0.0 | | | |
| 7943124 | 0.0 | | | |
| 7960629 | 100.0 | 94.4 | 100.0 | 0.0 |
| 7972578 | 0.0 | | | |
| 7994448 | 0.0 | | | |
| 9004400 | 0.0 | | | |
| 9005702 | 0.0 | | | |
| 9021796 | 0.0 | | | |
| 9040132 | 0.0 | | | |
| 5470529 | 95.4 | | | |
| 5485989 | 0.0 | | | |
| 5537648 | 0.0 | | | |
| 5693758 | 0.0 | | | |
| 5700424 | 0.0 | | | |
| 5313714 | | | | |

Three compounds, C646 (ChemBridge #5838646), C146 (ChemBridge #5202146), and C375 (ChemBridge #6643375) were ultimately shown to be relatively potent p300 HAT inhibitors (Ki<5 μM) (FIG. 1). Interestingly, though C646, C146, and C375 possess distinct scaffolds, these three compounds all contain a linear arrangement of 3-4 aromatic rings terminating in a benzoic acid.

Example 3

Acetyltransferase Inhibitor Selectivity

Each of the three inhibitors C646, C146, and C375 was further analyzed versus other acetyltransferases for specificity, specifically, serotonin N-acetyltransferase (Szewczuk et al., *J. Med. Chem.* 50, 5330 (20707), PCAF histone acetyltransferase (Lau et al., *J. Biol. Chem.* 275, 1953 (2000), GCN5 histone acetyltransferase (Poux et al., *Proc. Natl. Acad. Sci. USA* 99, 14065 (2002), Rtt109 histone acetyltransferase (Tang et al., *Nat. Struct. Mol. Biol.* 15, 738 (2008), Sas histone acetyltransferase (Shia et al., *J. Biol. Chem.* 280, 11987 (2005), and MOZ histone acetyltransferase (Holbert et al., *J. Biol. Chem.* 282, 36603 (2007).

TABLE 2

Percent inhibition of acetyltransferase with 10 μM of the specified compound.

| Cpd. | p300 | AANAT | PCAF | GCN5 | Sas | Moz | Rtt109 |
|---|---|---|---|---|---|---|---|
| C646 | 86% | <10% | <10% | <10% | <10% | <10% | 10% |
| C146 | 87% | <10% | >95% | ND | ND | ND | ND |
| C375 | 79% | 73% | ND | ND | ND | ND | ND |

ND = not determined

While compound C646 at 10 μM was highly selective in inhibiting p300 (86% inhibition) versus the other six acetyltransferases (less than 10% inhibition), C146 and C375 were less selective, inhibiting at least one of these enzymes with comparable potency to their p300 blockade (Table 1). C646 is therefore a promising compound for use in applications requiring selective inhibition of p300/CBP.

Example 4

Mechanism of Inhibition

Figure 2A:
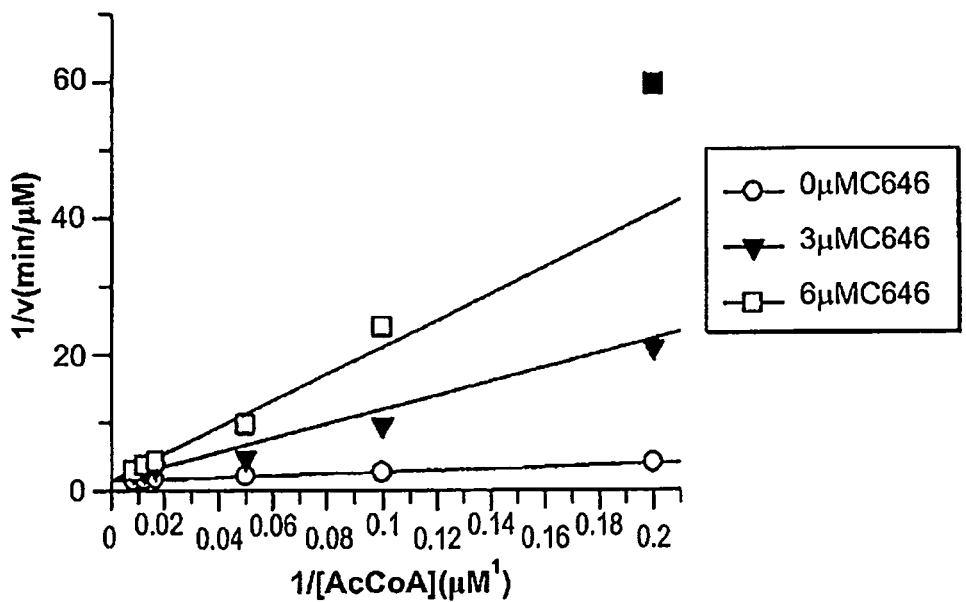
FIG. 2A is a plot of 1/v vs. 1/[acetyl-CoA] at fixed concentration of H4-15 peptide substrate (100 μM). Three concentrations of C646 showed competitive inhibition. C646 $K_i$=400±60 nM, apparent acetyl-CoA $K_m$=8.5±1.4 μM, and apparent $k_{cat}$=18±1 min$^{-1}$.
Figure 2B:
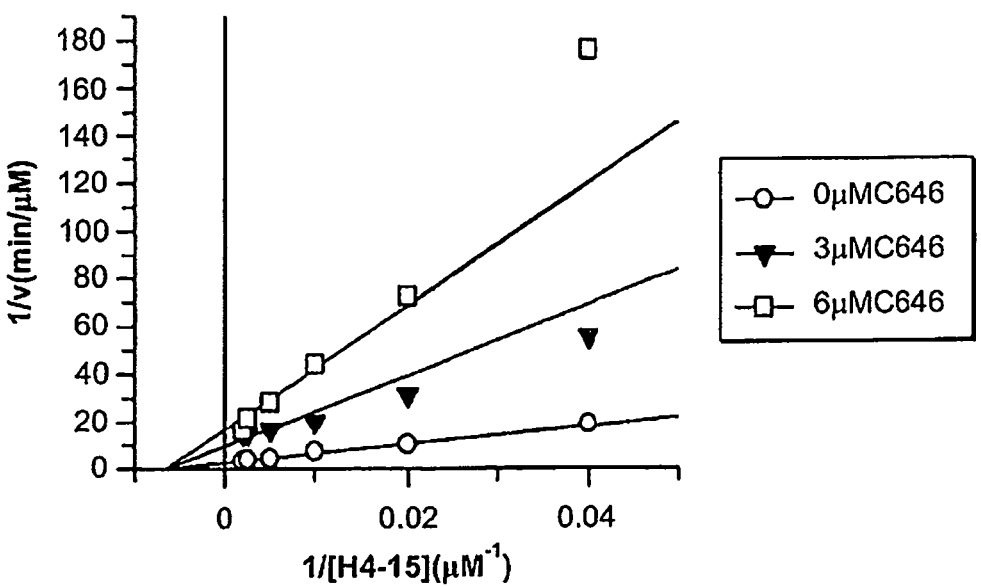
FIG. 2B is a plot of 1/v vs. 1/[peptide substrate (H4-15)] at fixed concentration of acetyl-CoA (10 μM). Three concentrations of C646 showed noncompetitive inhibition. C646 $K_i$=530±40 nM, apparent H4-15 $K_m$=155±19 μM, and apparent $k_{cat}$=40±2 min$^{-1}$.
Figure 3A:
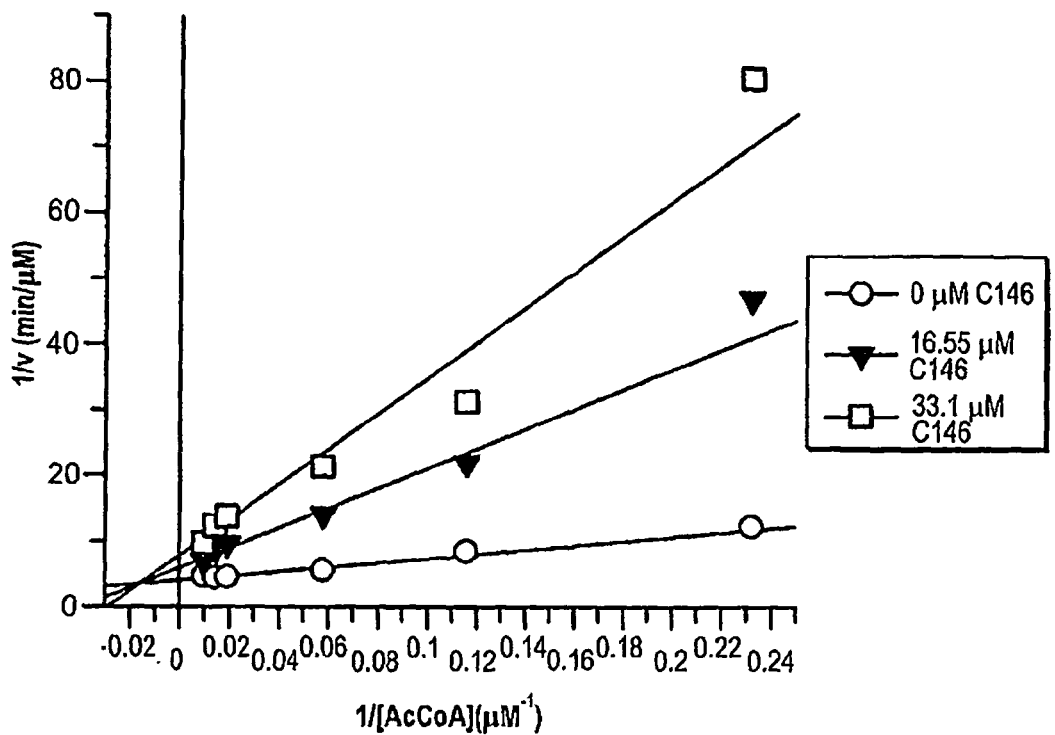
FIGS. 3A-3C show the kinetic characterization of compounds C146 and C375.
Figure 3B:
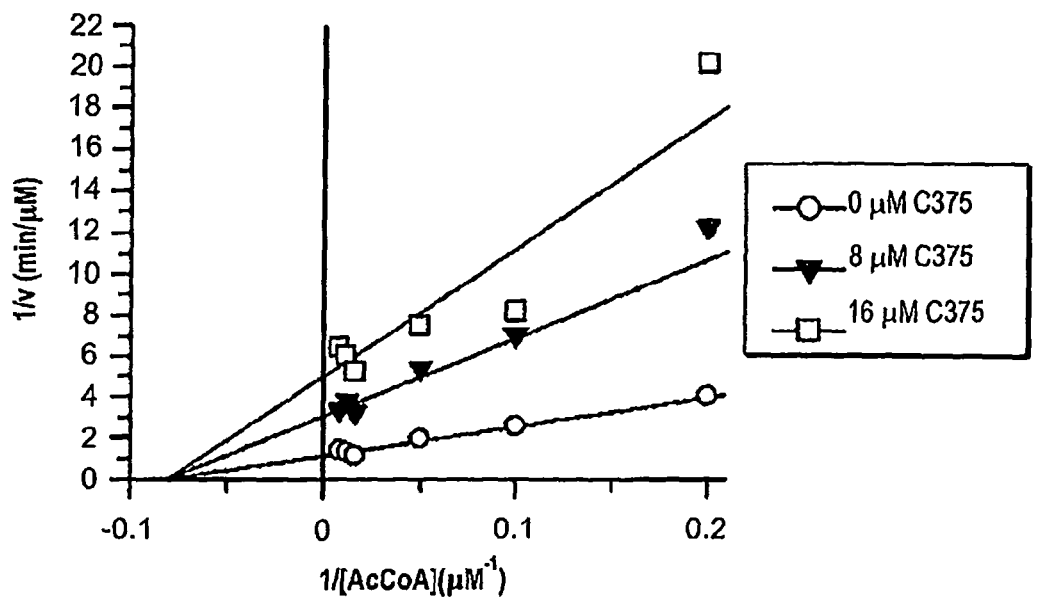
Figure 3C:
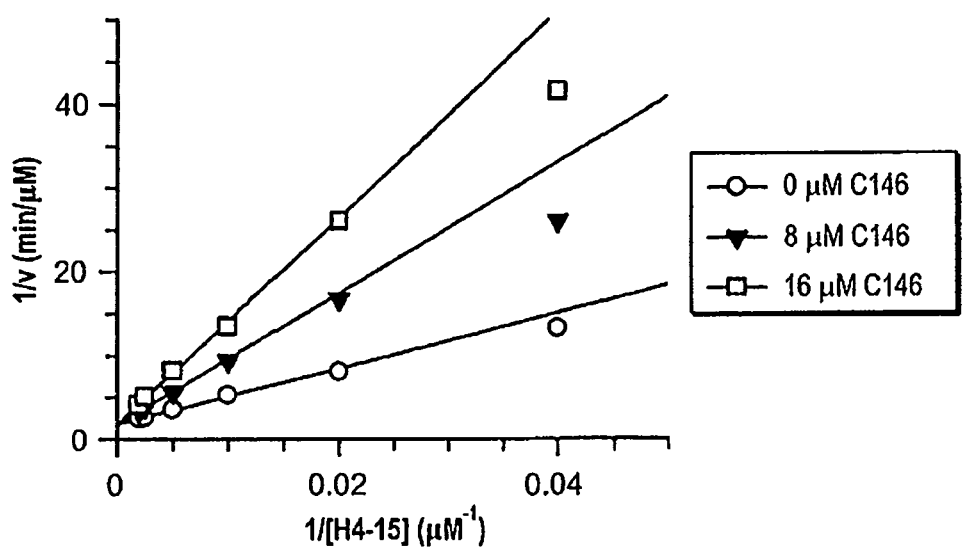
Figures 2, 13A:
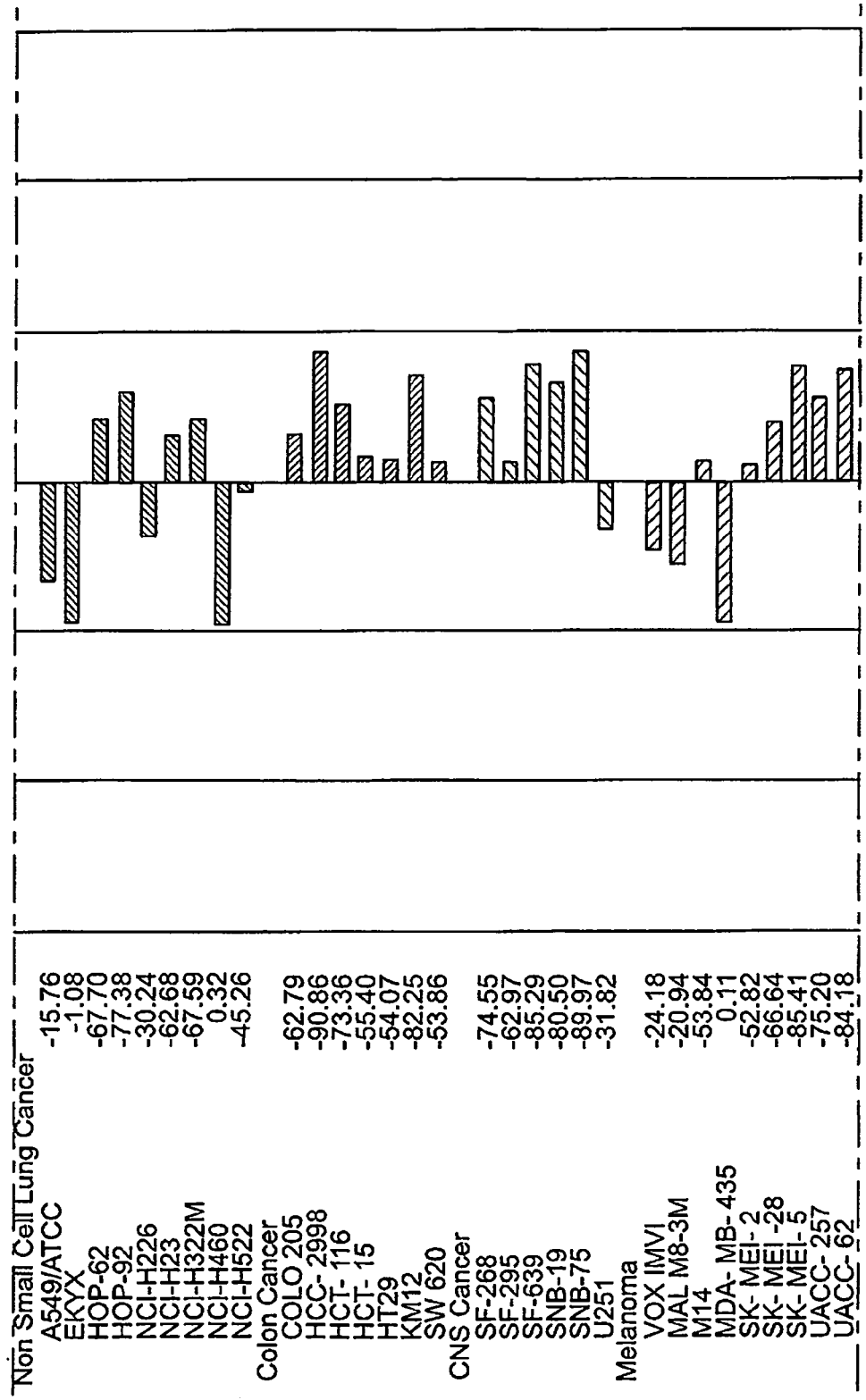

The steady-state kinetic mechanism of inhibition of p300 by C646, C146, and C375 was assessed by exploring inhibitory effects over a range of acetyl-CoA concentrations (FIG. 2). Compound C646 proved to be a linear competitive inhibitor of p300 versus acetyl-CoA with a $K_i$ of 400 nM (FIG. 2A). Compound C146 showed pseudo-competitive inhibition versus acetyl-CoA with $K_i$–slope=4.7 μM, although this compound exhibited a measurable $K_i$–intercept (35 μM) suggesting that C146 still had affinity for the acetyl-CoA-bound form of p300 (FIG. 3A). C375 showed classical noncompetitive inhibition versus p300 ($K_i$=4.8 μM) indicating that it could bind efficiently to the acetyl-CoA bound form of p300 (FIG. 3B). Therefore, C646 was the only compound to exhibit a purely competitive kinetic pattern of p300 inhibition versus acetyl-CoA. In further analysis, C646 showed a noncompetitive pattern of p300 inhibition versus H4-15 peptide substrate (FIG. 2B), consistent with the expected behavior of a bisubstrate analog interacting with an enzyme with ordered substrate binding, like that of p300 (see Yu et al., *Biochemistry* 245, 14788 (2006). Compound C146 was found to be a competitive inhibitor of p300 versus H4-15 peptide substrate (FIG. 3C), suggesting a more complex mode of interaction with the enzyme than a simple bisubstrate analog.

The conjugated pyrazolone exomethylene vinyl functionality in C646 is potentially electrophilic, serving as a possible Michael acceptor, which could covalently modify its protein target. The nucleophilic compound dithiothreitol was added to p300 HAT assays, and we investigated whether the thiol-containing beta-mercaptoethanol could generate adducts with C646. Treatment of C646 with 10 mM beta-mercaptoethanol for up to one hour showed no evidence of reaction based on the absorbance spectrum (data not shown). This lack of reactivity likely results from the extended conjugation of the polyaromatic system in C646.

Figure 2C:
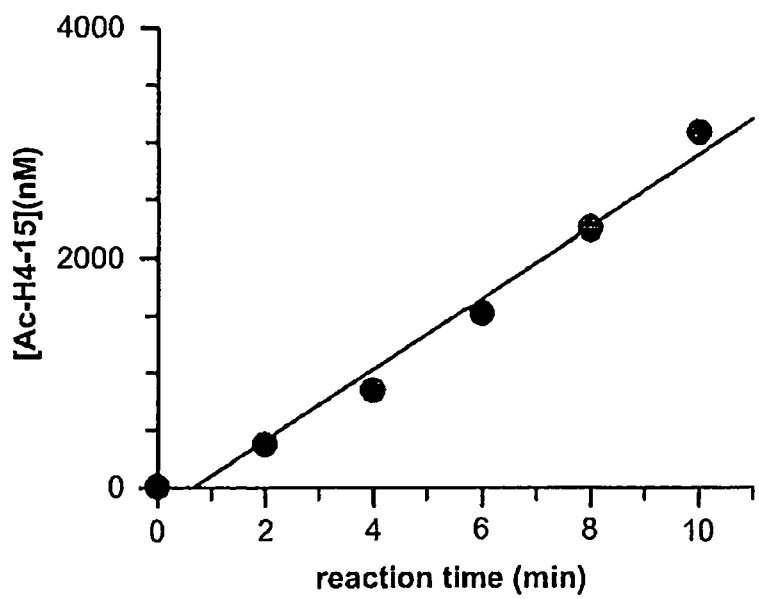
FIG. 2C includes a graph. p300/CBP HAT catalyzed acetyl transfer versus time is linear in the presence of 1.5 μM C646.
Figure 2D:
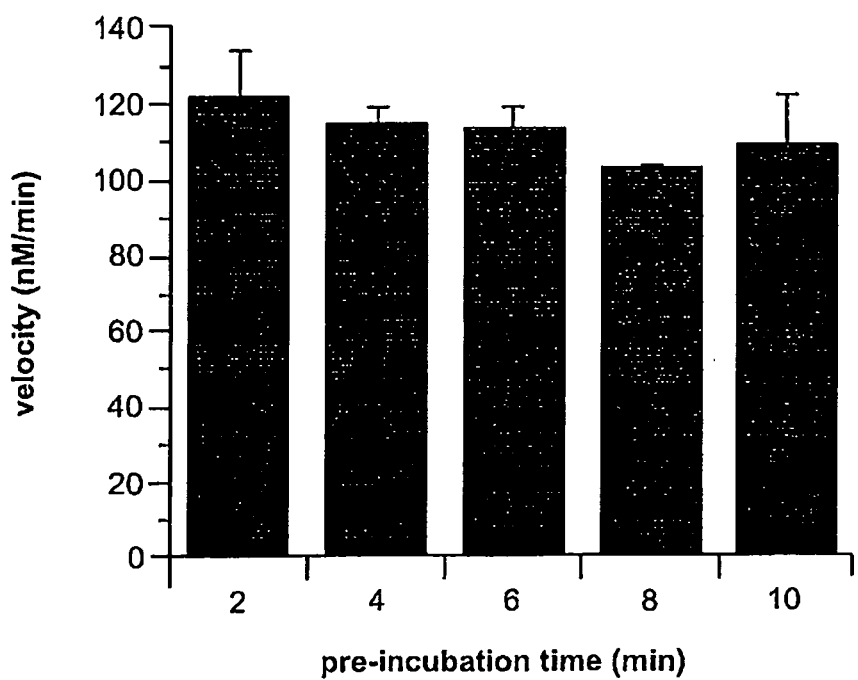
FIG. 2D includes a graph. Preincubation of C646 with p300/CBP HAT for 2-10 min does not alter inhibitory potency.

Irreversible enzyme inhibitors typically exhibit time-dependent enzyme inactivation. In contrast, acetyl transfer catalyzed by p300 HAT in the presence of C646 remained linear over time, consistent with the behavior of a reversible inhibitor (FIG. 2C). Moreover, incubation of C646 with p300 for 2, 4, 6, 8 or 10 min prior to acetyltransferase assays showed that the level of inhibition was independent of preincubation time (FIG. 2D). Without wishing to be bound by theory, these results taken together indicate that C646 is a classical reversible p300 inhibitor, consistent with the steady-state kinetic analysis described above.

Example 5

Conformational Analysis of C646

Figures 3, 13A:
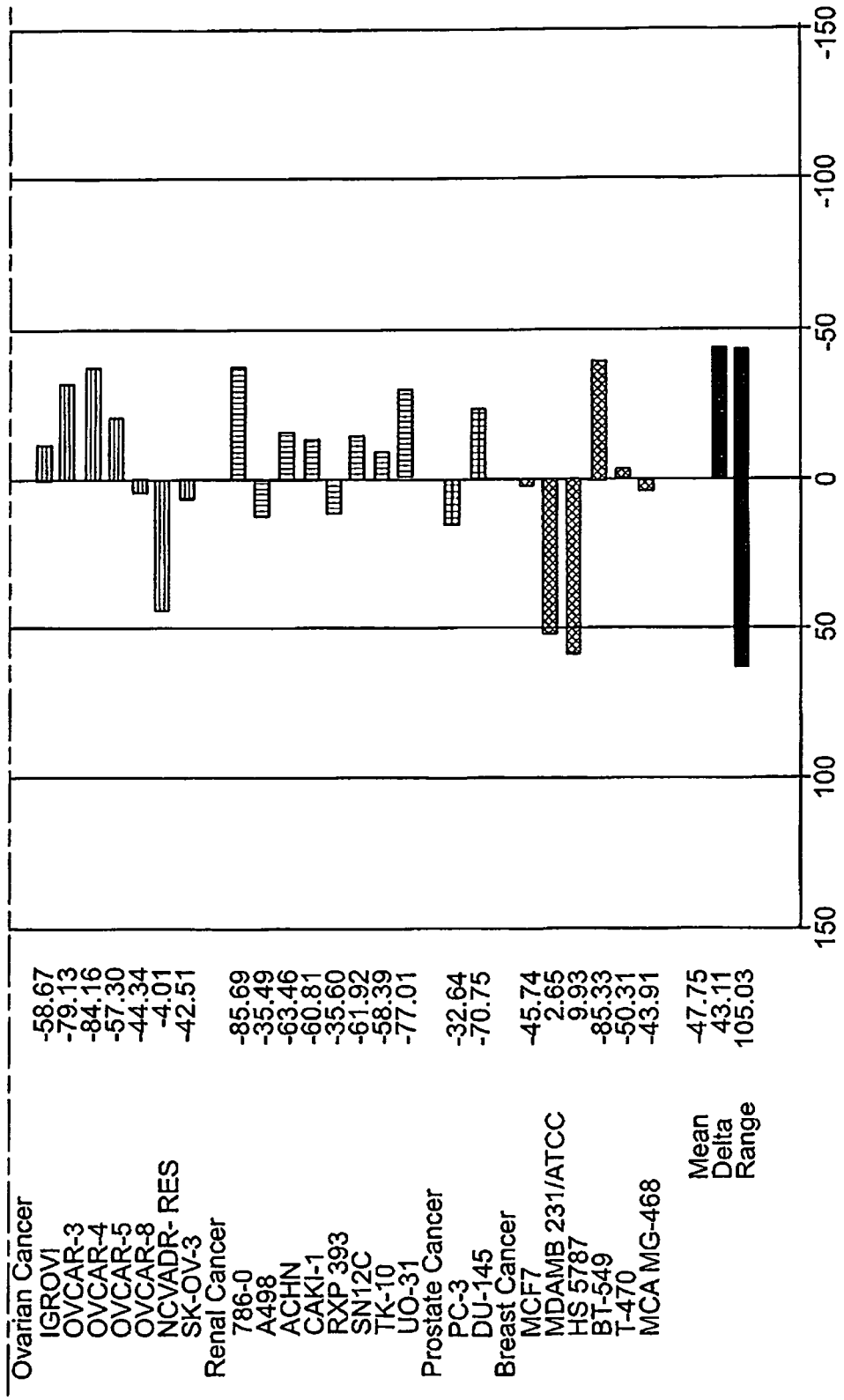
Figure 13B:
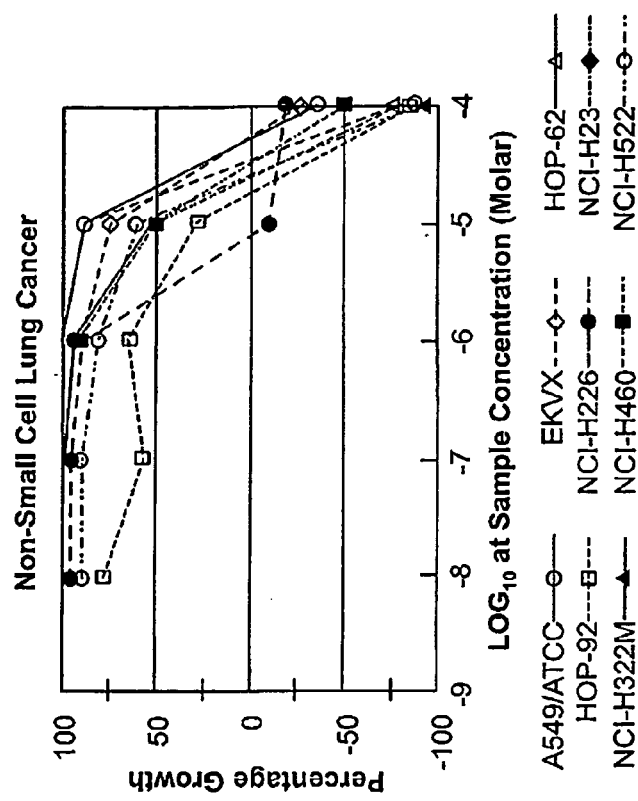
Figures 1, 13B:
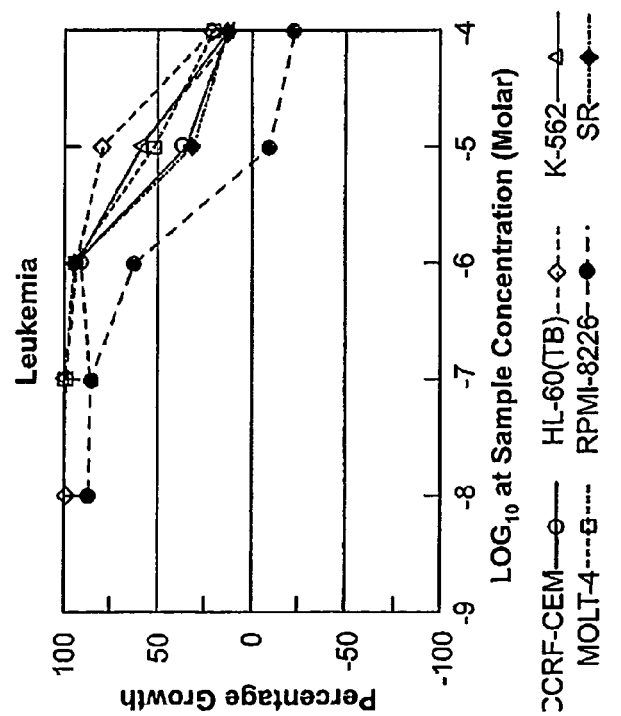
Figures 2, 13B:
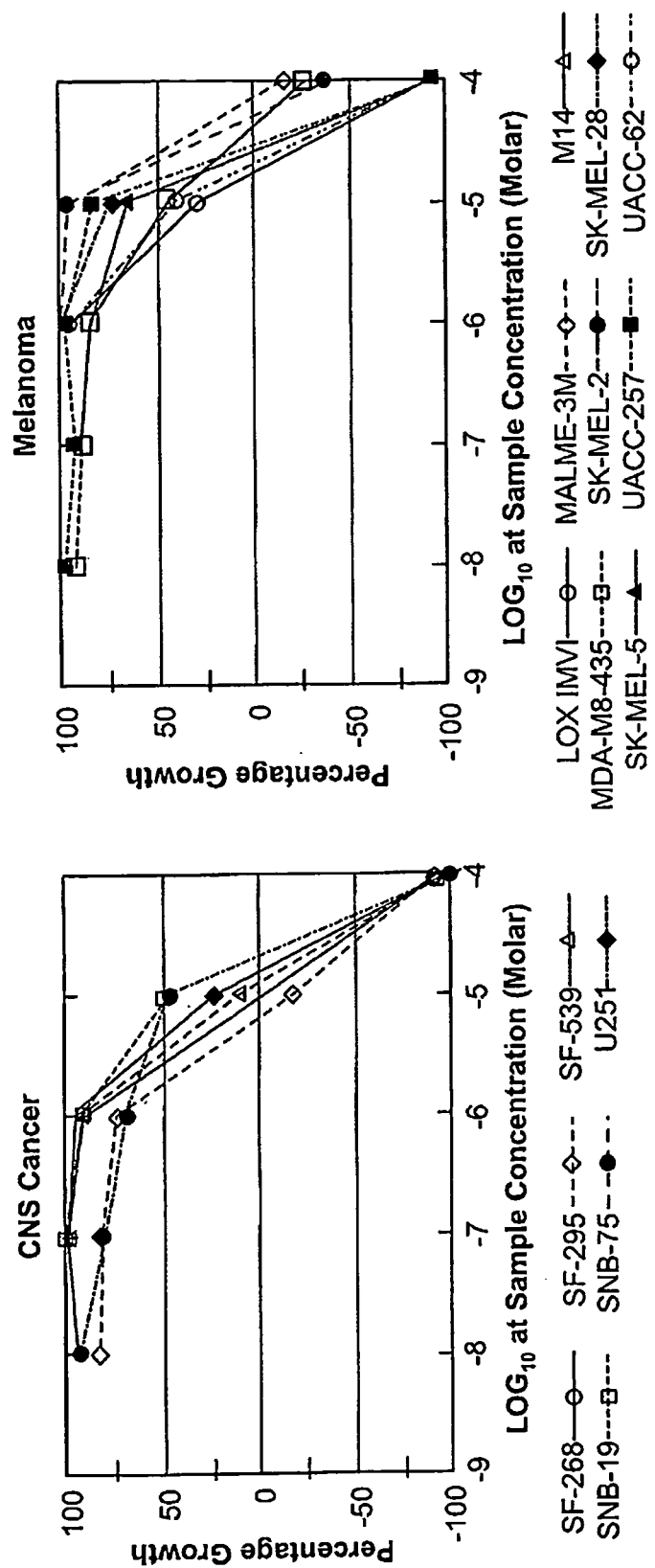
Figures 3, 13B:
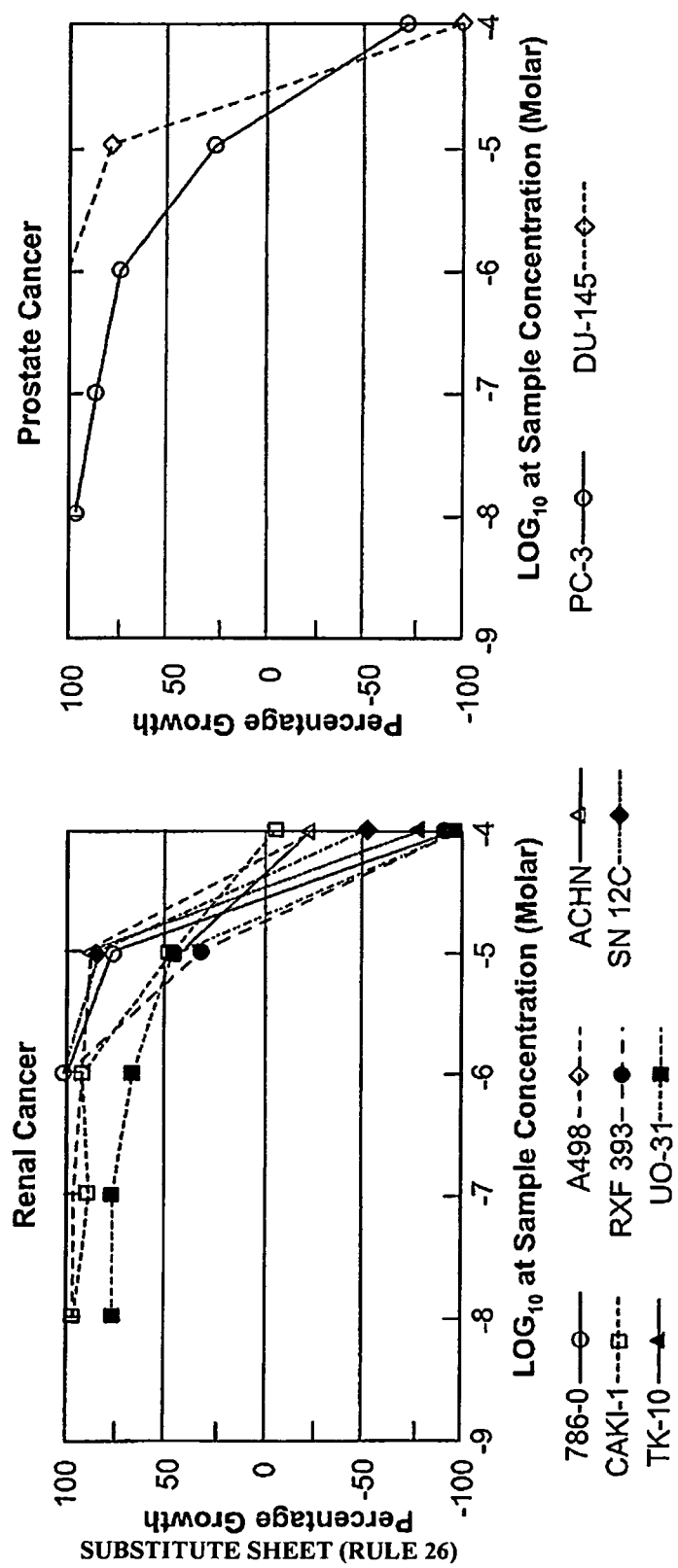

Prior studies reported in Moreau et al., *Bioorg. Med. Chem. Lett.* 18, 4022 (2008) suggested that pyrazolone-furan compounds such as C646 could exist in two double bond stereoisomers involving the exomethylene. Since the computational docking model of C646 bound to p300 suggests that the compound binds as the E-isomer, we investigated C646 stereochemistry in solution using $^1$H NMR and HPLC. $^1$H NMR analysis of C646 in DMSO suggests a 70:30 E:Z-mixture of the olefinic isomers based on the pyrazolone methyl protons (FIG. 3). Using $^1$H-$^1$H 2D NOESY NMR analysis, the major peak can be assigned as the E-isomer based on the NOE between the vinyl proton and the methyl protons in the E-isomer. These isomers can be separated by reversed phase HPLC (FIG. 3); however, the isomers facilely interconvert, since re-injection of samples derived from the individual peaks shows that re-equilibration of peaks is established within a few hours. These data suggest that the E-isomer is readily accessible and likely to be favored in solution.

Example 6

Interactions of C646 and p300 Using Site-Directed Mutagenesis

Figure 4A:
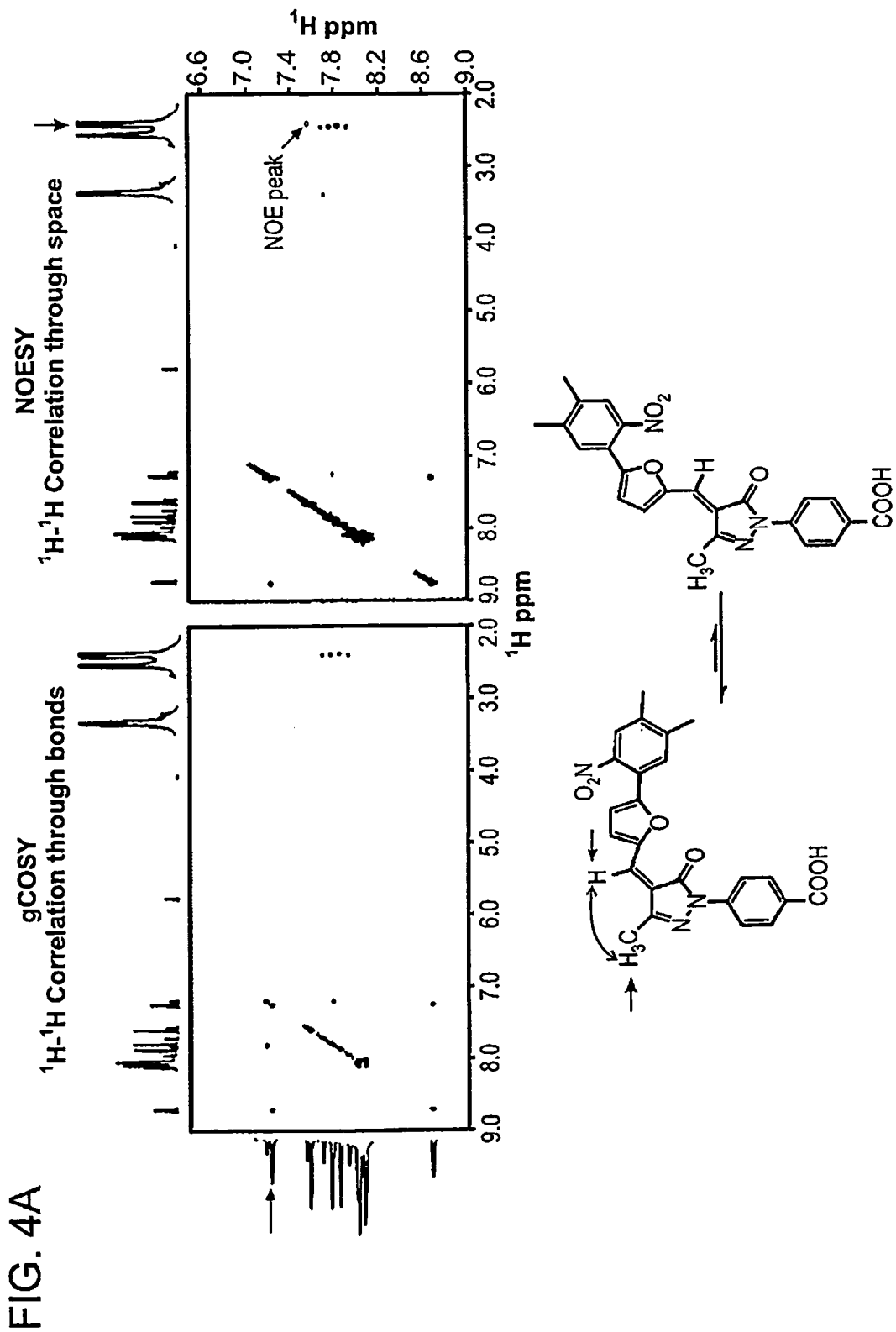
Figure 5:
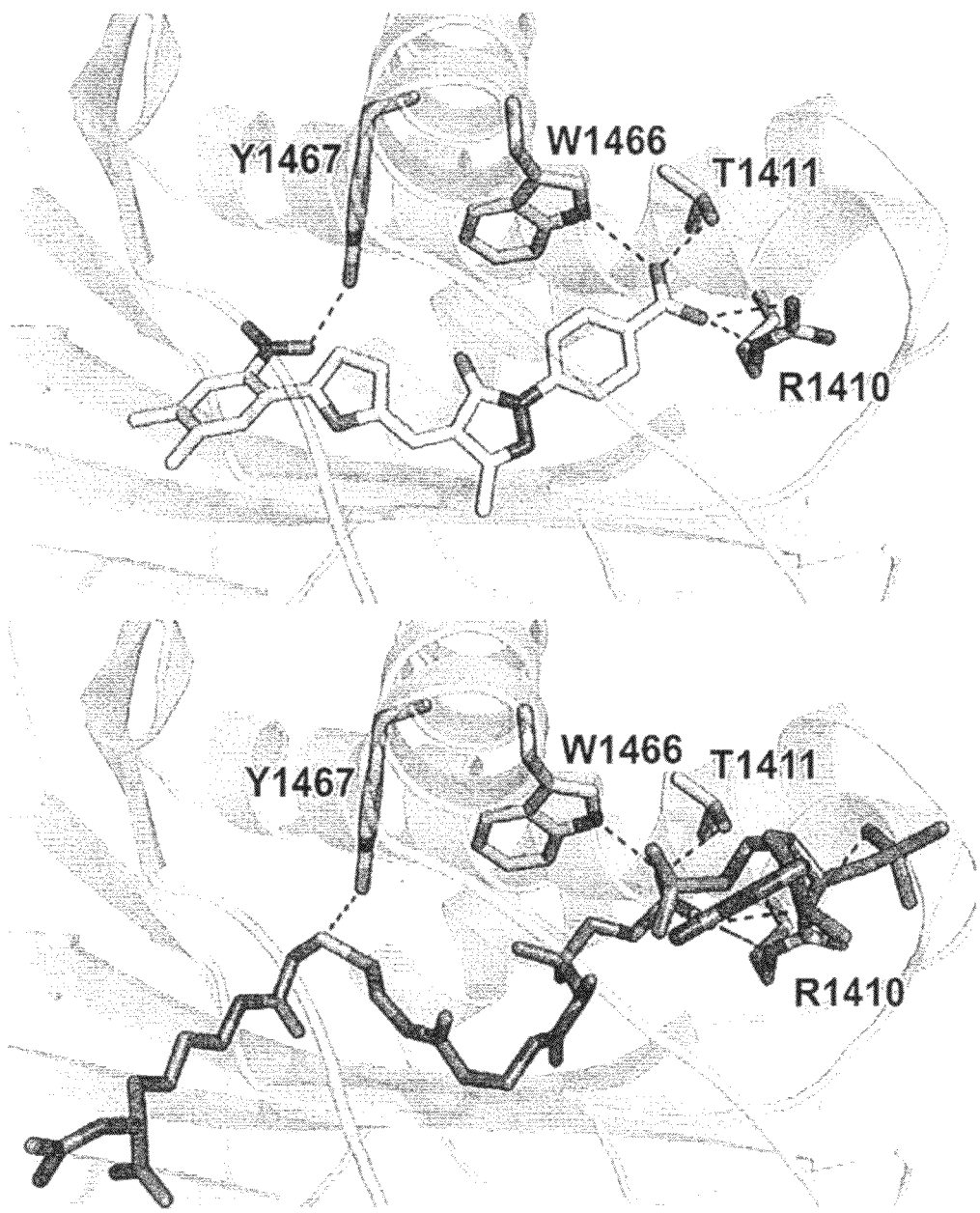
FIG. 5 shows an in silico model of C646 bound to the p300 HAT active site (upper). The model shows overlapping interactions with the X-ray crystal structure of p300 HAT complexed with Lys-CoA (lower).

Site-directed mutagenesis was performed to evaluate specific interactions predicted by the model. In the model, a series of hydrogen bonding donor interactions from the side chains of Thr1411, Tyr1467, Trp1466, and Arg1410 to oxygen atoms of C646 are proposed (FIG. 4). These sidechains also make interactions with Lys-CoA based on the X-ray structure (FIG. 4) (Liu et al., *Nature* 451, 846 (2008)). We thus tested C646 against p300 HAT mutants T1411A, Y1467F, W1466F, and R1410A and the corresponding IC$_{50}$ values are shown in Table 3.

TABLE 3

Kinetic parameters and C646 inhibitory effects for p300 HAT mutants. All assays used 400 μM H4-15; IC$_{50}$s used 10 μM AcCoA; and apparent Ki = IC$_{50}$/(S/Km + 1).

| variant | $K_{m, AcCoA}$ (μM) | $k_{cat}$ (min$^{-1}$) | $k_{cat}/K_m$ (M$^{-1}$ min$^{-1}$) | IC$_{50}$ (μM) | app. $K_i$ (μM) |
|---|---|---|---|---|---|
| wt | 4.7(±0.6) | 18.8(±0.6) | 4.0(±0.5) · 10$^6$ | 1.6(±0.2) | 0.51 |
| T1411A | 33(±10) | 18(±3) | 5(±2) · 10$^5$ | 3.4(±0.9) | 2.6 |
| Y1467F | 1.9(±0.5) | 0.168(±0.008) | 8.8(±0.2) · 10$^4$ | 7(±2) | 1.1 |
| W1466F | 24(±5) | 64(±6) | 3.0(±0.7) · 10$^6$ | 5.0(±0.5) | 3.5 |
| R1410A | 150(±40) | 13(±3) | 9(±3) · 10$^4$ | 2.5(±0.5) | 2.3 |

Since each of these mutants can alter acetyl-CoA interactions as well, corresponding $K_m$s for acetyl-CoA for the four mutant proteins were measured, and the equation $K_i=IC_{50}/(S/K_{m+1})$ was used to calculate the apparent $K_i$ values based on a competitive inhibition model (Copeland, *Enzymes: A Practical Introduction to Structure, Mechanism, and Data Analysis,* 2000, Wiley-VCH, New York). As shown in Table 3, each mutation increased the apparent $K_i$ of C646 by at least 2-fold, and the most significant effect was seen with W1466F, which showed a 7-fold increase in $K_i$. This increase may reflect a combination of the loss of the hydrogen bond from the indole nitrogen as well as altered Van der Waals contacts. Interestingly, the $K_{cat}/K_m$ for W1466F p300 is essentially identical to the wild type enzyme (Table 3), suggesting that inhibition by C646 and catalysis rely on subtly different forces.

Example 7

Structure-Activity-Relationship Analysis of C646 in p300 Inhibition

To explore structural elements of C646 responsible for inhibition of p300, modular synthetic approaches were employed to prepare a series of analogs that could probe the benzoate, pyrazolone, exomethylene, and arylnitro moieties. The general synthetic approach to prepare many of these analogs involved initially producing the building block phenyl-pyrazolones (3) and the aryl-furan aldehydes (see supra). Production of the phenyl-pyrazolones (3) (Kim et al., *Bull. Korean. Chem. Soc.* 12, 376 (1991)) was achieved from the corresponding anilines 1 which could be diazotized and transformed to the aryl hydrazines (2). Reaction of intermediates 2 with ethyl acetylacetate led to pyrazolones (3) formation. Palladium-catalyzed Suzuki coupling of 5-formyl-2furanboronic acid with aryl halides (4) led to aryl-furan aldehydes (5) (Langner et al., *Chem. Eur. J.* 11, 6254 (2005) and Hosoya et al., *Bioorg. Med. Chem.* 11, 663 (2003)). Knoevenagel condensation between 3 and 5 generated the desired analogs of C646 (Vasyunkina et al., *Russ. J. Org. Chem.* 41, 742 (2005)).

Figure 6:
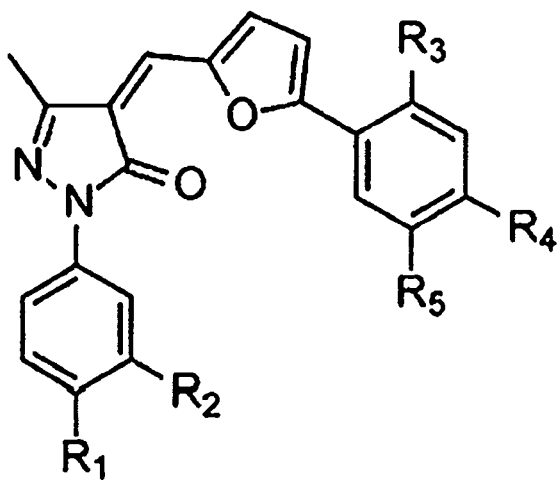
FIG. 6 shows assorted phenyl ring-substituted analogs of C646 and their relative IC$_{50}$s for p300 inhibition referenced to C646.
Figure 7:
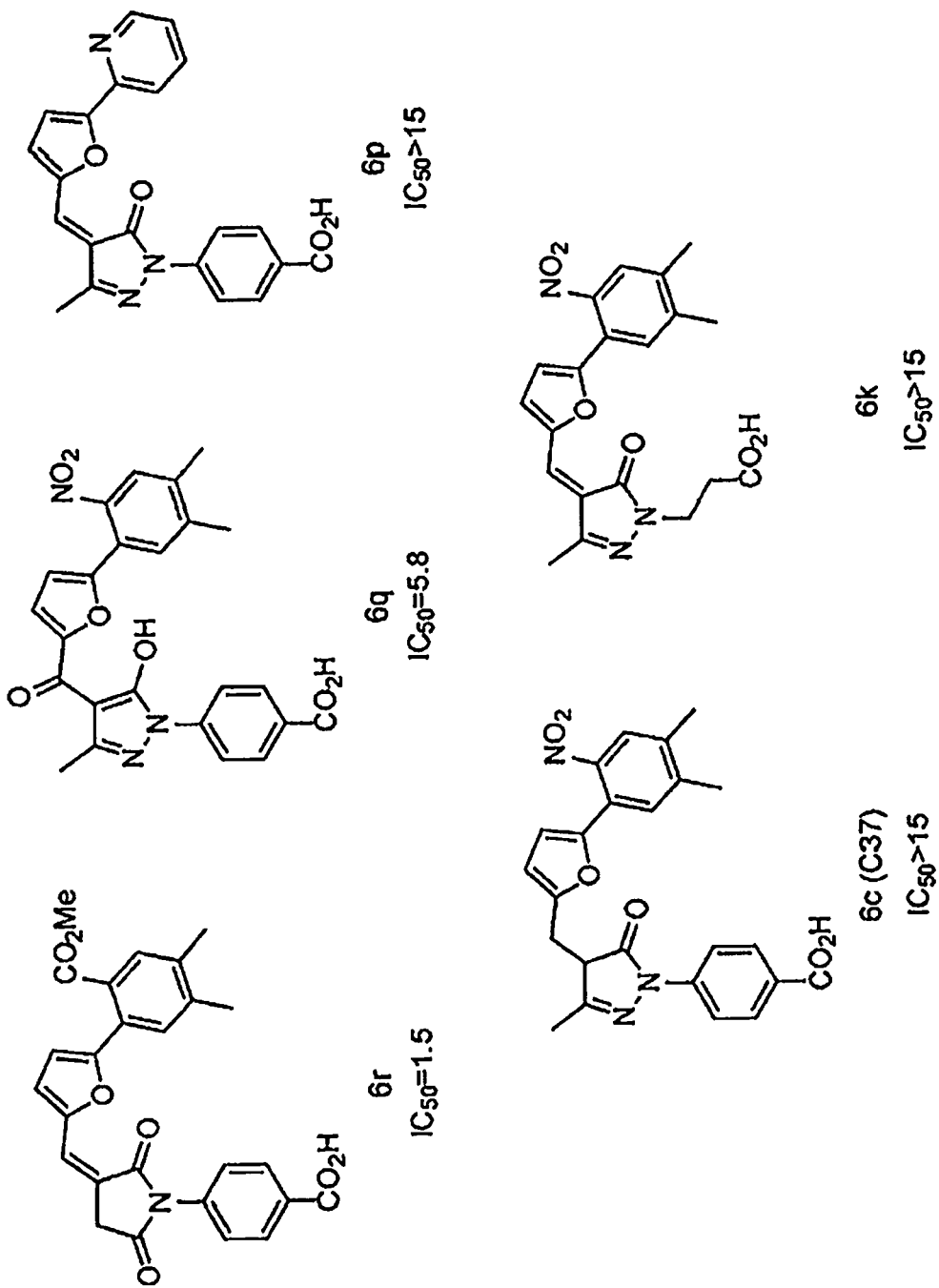
FIG. 7 shows several C646 analogs with replacements of terminal rings, linker modifications, and pyrazolone alterations and their relative IC$_{50}$s for p300 inhibition referenced to C646.

Each of the analogs 6a-r along with two other related commercially available derivatives were tested for p300 HAT inhibition using the direct, 14 C-acetyl-CoA transfer assay at a range of concentrations and the relative $IC_{50}$s are shown in FIGS. 6 and 7. Derivatization of the carboxylic acid of C646 as the methyl ester affording 6h led to a dramatic weakening of inhibitory potency (>15-fold), establishing the likely importance of this functionality in hydrogen bonding. Reduction of the C646 enone with sodium borohydride gives rise to C37 (6c) and this compound did not detectably block p300 HAT activity (FIG. 7). The loss of inhibitory potency of C37 suggests that shape (planarity) and/or electronic properties of the conjugated system in C646 is important. Replacement of the C646 nitro group with hydroxymethylene (6l) also led to a substantial reduction in potency supporting the importance of hydrogen bonding of the nitro predicted by the computational model.

Figure 8:
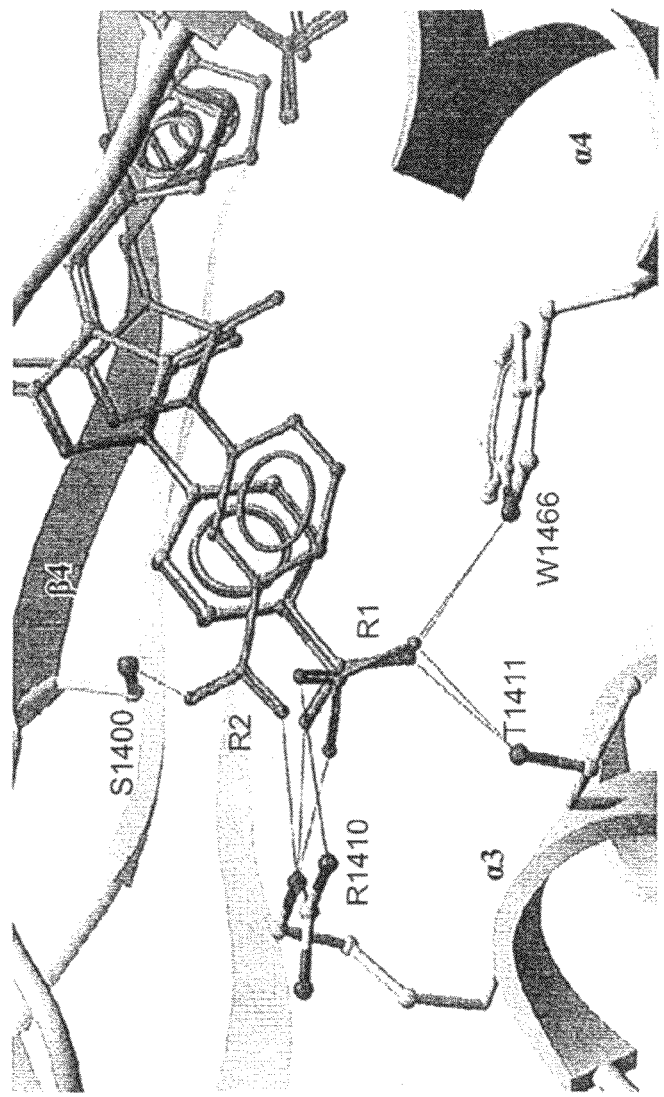
FIG. 8 shows the predicted binding poses of the inhibitors 6e, 6f, and C646 with the crystal structure of p300 HAT. The carbon atoms of 6e, 6f, and C646 are colored magenta, orange and green respectively. The receptor p300 HAT is displayed in grey ribbon with grey carbon atoms. Key hydrogen bond interactions are displayed by black dots and the R groups are labeled. Switching the hydrogen bond acceptor from R1 to R2 results in a slight rotation of the phenyl group and an interaction with Ser1400.

Other hydrogen bond acceptors replacing the C646 para-carboxylic acid were well tolerated at both the para and meta positions including a para-carboxamide (6a), a para-sulfonic acid (6f), a para-sulfonamide (6g), and a meta-methyl ester (6i) or carboxylic acid (6e). Molecular modeling reveals considerable p300 active site flexibility in accommodating these other para- and meta-substituted compounds (FIG. 8). Molecular recognition versatility with regard to nitrophenyl interactions is indicated by the fact that replacement of the nitro group by methylbenzoate (6m) or cyano (6o) functionalities is also well tolerated (FIG. 7). That the nitro group could be effectively replaced by a methylbenzoate might offer pharmacokinetic advantages for in vivo studies. However, replacement of the nitrophenyl ring with a pyridine ring (6p) eliminated p300 inhibitory action.

Replacing the pyrazolone of C646 with a succinimide ring in the context of a methyl benzoate substituent replacing the nitro group (6r) retains potency for p300 inhibition (FIG. 7). Since succinimides related to 6r are believed to exist with a strong preference for E-exomethylene stereochemistry (see Haval and Argade, *J. Org. Chem.* 73, 6963 (2008)), this result further supports the conformational arrangement predicted by the docking model for C646. A propionate group (6k) cannot successfully replace the benzoate ring of C646 and still retain p300 inhibitory potency. Interestingly, carbonyl substitution of the exomethylene vinyl (6q) shows 6-fold weaker potency compared with C646.

Example 8

Effects of C646 on Histone Acetylation in Mouse Cells

The effects of compound C646 on cellular histone acetylation were investigated using cultured cells. Histones in mammalian cells show characteristic rates of turnover of acetylation, with a majority showing slower rates and a very minor fraction showing very fast turnover. This latter fraction has been associated with gene activation, and is defined by rapid hyperacetylation in the presence of deacetylase inhibitors such as Trichostatin A (TSA). In addition to SDS gels (FIG. 9A), Acid-Urea gels (AU, FIG. 9B) were used, on which loss of a positive charge upon lysine acetylation retards migration, producing a ladder of bands corresponding to integral changes in acetylation. The effects of C646 on basal acetylation levels and on the rapidly turning over TSA-sensitive fraction was examined by western blots using modification-specific antibodies against H3K9ac and 1-14K12ac (FIG. 9).

Figure 9A:
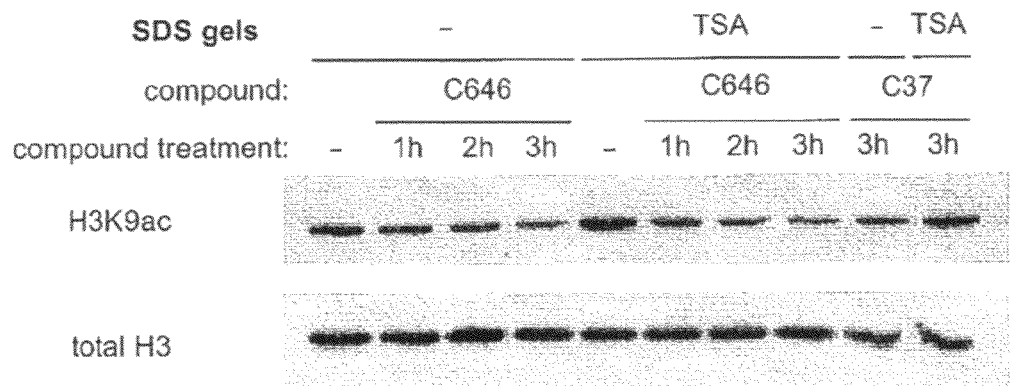
FIGS. 9A and 9B show that C646 treatment reduces histone H3 and H4 acetylation levels and abrogates TSA-induced acetylation in cultured cells. Quiescent C3H 10T1/2 mouse fibroblasts were pretreated with C646 (25 uM, lanes 2-4 and 6-8) for the indicated times (1, 2, or 3 hours) or the control compound, C37 (25 uM, 3 hours, lanes 9 and 10). TSA (33 nM) was added where indicated (lanes 6-8 and 10) for the final 30 min of incubation.
Figure 9B:
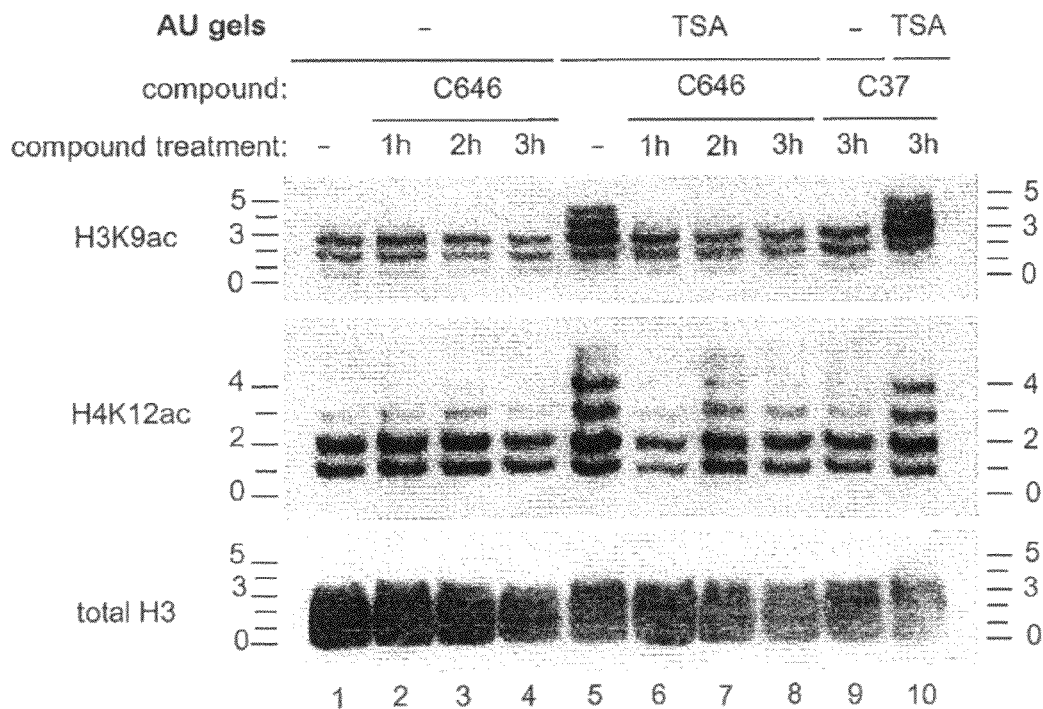

In control cells, basal acetylation levels of H3 and H4 are slightly diminished by C646 over the 1-3 hours time-course tested (FIGS. 9A and 9B; lanes 1-4). Upon 30 minutes of TSA treatment, acetylation of H3 and H4 was increased, very evident from the appearance of higher migrating forms on AU gels (FIGS. 9A and 9B; compare lanes 1 and 5). At all timepoints tested (1-3 hours; lanes 6-8), this TSA-inducible acetylation of histones H3 and H4 is virtually completely inhibited by C646.

By contrast, 3 hours treatment with the C646 analog C37, which is devoid of p300 HAT inhibitory activity, produced no effect on acetylation of H3 or H4 (FIGS. 9A and 9B; lanes 9, 10). Thus, the effect of C646 on basal histone acetylation over 3 hours is small but detectable, whereas its effect on TSA-sensitive acetylation is strikingly clear, arguing that p300/CBP mediates the rapidly turning over component of acetylation.

Example 9

Cell Growth Effects of C646 on Melanoma, Lung, and Brain Cancer Cells

Given the broad and important effects of p300/CBP HAT on key genes and pathways involved in cell growth, the pharmacologic effects of C646 in three melanoma and three non-small cell lung cancer lines was assessed by $^3$H-thymidine incorporation at 24 hours after treatment (FIG. 10). C646 (10 µM) and the peptide-based bisubstrate p300/CBP HAT inhibitor Lys-CoA-Tat (25 µM) were tested. Both compounds were capable of reducing $^3$H-thymidine incorporation in several of these human cancer lines to varying degrees (FIG. 10). In general, reduction of $^3$H-thymidine incorporation was correlated for Lys-CoA-Tat and C646 among the different cell lines, consistent with a common protein target, presumed to be p300/CBP HAT, although C646 generally showed greater effects at the doses used.

Figure 11:
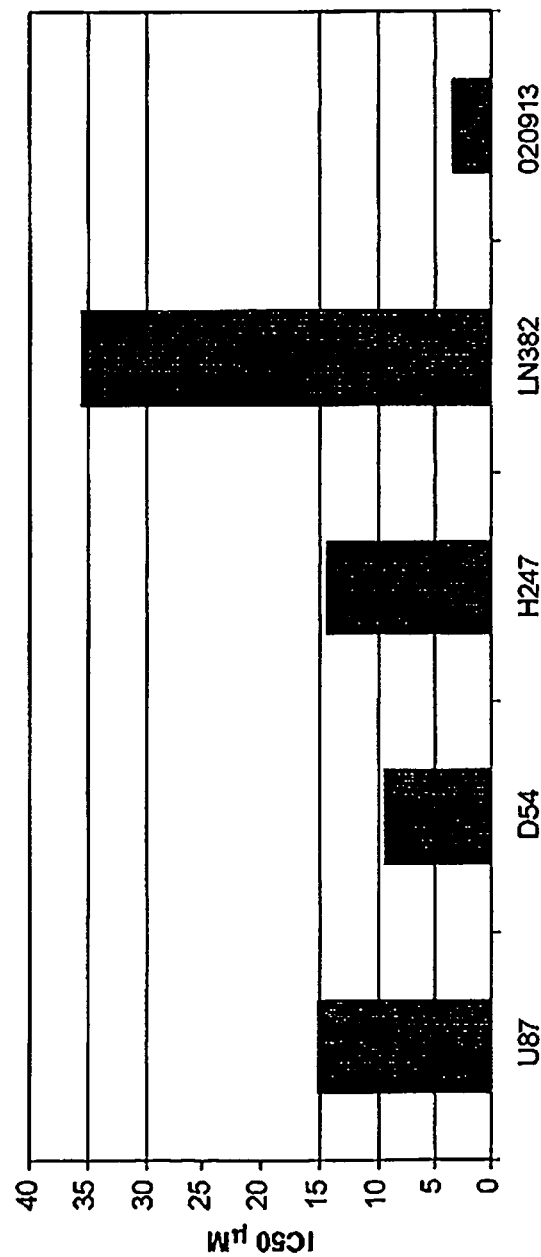
FIG. 11 is a graph showing the growth inhibitory effect of C646 on glioblastoma cells. U87, D54, H247, LN382, and 020913 glioblastoma cells were treated with varying doses of C646 for 72 hours. Dose response curves were generated using the AlamarBlue® assay (Invitrogen, Carlsbad, Calif.). Four out of five glioblastoma cell lines demonstrated significant inhibition after C646 treatment. The $IC_{50}$ of C646 were as follows: LN382=35.5 µM, U87=15.1 µM, H247=14.4 µM, D54=9.3 µM, and 020913=3.4 µM.

The inhibitory effect of C646 was also observed in the glioblastoma cell lines U87, D54, H247, LN382, and 020913 (FIG. 11). C646 was capable of significantly reducing ³H-thymidine incorporation in four of the five glioblastoma cell lines, and the $IC_{50}$ of C646 for the glioblastoma cell lines ranged from 35.5 μM to 3.4 μM.

Figure 12:
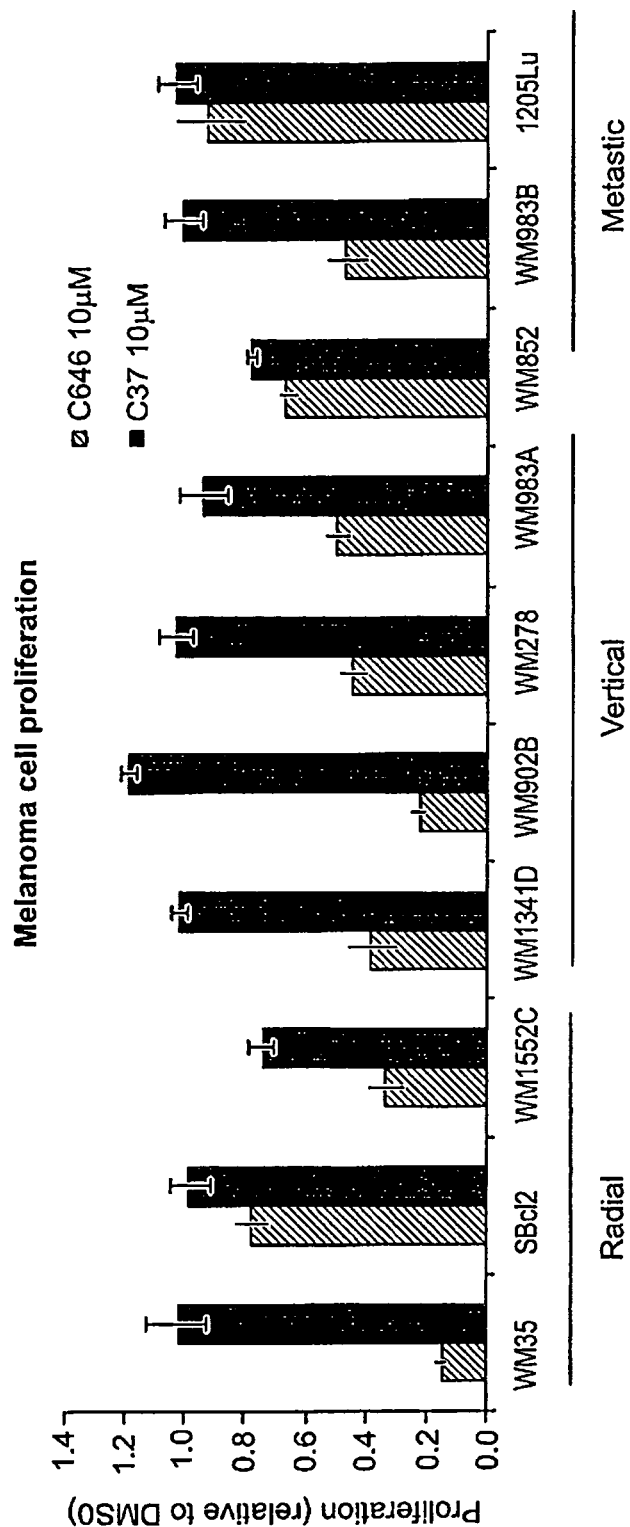
FIG. 12 is a graph showing the growth inhibitory effect of C646 on melanoma cell lines from varying stages of progression. Radial growth (WM5, SBc12, and WM1552C), vertical growth (WM1341D, WM902B, WM278, and WM983A), and metastatic growth (WM852, WM983B, and 1205Lu) melanoma cells were treated with C646 for 24 hours. Proliferation was measured via $^3$H-thymidine incorporation.

Next, C646 was screened with 12 melanoma cell lines from varying stages of progression (FIG. 12). In general, treated cells demonstrated reduced ³H-thymidine incorporation. This data is consistent with the above-described findings and indicates that C646 has a growth effect on tumor cells even at varying stages of disease progression.

Example 10

C646 Inhibits the Cell Growth of a Broad Range of Tumor Cell Lines

The effect of C646 was assessed on the NCI-60 panel of tumor cell lines (http://dtp.cancer.gov/branches/btb/ivclsp.html). In these studies, leukemia cells, lung cancer cells, colon cancer cells, CNS cancer cells, melanoma cells, ovarian cancer cells, renal cancer cells, and prostate cancer cells demonstrated significant growth inhibition and/or tumor cell death after treatment with C646 (FIG. 13). These results confirm that C646 has growth inhibitory effects across a wide range of cancers, likely because the biologic functions of p300/CBP HAT affect a variety of processes involved in tumoriogenesis.

Example 11

C646 Induces Cellular Apoptosis and/or Senescence

Figure 14A:
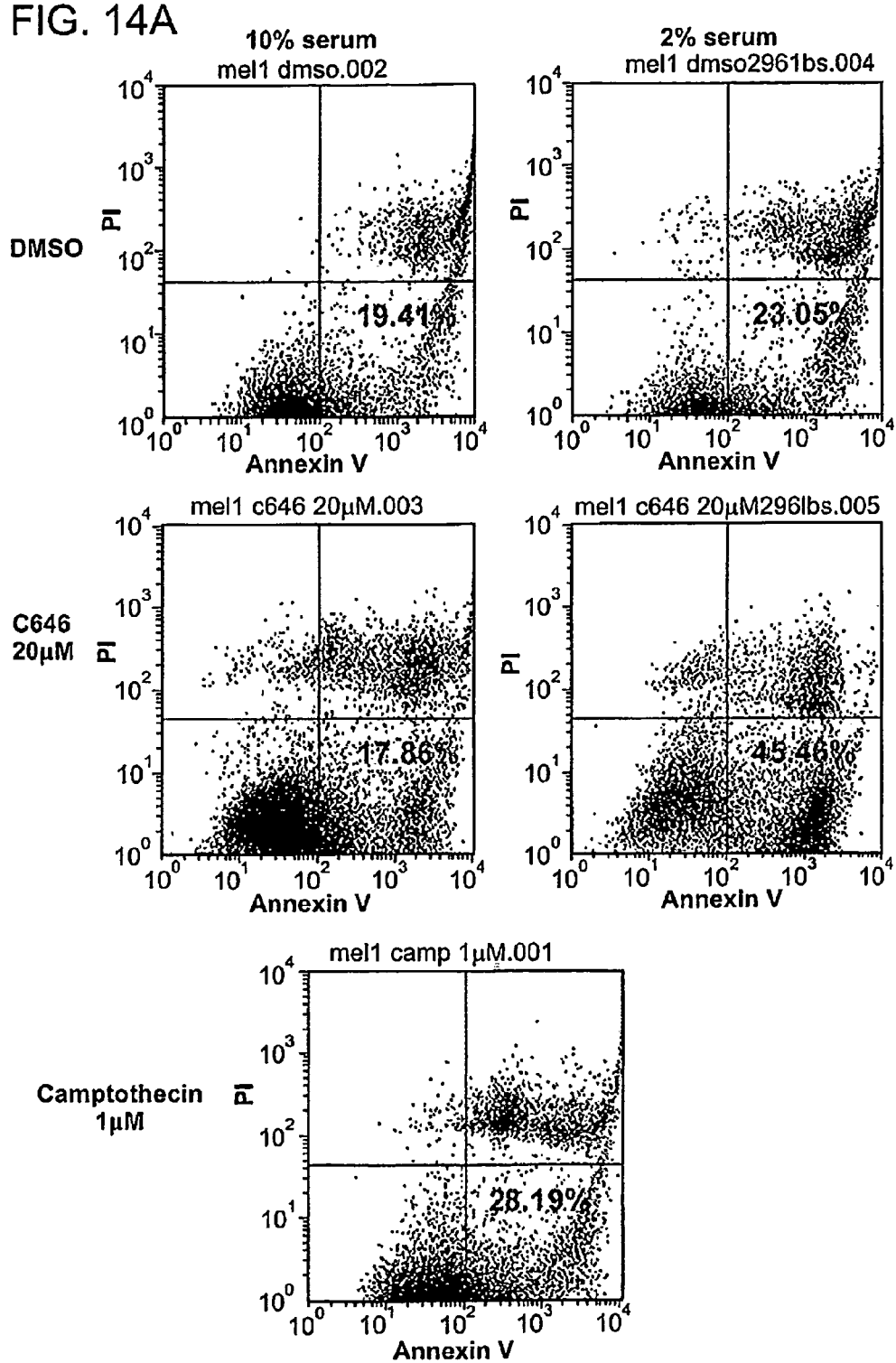

The effects of C646 on tumor cell apoptosis was evaluated. WM35 melanoma cells were treated with C646 or DMSO (control) for 72 hours, stained with annexin V and propidium iodide, and assessed by FACS. At low serum concentrations, C646 induced WM35 cell apoptosis (FIG. 14A).

As senescence is believed to be a tumor suppressive mechanism, C646 was also assessed for its ability to induce senescence in tumor cell. After treating WM35 melanoma cells with C646 for 72 hours, the cells were stained for senescence-associated beta galactosidase. In these experiments, C646 induced sensecence in WM35 cells under low and high serum concentrations (FIGS. 14B and C).

Example 12

Effects of C646 on the Cell Cycle

In the moderately sensitive melanoma line WM983A, the $IC_{50}$ for C646 was in the range of 10-20 μM. However, this cell line was resistant to the C646 analog control compound C37 at 20 μM (FIG. 15A). Consistent with the histone H3 acetylation data above (see FIG. 9), the growth effect of C646 on WM983A cells corresponded to a dose-dependent reduction in global histone H3 acetylation (FIG. 15B).

Figure 15D:
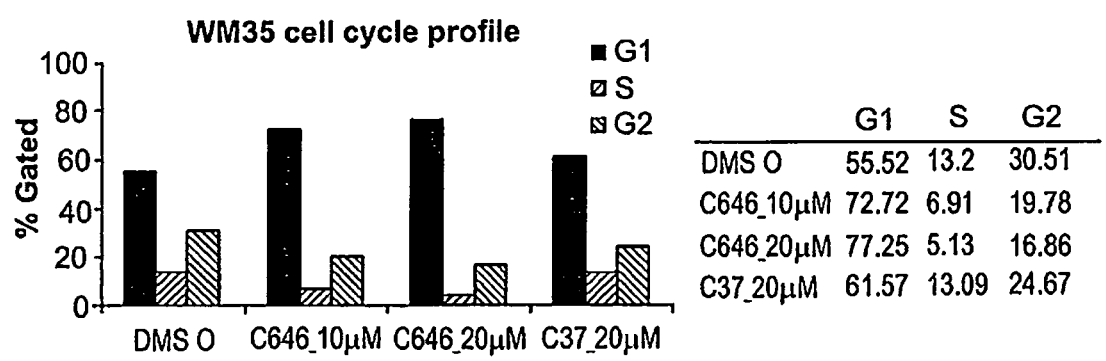
Figure 15E:
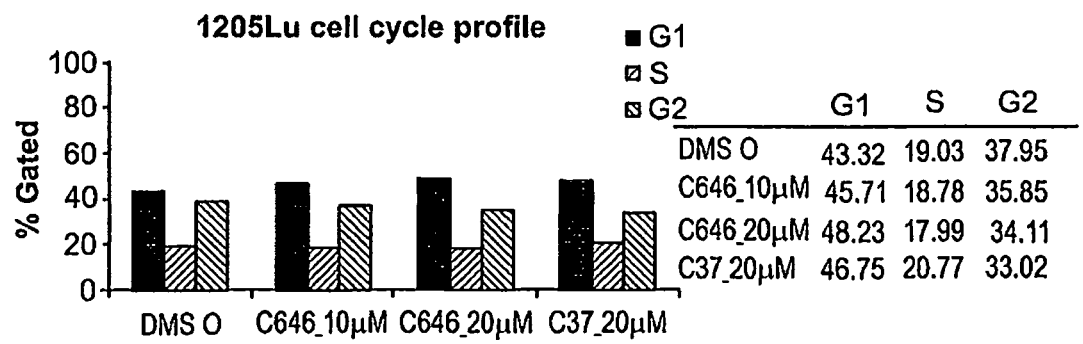

WM983A cells were then used to asses the effect of C646 on the cell cycle. WM983 melanoma cells were treated with C646, stained with propidium iodide, and then analyzed by FACS. Treatment with C646 decreased the number of cells in S and G2 phase (FIG. 15C), indicating that C646 induces G1-S cell cycle arrest in melanoma cells. These results were also observed in two other melanoma cell lines (FIGS. 15D and 15E). The degree of growth arrest observed in these experiments corresponds with the decrease in ³H-thymidine incorporation described above.

Example 13

Effects of C646 in Combination with Traditional Chemotherapies

Figure 16A:
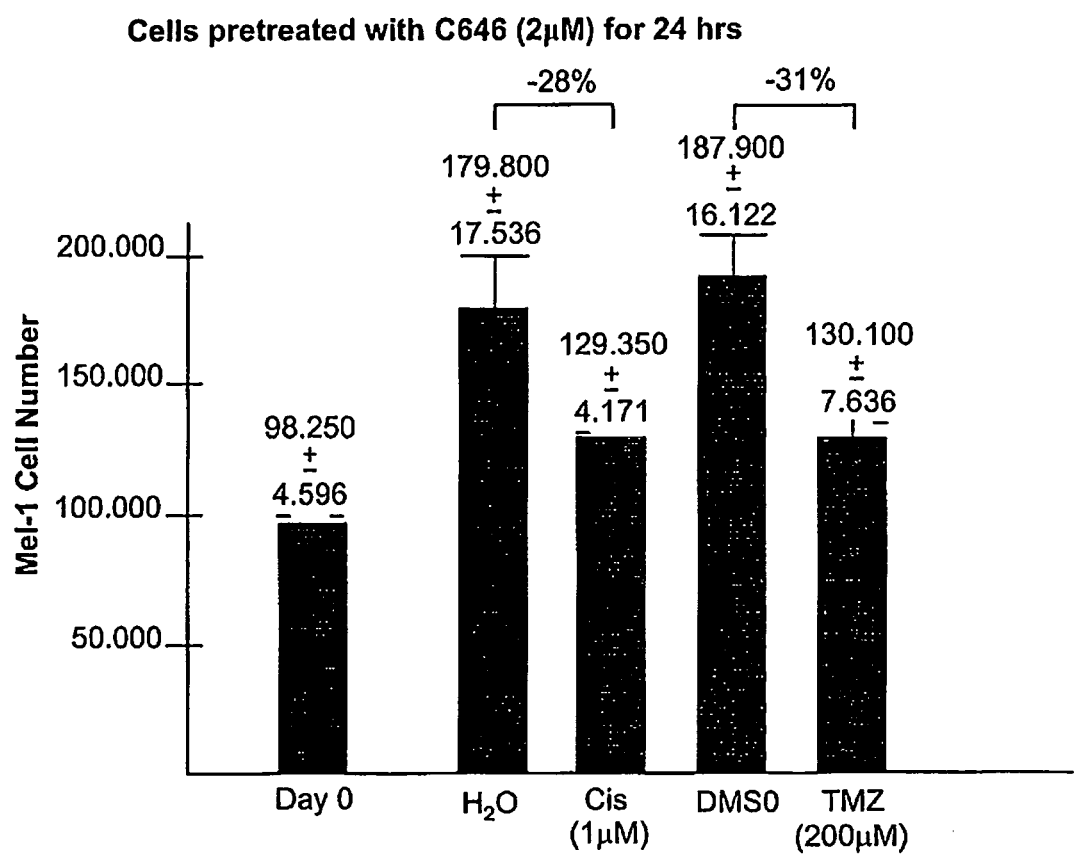
FIGS. 16A and 16B relate to the use of C646 as an antiproliferative agent in combination therapies to treat tumor cells.
Figure 16B:
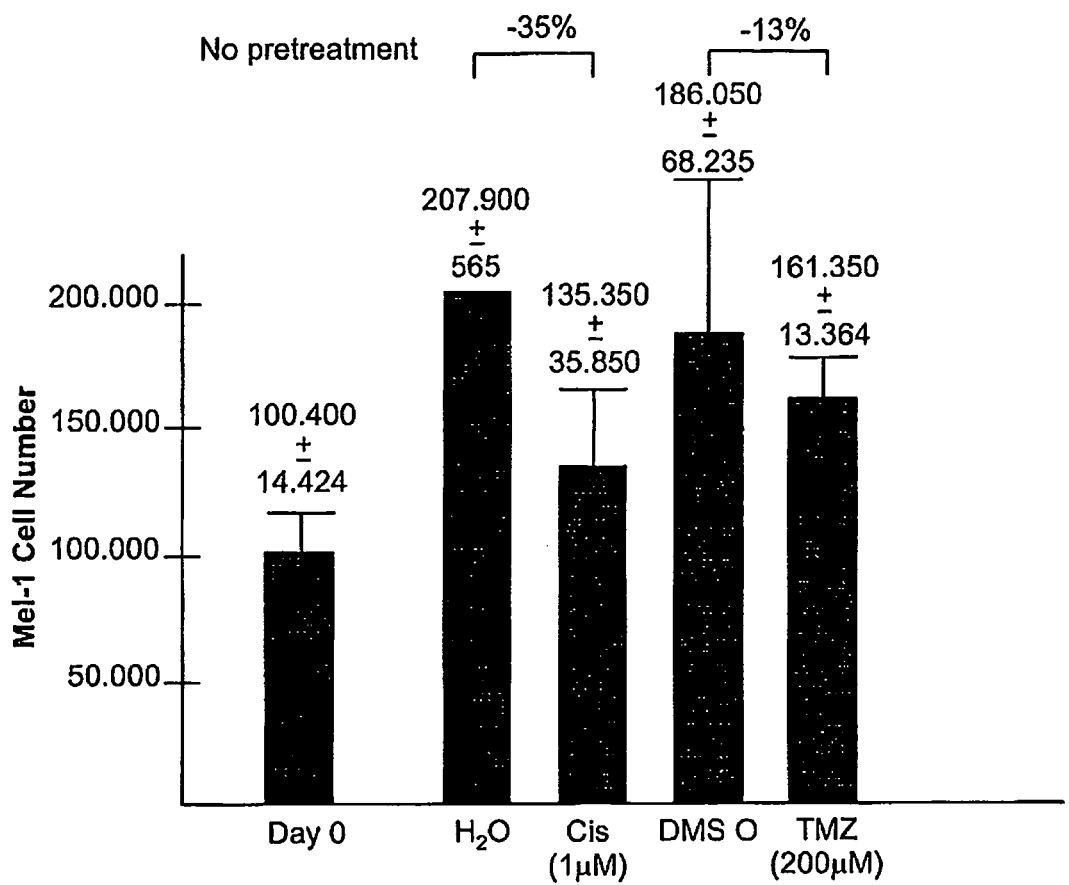

To evaluate the effectiveness of C646 as an anti-cancer agent for use in combination therapy, the effects of C646 in combination with known anti-cancer agents in a melanoma cell line was assessed. Prior to treatment with either 1 μM cisplatin or 200 μM of temozolamide, known anti-cancer agents that induce DNA damage, Mel-1 melanoma cells was treated with either 2 μM C646 or diluent. After 24 hours, the treated and mock-treated cells were given fresh medium, and the cells were treated with cisplatin or temozolamide for 48 hours. In the mock-treated cells, cisplatin caused a 35% decrease in cell number and temozolamide caused a 13% decrease in cell number (FIG. 16B). In the C646 treated cells, cisplatin caused a 28% decrease in cell number and temozolamide caused a 31% decrease in cell number (FIG. 16A). The doses of both the chemotherapy agents and the C646 used in these experiments are significantly lower than would be used to block tumor growth if given alone. However, even at these lower levels, these results indicate that C646 sensitized the melanoma cells to temozolamide.

Example 14

WM35 Microarray Analysis to Identify p300 Target Genes

Microarray analysis was performed on WM35 melanoma cells treated with C646 in order to identify the downstream effectors of p300 HAT. WM35 melanoma cells were treated with 20 μM C646 or DMSO (control). Cellular mRNA was harvested at 6 hours and 24 hours after treatment and analyzed on the Affymetrix Human Exon Array (Affymetrix, Santa Clara, Calif.) in accordance with the manufacturer's instructions. The results are presented below in Tables 4-6 using GO (Gene Ontology) annotations, and each gene identified in these tables are markers for p300/CBP HAT inhibition.

TABLE 4

Genes associated with biological processes that were down-regulated by more than 2-fold at 24 hours.

| Transcript ID | UniqueGene Symbol | UniqueGene Title | Linear Fold Change |
|---|---|---|---|
| Negative regulation of mitotic metaphase/anaphase transition (n = 5 of 10) p = 8.9e−7 | | | |
| 2780172 | CENPE | centromere protein E, 312 kDa | −5.33076 |
| 2783715 | MAD2L1 | MAD2 mitotic arrest deficient-like 1 (yeast) | −2.8502 |
| 2570616 | BUB1 | budding uninhibited by benzimidazoles 1 homolog (yeast) | −4.79734 |
| 2914777 | TTK | TTK protein kinase | −6.05127 |

TABLE 4-continued

Genes associated with biological processes that were down-regulated by more than 2-fold at 24 hours.

| Transcript ID | UniqueGene Symbol | UniqueGene Title | Linear Fold Change |
|---|---|---|---|
| 2379863 | CENPF | centromere protein F, 350/400 ka (mitosin) | −6.46074 |
| Regulation of cell cycle (n = 42 of 293 p = 2.12e−23) | | | |
| 3527039 | NEK2 | NIMA (never in mitosis gene a)-related kinase 2 | −2.12968 |
| 2980241 | FBXO5 | F-box protein 5 | −3.68922 |
| 2877378 | CDC25C | cell division cycle 25 homolog C (S. pombe) | −2.24976 |
| 3758317 | BRCA1 | breast cancer 1, early onset | −2.37871 |
| 2335922 | CDKN2C | cyclin-dependent kinase inhibitor 2C (p18, inhibits CDK4) | −2.10838 |
| 3435362 | KNTC1 | kinetochore associated 1 | −3.47361 |
| 2997376 | ANLN | anillin, actin binding protein | −4.0782 |
| 2780172 | CENPE | centromere protein E, 312 kDa | −5.33076 |
| 3440598 | FOXM1 | forkhead box M1 | −2.12038 |
| 3881443 | TPX2 | TPX2, microtubule-associated, homolog (*Xenopus laevis*) | −3.15849 |
| 2673085 | CDC25A | cell division cycle 25 homolog A (*S. pombe*) | −9.29544 |
| 2783715 | MAD2L1 | MAD2 mitotic arrest deficient-like 1 (yeast) | −2.8502 |
| 2784113 | CCNA2 | cyclin A2 | −7.24263 |
| 2454444 | NEK2 | NIMA (never in mitosis gene a)-related kinase 2 | −3.24327 |
| 3887049 | UBE2C | ubiquitin-conjugating enzyme E2C | −4.8011 |
| 2898597 | GMNN | geminin, DNA replication inhibitor | −2.30648 |
| 2570616 | BUB1 | budding uninhibited by benzimidazoles 1 homolog (yeast) | −4.79734 |
| 3903146 | E2F1 | E2F transcription factor 1 | −2.97126 |
| 2914777 | TTK | TTK protein kinase | −6.05127 |
| 3565663 | DLGAP5 | discs, large (*Drosophila*) homolog-associated protein 5 | −3.54451 |
| 3677315 | PKMYT1 | protein kinase, membrane associated tyrosine/threonine 1 | −2.824 |
| 3457824 | TIMELESS | timeless homolog (*Drosophila*) | −2.84061 |
| 4009238 | SMC1A | structural maintenance of chromosomes 1A | −2.89684 |
| 2813414 | CCNB1 | cyclin B1 | −3.63587 |
| 3354799 | CHEK1 | CHK1 checkpoint homolog (*S. pombe*) | −2.47119 |
| 2714955 | TACC3 | transforming, acidic coiled-coil containing protein 3 | −2.50701 |
| 3145107 | CCNE2 | cyclin E2 | −12.7005 |
| 3257338 | KIF20B | kinesin family member 20B | −4.90034 |
| 2379863 | CENPF | centromere protein F, 350/400 ka (mitosin) | −6.46074 |
| 3699044 | RFWD3 | ring finger and WD repeat domain 3 | −2.96289 |
| 3590388 | NUSAP1 | nucleolar and spindle associated protein 1 | −5.76382 |
| 3589697 | BUB1B | budding uninhibited by benzimidazoles 1 homolog beta (yeast) | −6.07233 |
| 3484641 | BRCA2 | breast cancer 2, early onset | −4.19528 |
| 3607698 | C15orf42 | chromosome 15 open reading frame 42 | −11.1325 |
| 3608298 | BLM | Bloom syndrome, RecQ helicase-like | −5.26511 |
| 3598721 | ZWILCH | Zwilch, kinetochore associated, homolog (*Drosophila*) | −2.57407 |
| 2401448 | E2F2 | E2F transcription factor 2 | −2.01079 |
| 3720896 | CDC6 | cell division cycle 6 homolog (*S. cerevisiae*) | −6.58374 |
| 3949055 | GTSE1 | G-2 and S-phase expressed 1 | −3.47294 |
| 2742985 | PLK4 | polo-like kinase 4 (*Drosophila*) | −4.84879 |
| 3178583 | CKS2 | CDC28 protein kinase regulatory subunit 2 | −2.18977 |
| 3290210 | ZWINT | ZW10 interactor | −4.05133 |
| 3415857 | ESPL1 | extra spindle pole bodies homolog 1 (*S. cerevisiae*) | −4.82445 |

TABLE 4-continued

Genes associated with biological processes that were down-regulated by more than 2-fold at 24 hours.

| Transcript ID | UniqueGene Symbol | UniqueGene Title | Linear Fold Change |
|---|---|---|---|
| Regulation of chromosome segregation (n = 5 of 8 p = 2.05e−7) | | | |
| 2334098 | KIF2C | kinesin family member 2C | −6.03185 |
| 2780172 | CENPE | centromere protein E, 312 kDa | −5.33076 |
| 2570616 | BUB1 | budding uninhibited by benzimidazoles 1 homolog (yeast) | −4.79734 |
| 2813414 | CCNB1 | cyclin B1 | −3.63587 |
| 3415857 | ESPL1 | extra spindle pole bodies homolog 1 (*S. cerevisiae*) | −4.82445 |
| Regulation of microtubule-based process (n = 9 of 41 p = 1.31e−7) | | | |
| 3188249 | SKA2 | spindle and kinetochore associated complex subunit 2 | −2.33361 |
| 3758317 | BRCA1 | breast cancer 1, early onset | −2.37871 |
| 2780172 | CENPE | centromere protein E, 312 kDa | −5.33076 |
| 3881443 | TPX2 | TPX2, microtubule-associated, homolog (*Xenopus laevis*) | −3.15849 |
| 3788049 | SKA1 | spindle and kinetochore associated complex subunit 1 | −8.88142 |
| 2813414 | CCNB1 | cyclin B1 | −3.63587 |
| 2714955 | TACC3 | transforming, acidic coiled-coil containing protein 3 | −2.50701 |
| 3504617 | SKA3 | spindle and kinetochore associated complex subunit 3 | −3.27735 |
| 2742985 | PLK4 | polo-like kinase 4 (*Drosophila*) | −4.84879 |
| G2/M transition DNA damage checkpoint (n = 3 of 12 p = 0.002) | | | |
| 3758317 | BRCA1 | breast cancer 1, early onset | −2.37871 |
| 2784113 | CCNA2 | cyclin A2 | −7.24263 |
| 3608298 | BLM | Bloom syndrome, RecQ helicase-like | −5.26511 |
| Nucleosome assembly (n = 24 of 83 p = 2.88e−21) | | | |
| 2434084 | HIST2H2AA3 | histone cluster 2, H2aa3 | −2.07525 |
| 2434129 | HIST2H2AB | histone cluster 2, H2ab | −5.65857 |
| 2900059 | HIST1H2BM | histone cluster 1, H2bm | −11.4992 |
| 2459616 | HIST3H2A | histone cluster 3, H2a | −3.58974 |
| 2899756 | HIST1H2AG | histone cluster 1, H2ag | −2.24798 |
| 2793951 | HMGB2 | high-mobility group box 2 | −5.26891 |
| 2357927 | HIST2H2AA3 | histone cluster 2, H2aa3 | −2.03936 |
| 2357952 | HIST2H2AC | histone cluster 2, H2ac | −3.5962 |
| 2473991 | CENPA | centromere protein A | −3.07267 |
| 3920003 | CHAF1B | chromatin assembly factor 1, subunit B (p60) | −2.83967 |
| 2604254 | HJURP | Holliday junction recognition protein | −5.26841 |
| 3923211 | HIST1H2BK | histone cluster 1, H2bk | −3.82499 |
| 3817501 | CHAF1A | chromatin assembly factor 1, subunit A (p150) | −2.92758 |
| 2946194 | HIST1H1A | histone cluster 1, H1a | −3.52987 |
| 2946219 | HIST1H2AB | histone cluster 1, H2ab | −3.96333 |
| 2946225 | HIST1H2BB | histone cluster 1, H2bb | −29.1029 |
| 2946232 | HIST1H1C | histone cluster 1, H1c | −2.30194 |
| 2946353 | HIST1H1D | histone cluster 1, H1d | −5.13795 |
| 2946364 | HIST1H3F | histone cluster 1, H3f | −4.97752 |
| 2947032 | HIST1H2BL | histone cluster 1, H2bl | −4.60451 |
| 2947063 | HIST1H2AK | histone cluster 1, H2ak | −2.11695 |
| 2947073 | HIST1H1B | histone cluster 1, H1b | −9.77338 |
| 3394183 | H2AFX | H2A histone family, member X | −2.55817 |
| 2640855 | MCM2 | minichromosome maintenance complex component 2 | −3.44801 |
| 3852565 | ASF1B | ASF1 anti-silencing function 1 homolog B (*S. cerevisiae*) | −2.66808 |
| DNA replication-dependent nucleosome assembly (n = 2 of 2 p = 4.35e−4) | | | |
| 3920003 | CHAF1B | chromatin assembly factor 1, subunit B (p60) | −2.83967 |
| 3817501 | CHAF1A | chromatin assembly factor 1, subunit A (p150) | −2.92758 |
| Centromere complex assembly (n = 5 of 7 p = 7.81e−8) | | | |
| 2780172 | CENPE | centromere protein E, 312 kDa | −5.33076 |
| 2473991 | CENPA | centromere protein A | −3.07267 |

TABLE 4-continued

Genes associated with biological processes that were down-regulated by more than 2-fold at 24 hours.

| Transcript ID | UniqueGene Symbol | UniqueGene Title | Linear Fold Change |
|---|---|---|---|
| 2604254 | HJURP | Holliday junction recognition protein | −5.26841 |
| 3258910 | HELLS | helicase, lymphoid-specific | −4.93465 |
| 2379863 | CENPF | centromere protein F, 350/400 ka (mitosin) | −6.46074 |
| Establishment of organelle localization n = 11 of 63 p = 6.46e−8) | | | |
| 2780172 | CENPE | centromere protein E, 312 kDa | −5.33076 |
| 3776139 | NDC80 | NDC80 homolog, kinetochore complex component (*S. cerevisiae*) | −5.86358 |
| 3565663 | DLGAP5 | discs, large (*Drosophila*) homolog-associated protein 5 | −3.54451 |
| 2813414 | CCNB1 | cyclin B1 | −3.63587 |
| 2473991 | CENPA | centromere protein A | −3.07267 |
| 3367338 | KIF18A | kinesin family member 18A | −5.26888 |
| 2379863 | CENPF | centromere protein F, 350/400 ka (mitosin) | −6.46074 |
| 3590388 | NUSAP1 | nucleolar and spindle associated protein 1 | −5.76382 |
| 3377423 | CDCA5 | cell division cycle associated 5 | −6.85864 |
| 2840002 | CCDC99 | coiled-coil domain containing 99 | −2.47696 |
| 3415857 | ESPL1 | extra spindle pole bodies homolog 1 (*S. cerevisiae*) | −4.82445 |

TABLE 5

Genes associated with biological processes that were up-regulated by more than 2-fold at 24 hours.

| Transcript ID | UniqueGene Symbol | UniqueGene Title | Linear Fold Change |
|---|---|---|---|
| Anti-apoptosis (n = 6 of 227 p = 3e−3) | | | |
| 3474495 | TRIAP1 | TP53 regulated inhibitor of apoptosis 1 | 2.21878 |
| 2375664 | BTG2 | BTG family, member 2 | 3.08721 |
| 3257098 | FAS | Fas (TNF receptor superfamily, member 6) | 2.34672 |
| 3838067 | BAX | BCL2-associated X protein | 2.00228 |
| 3628469 | RPS27L | ribosomal protein S27-like | 2.12746 |
| 2976768 | CITED2 | Cbp/p300-interacting transactivator, with Glu/Asp-rich carboxy-terminal domain, 2 | 2.9498 |
| Positive regulation of proteasomal ubiquitin-dependent protein catabolic process (n = 2 of 12 p = 2.57e−3) | | | |
| 3421300 | MDM2 | Mdm2 p53 binding protein homolog (mouse) | 2.7944 |
| 3979478 | MDM2 | Mdm2 p53 binding protein homolog (mouse) | 2.79302 |
| 3738676 | CSNK1D | casein kinase 1, delta | 2.24697 |
| Positive regulation of cell death (n = 8 of 436 p = 6.82e−3) | | | |
| 2544201 | TP53I3 | tumor protein p53 inducible protein 3 | 2.48933 |
| 2450855 | PHLDA3 | pleckstrin homology-like domain, family A, member 3 | 2.73462 |
| 3455056 | ACVR1B | activin A receptor, type IB | 2.05263 |
| 3458587 | DDIT3 | DNA-damage-inducible transcript 3 | 2.25552 |
| 3145149 | TP53INP1 | tumor protein p53 inducible nuclear protein 1 | 2.15852 |
| 3257098 | FAS | Fas (TNF receptor superfamily, member 6) | 2.34672 |
| 3838067 | BAX | BCL2-associated X protein | 2.00228 |
| 3628469 | RPS27L | ribosomal protein S27-like | 2.12746 |

TABLE 6

Genes associated with molecular functions that were up-regulated by more than 2-fold at 24 hours.

| Transcript ID | Gene Symbol | UniqueGene Title | Linear Fold Change |
|---|---|---|---|
| \multicolumn{4}{c}{Chromatin binding (n = 13 of 147 p = 6.64e−6)} | | | |
| 3972093 | POLA1 | polymerase (DNA directed), alpha 1, catalytic subunit | −2.6 |
| 3756193 | TOP2A | topoisomerase (DNA) II alpha 170 kDa | −6.6 |
| 3976797 | SUV39H1 | suppressor of variegation 3-9 homolog 1 (*Drosophila*) | −2.4 |
| 4009238 | SMC1A | structural maintenance of chromosomes 1A | −2.9 |
| 2473991 | CENPA | centromere protein A | −3.1 |
| 3920003 | CHAF1B | chromatin assembly factor 1, subunit B (p60) | −2.8 |
| 3817501 | CHAF1A | chromatin assembly factor 1, subunit A (p150) | −2.9 |
| 3258910 | HELLS | helicase, lymphoid-specific | −4.9 |
| 2379863 | CENPF | centromere protein F, 350/400 ka (mitosin) | −6.5 |
| 3479181 | POLE | polymerase (DNA directed), epsilon | −2.6 |
| 3377423 | CDCA5 | cell division cycle associated 5 | −6.9 |
| 3607698 | C15orf42 | chromosome 15 open reading frame 42 | −11.1 |
| 3720896 | CDC6 | cell division cycle 6 homolog (*S. cerevisiae*) | −6.6 |
| \multicolumn{4}{c}{Kinetochore binding (n = 3 of 4 p = 2.96e−5)} | | | |
| 2780172 | CENPE | centromere protein E, 312 kDa | −5.33076 |
| 2813442 | CENPH | centromere protein H | −2.49351 |
| 2840002 | CCDC99 | coiled-coil domain containing 99 | −2.47696 |
| \multicolumn{4}{c}{Damaged DNA binding (n = 7 of 44 p = 2.17e−5)} | | | |
| 3204463 | FANCG | Fanconi anemia, complementation group G | −2.96713 |
| 3091554 | ESCO2 | establishment of cohesion 1 homolog 2 (*S. cerevisiae*) | −3.60042 |
| 2346369 | FEN1 | flap structure-specific endonuclease 1 | −3.52017 |
| 2691575 | POLQ | polymerase (DNA directed), theta | −2.45356 |
| 3590086 | RAD51 | RAD51 homolog (RecA homolog, *E. coli*) (*S. cerevisiae*) | −5.55326 |
| 3394183 | H2AFX | H2A histone family, member X | −2.55817 |
| 2752725 | NEIL3 | nei endonuclease VIII-like 3 (*E. coli*) | −5.16466 |
| \multicolumn{4}{c}{DNA bending activity (n = 3 of 12 p = 1.45e−3)} | | | |
| 3987679 | HMGB3 | high-mobility group box 3 | −2.66664 |
| 2793951 | HMGB2 | high-mobility group box 2 | −5.26891 |
| 2364631 | HMGB3 | high-mobility group box 3 | −2.13779 |
| 2586464 | HMGB1 | high-mobility group box 1 | −2.0625 |
| \multicolumn{4}{c}{DNA clamp loader activity (n = 3 of 5 p = 7.29e−5)} | | | |
| 3433747 | RFC5 | replication factor C (activator 1) 5, 36.5 kDa | −2.27939 |
| 3485074 | RFC3 | replication factor C (activator 1) 3, 38 kDa | −2.61579 |
| 3056414 | RFC2 | replication factor C (activator 1) 2, 40 kDa | −2.64783 |
| \multicolumn{4}{c}{Structure-specific DNA binding (n = 13 of 138 p = 3.29e−6)} | | | |
| 3097152 | MCM4 | minichromosome maintenance complex component 4 | −6.42724 |
| 2346369 | FEN1 | flap structure-specific endonuclease 1 | −3.52017 |
| 2793951 | HMGB2 | high-mobility group box 2 | −5.26891 |
| 3347340 | RECQL | RecQ protein-like (DNA helicase Q1-like) | −3.20889 |
| 2577896 | MCM6 | minichromosome maintenance complex component 6 | −3.7336 |
| 3590086 | RAD51 | RAD51 homolog (RecA homolog, *E. coli*) (*S. cerevisiae*) | −5.55326 |

TABLE 6-continued

Genes associated with molecular functions that were
up-regulated by more than 2-fold at 24 hours.

| Transcript ID | Gene Symbol | UniqueGene Title | Linear Fold Change |
|---|---|---|---|
| 3484641 | BRCA2 | breast cancer 2, early onset | −4.19528 |
| 2388219 | EXO1 | exonuclease 1 | −5.71068 |
| 3608298 | BLM | Bloom syndrome, RecQ helicase-like | −5.26511 |
| 3158767 | RECQL4 | RecQ protein-like 4 | −2.22859 |
| 2403301 | RPA2 | replication protein A2, 32 kDa | −2.57737 |
| 3401804 | RAD51AP1 | RAD51 associated protein 1 | −7.29048 |
| 3063685 | MCM7 | minichromosome maintenance complex component 7 | −3.27131 |
| ATP binding (n = 76 of 1469 p = 1.43e−15) | | | |
| 3527039 | NEK2 | NIMA (never in mitosis gene a)-related kinase 2 | −2.12968 |
| 2650199 | SMC4 | structural maintenance of chromosomes 4 | −2.79417 |
| 3080280 | XRCC2 | X-ray repair complementing defective repair in Chinese hamster cells 2 | −11.343 |
| 3080283 | XRCC2 | X-ray repair complementing defective repair in Chinese hamster cells 2 | −5.33638 |
| 3312490 | MKI67 | antigen identified by monoclonal antibody Ki-67 | −7.03411 |
| 3203935 | KIF24 | kinesin family member 24 | −2.4674 |
| 3753500 | SLFN11 | schlafen family member 11 | −3.33948 |
| 2545386 | HSP90AA1 | heat shock protein 90 kDa alpha (cytosolic), class A member 1 | −2.34917 |
| 3756193 | TOP2A | topoisomerase (DNA) II alpha 170 kDa | −6.63929 |
| 3318009 | RRM1 | ribonucleotide reductase M1 | −3.24798 |
| 3759452 | KIF18B | kinesin family member 18B | −6.35487 |
| 3980560 | KIF4A | kinesin family member 4A | −4.37826 |
| 3651458 | ACSM4 | acyl-CoA synthetase medium-chain family member 4 | −2.27387 |
| 2334098 | KIF2C | kinesin family member 2C | −6.03185 |
| 3653072 | PLK1 | polo-like kinase 1 (Drosophila) | −3.15382 |
| 2334646 | RAD54L | RAD54-like (S. cerevisiae) | −3.34033 |
| 3433747 | RFC5 | replication factor C (activator 1) 5, 36.5 kDa | −2.27939 |
| 3875195 | MCM8 | minichromosome maintenance complex component 8 | −2.92352 |
| 3655628 | KIF22 | kinesin family member 22 | −2.64981 |
| 3765580 | BRIP1 | BRCA1 interacting protein C-terminal helicase 1 | −4.22345 |
| 3097152 | MCM4 | minichromosome maintenance complex component 4 | −6.42724 |
| 2450345 | KIF14 | kinesin family member 14 | −8.90342 |
| 2780172 | CENPE | centromere protein E, 312 kDa | −5.33076 |
| 3881443 | TPX2 | TPX2, microtubule-associated, homolog (Xenopus laevis) | −3.15849 |
| 2902725 | HSPA1B | heat shock 70 kDa protein 1B | −2.53041 |
| 3772158 | TK1 | thymidine kinase 1, soluble | −2.35939 |
| 2903647 | KIFC1 | kinesin family member C1 | −9.00909 |
| 2454444 | NEK2 | NIMA (never in mitosis gene a)-related kinase 2 | −3.24327 |
| 3443679 | DDX12 | DEAD/H (Asp-Glu-Ala-Asp/His) box polypeptide 12 (CHL1-like helicase homolog, S. cerevisiae) | −2.60108 |
| 3887049 | UBE2C | ubiquitin-conjugating enzyme E2C | −4.8011 |
| 2570616 | BUB1 | budding uninhibited by benzimidazoles 1 homolog (yeast) | −4.79734 |
| 2914777 | TTK | TTK protein kinase | −6.05127 |
| 3347340 | RECQL | RecQ protein-like (DNA helicase Q1-like) | −3.20889 |
| 2577896 | MCM6 | minichromosome maintenance complex component 6 | −3.7336 |
| 3677315 | PKMYT1 | protein kinase, membrane associated tyrosine/threonine 1 | −2.824 |
| 2798915 | TRIP13 | thyroid hormone receptor interactor 13 | −3.42985 |
| 3240012 | MASTL | microtubule associated serine/threonine kinase-like | −2.30082 |

TABLE 6-continued

Genes associated with molecular functions that were up-regulated by more than 2-fold at 24 hours.

| Transcript ID | Gene Symbol | UniqueGene Title | Linear Fold Change |
|---|---|---|---|
| 3129149 | PBK | PDZ binding kinase | −4.50221 |
| 4009238 | SMC1A | structural maintenance of chromosomes 1A | −2.89684 |
| 2691575 | POLQ | polymerase (DNA directed), theta | −2.45356 |
| 3910785 | AURKA | aurora kinase A | −4.32807 |
| 4012142 | ERCC6L | excision repair cross-complementing rodent repair deficiency, complementation group 6-like | −2.79201 |
| 3354799 | CHEK1 | CHK1 checkpoint homolog (S. pombe) | −2.47119 |
| 2366581 | SCYL3 | SCY1-like 3 (S. cerevisiae) | −2.28261 |
| 3248289 | CDC2 | cell division cycle 2, G1 to S and G2 to M | −4.36348 |
| 3474104 | CIT | citron (rho-interacting, serine/threonine kinase 21) | −3.28705 |
| 3706753 | GSG2 | germ cell associated 2 (haspin) | −3.16754 |
| 3257338 | KIF20B | kinesin family member 20B | −4.90034 |
| 3367338 | KIF18A | kinesin family member 18A | −5.26888 |
| 3258168 | KIF11 | kinesin family member 11 | −6.77037 |
| 3258910 | HELLS | helicase, lymphoid-specific | −4.93465 |
| 2830638 | KIF20A | kinesin family member 20A | −3.73204 |
| 3590086 | RAD51 | RAD51 homolog (RecA homolog, E. coli) (S. cerevisiae) | −5.55326 |
| 3589697 | BUB1B | budding uninhibited by benzimidazoles 1 homolog beta (yeast) | −6.07233 |
| 3151534 | ATAD2 | ATPase family, AAA domain containing 2 | −5.09821 |
| 2724585 | N4BP2 | NEDD4 binding protein 2 | −2.02011 |
| 3485074 | RFC3 | replication factor C (activator 1) 3, 38 kDa | −2.61579 |
| 3935862 | CHEK2 | CHK2 checkpoint homolog (S. pombe) | −2.02195 |
| 2836918 | KIF4B | kinesin family member 4B | −2.71247 |
| 3716893 | ATAD5 | ATPase family, AAA domain containing 5 | −4.47478 |
| 3608298 | BLM | Bloom syndrome, RecQ helicase-like | −5.26511 |
| 3158767 | RECQL4 | RecQ protein-like 4 | −2.22859 |
| 2620256 | KIF15 | kinesin family member 15 | −5.2599 |
| 3050367 | FIGNL1 | fidgetin-like 1 | −2.82586 |
| 3599811 | KIF23 | kinesin family member 23 | −2.6147 |
| 3720896 | CDC6 | cell division cycle 6 homolog (S. cerevisiae) | −6.58374 |
| 3944147 | MCM5 | minichromosome maintenance complex component 5 | −3.19318 |
| 3056414 | RFC2 | replication factor C (activator 1) 2, 40 kDa | −2.64783 |
| 2957126 | MCM3 | minichromosome maintenance complex component 3 | −3.55781 |
| 3507960 | KATNAL1 | katanin p60 subunit A-like 1 | −2.08949 |
| 3168508 | MELK | maternal embryonic leucine zipper kinase | −5.17378 |
| 2412799 | ORC1L | origin recognition complex, subunit 1-like (yeast) | −4.93645 |
| 2742985 | PLK4 | polo-like kinase 4 (Drosophila) | −4.84879 |
| 3063685 | MCM7 | minichromosome maintenance complex component 7 | −3.27131 |
| 3404126 | DDX12 | DEAD/H (Asp-Glu-Ala-Asp/His) box polypeptide 12 (CHL1-ike helicase homolog, S. cerevisiae) | −2.53799 |
| 3410060 | DDX11 | DEAD/H (Asp-Glu-Ala-Asp/His) box polypeptide 11 (CHL1-ike helicase homolog, S. cerevisiae) | −3.35521 |
| 2640855 | MCM2 | minichromosome maintenance complex component 2 | −3.44801 |
| 3182781 | SMC2 | structural maintenance of chromosomes 2 | −3.31471 |
| 3744263 | AURKB | aurora kinase B | −3.37031 |

TABLE 6-continued

Genes associated with molecular functions that were up-regulated by more than 2-fold at 24 hours.

| Transcript ID | Gene Symbol | UniqueGene Title | Linear Fold Change |
|---|---|---|---|
| Histone binding (n = 5 of 52 p = 3.46e−3) | | | |
| 3920003 | CHAF1B | chromatin assembly factor 1, subunit B (p60) | −2.83967 |
| 2604254 | HJURP | Holliday junction recognition protein | −5.26841 |
| 3045390 | NCAPD2 | non-SMC condensin I complex, subunit D2 | −3.31611 |
| 3402571 | NCAPD2 | non-SMC condensin I complex, subunit D2 | −2.24347 |
| 3394183 | H2AFX | H2A histone family, member X | −2.55817 |
| 3852565 | ASF1B | ASF1 anti-silencing function 1 homolog B (*S. cerevisiae*) | −2.66808 |
| Chromo shadow domain binding (n = 2 of 6 p = 5.48e−3) | | | |
| 2458289 | LBR | lamin B receptor | −2.55249 |
| 3817501 | CHAF1A | chromatin assembly factor 1, subunit A (p150) | −2.92758 |

The results indicated that inhibition of p300/CBP HAT corresponds with downregulation of genes associated with DNA damage (FIG. 17).

Figure 18A:
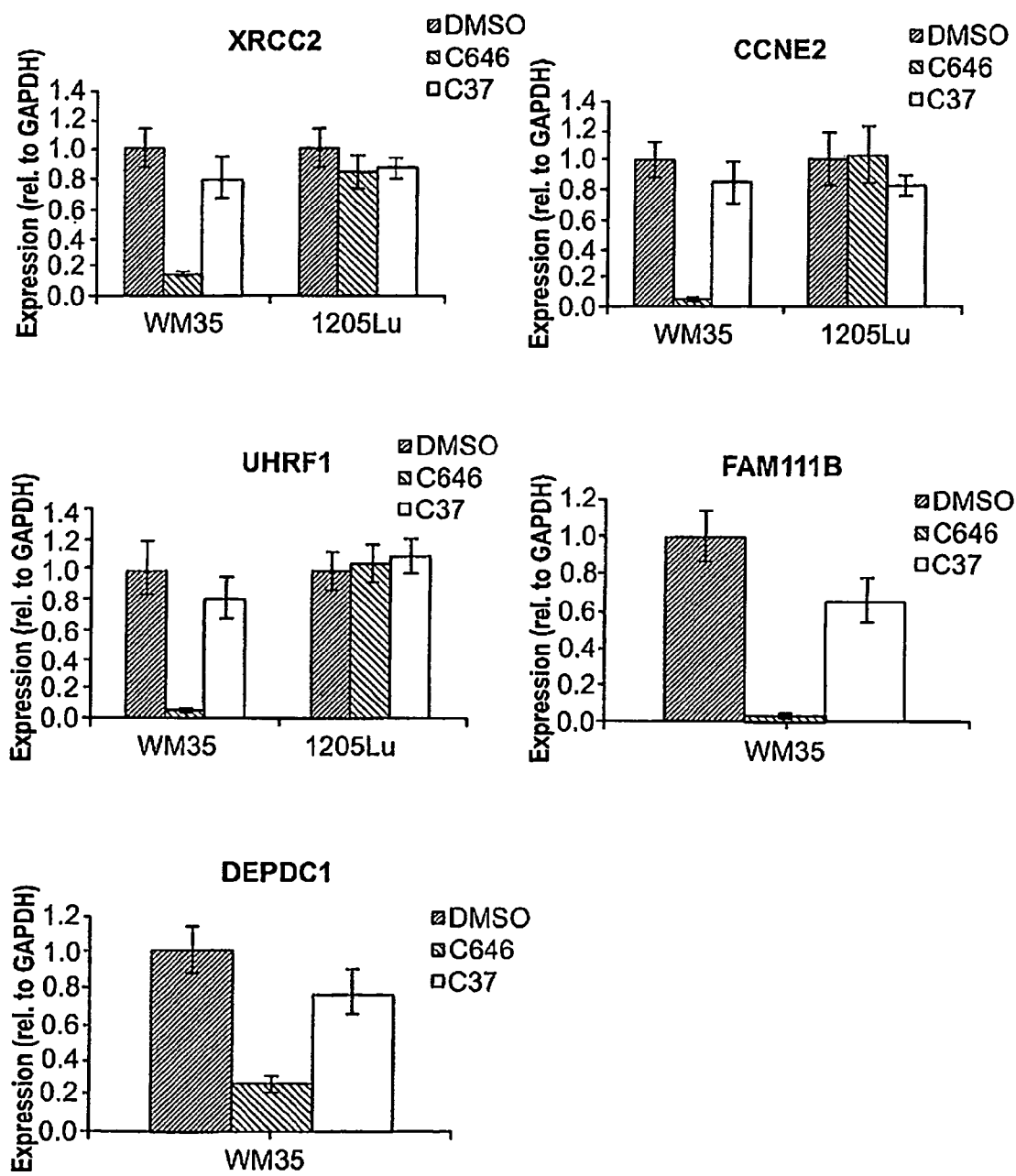
Figure 18B:
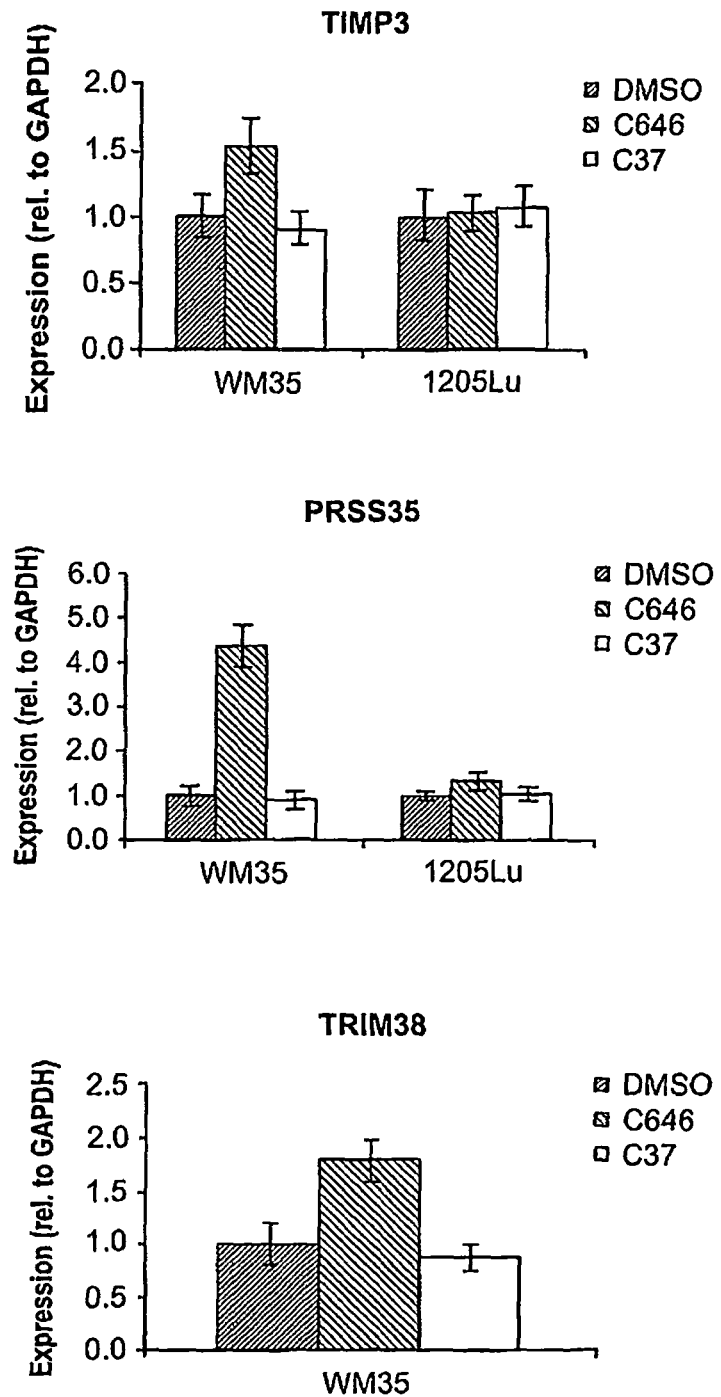

To confirm the microarray results and to further verify that the identified genes are markers of p300/CBP HAT inhibition, WM35 and 1205Lu melanoma cells were treated with 20 µM C646 for 24 hours and expression of several target genes was evaluated by quantitative PCR (FIG. 18). In the WM35 cells, the target genes showed the same pattern of expression (i.e., upregulation/downregulation) as seen in the microarray experiments (FIG. 18C).

Example 15

Cyclin A Modulation by p300 in Tumor Cells

Figure 19A:
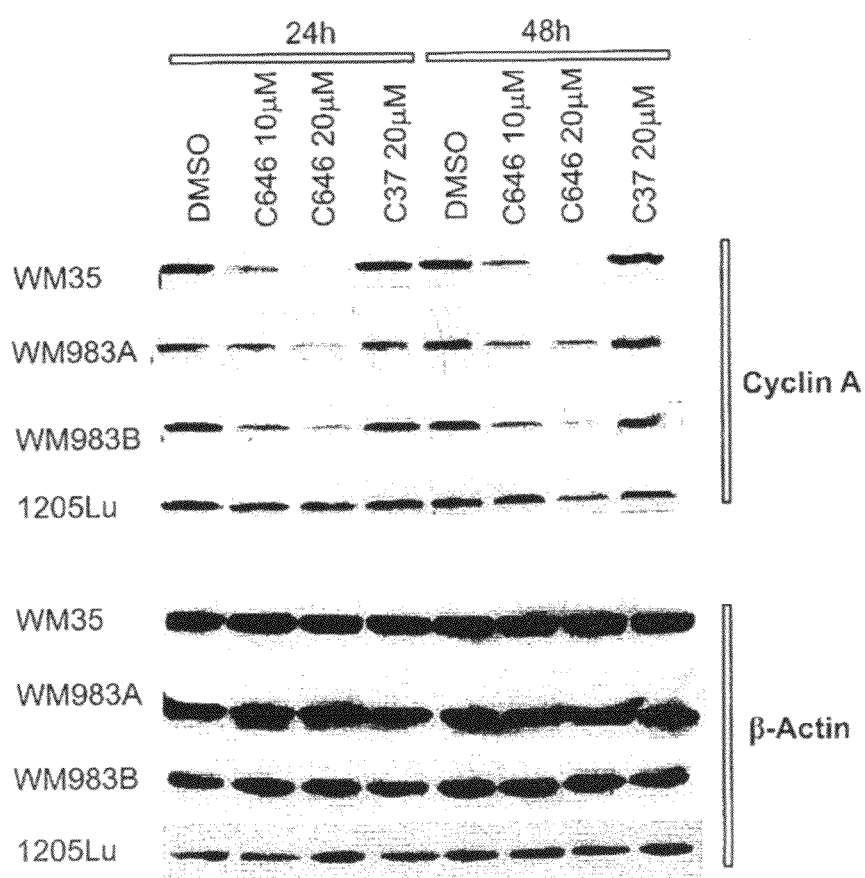

Cyclin A is involved in two cell cycle checkpoints. Cyclin A associates with cdk2 to promote S phase progression, and then it associates with cdc2 during the G2 phase. As shown above, cyclin A is one of genes that is downregulated by greater than 2-fold in tumor cells treated with C646. To confirm that cyclin A is a marker of p300/CBP HAT inhibition, cyclin A protein expression was evaluated in melanoma cells treated with C646 by Western blot. The results indicate that cyclin A protein level decreases after C646 treatment in a dose-dependent fashion, indicating that cyclin A protein expression correlates with p300/CBP HAT inhibition (FIG. 19A). These results were also confirmed by RT PCR (FIG. 19B).

Figure 20B:
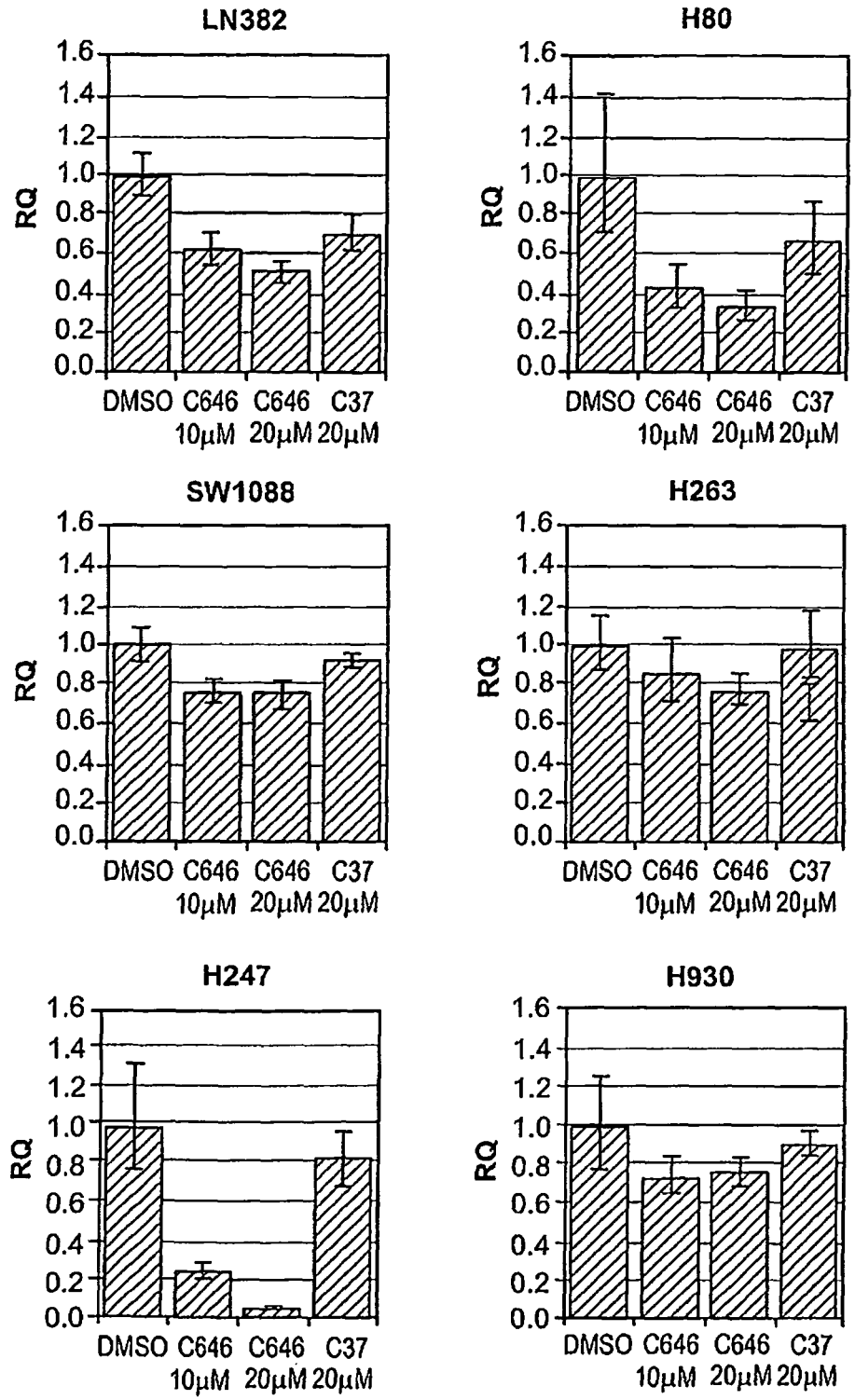

To determine if cyclin A is a biomarker of p300/CBP HAT inhibition in other tumor cells from other types of cancers, cyclin A expression was evaluated in C646 treated glioblastoma cells. The Western blot (FIG. 20A) and RTPCR (FIG. 20B) results for the treated glioblastoma cells were consistent with the melanoma cell data. As such, cyclin A is a biomarker for p300/CBP HAT inhibition across a broad spectrum of cells.

As reported herein, p300/CBP HAT is a therapeutic target for treating cancer. It has been discovered that inhibiting the activity of p300/CBP HAT results in significant inhibition of tumor cell growth, and the results reported herein demonstrate that C646 is a pharmacologically important p300/CBP HAT inhibitor. Furthermore, the data indicates that p300/CBP HAT inhibitors will be effective anti-cancer agents in combination therapies.

Another significant finding was the identification of the downstream effectors of p300/CBP HAT. One of the most important issues facing cancer biologists and medical oncologists today is identifying the factors associated with cancer development and progression. Knowledge about biomarkers associated with disease and disease progression allows for the design of rational, targeted cancer therapies. The identified downstream effectors, including cyclin A, are valuable surrogate markers for p300/CBP HAT activity. These markers are useful in evaluating the effectiveness of anti-cancer therapies that targets p300/CBP HAT activity. In addition, effective combination therapies can be designed using knowledge about these biomarkers.

The results reported herein were obtained using the following methods and materials.

Molecular Modeling

The crystal structure of p300 HAT in complex with bisubstrate analog Lys-CoA (pdb: 3BIY) was prepared for virtual screening using the Internal Coordinate Mechanics (ICM-Pro) software version 3.5 (MolSoft LLC, San Diego Calif.). The ligand and heteroatom molecules were removed from the structure and a continuous dielectric was used in place of the water molecules. Missing hydrogen and heavy atoms were added and atom types and partial charges were assigned. The protein model was adjusted so that the optimal positions of polar hydrogens were identified, the most isomeric form of each histidine was assigned and the correct orientation of the side-chains of glutamine and asparagine were found. Steric clashes were removed by an energy minimization procedure.

Virtual Screening

Virtual screening was undertaken with the ICM-VLS software version 3.5 (MolSoft LLC, San Diego Calif.) using dockScan version 4.4. This method uses an extension of the Empirical Conformational Energy Program for Peptides 3 (ECEPP/3) force field parameters for proteins and the Merck Molecular Force Field (MMFF) for small molecules. Five continuously differentiable potential grid maps were calculated for the receptor using spline interpolation for efficient gradient minimization. These maps include energy terms for electrostatics, directional hydrogen bond, hydrophobic interactions, and two for Van der Waals interactions for steric repulsion and dispersion attraction including a soft potential to limit the effect of minor steric clashes. A collection of 492,793 compounds from the ChemBridge small molecule database (ChemBridge Corp, San Diego Calif.) was screened to the p300 HAT bisubstrate inhibitor binding site. Each ligand was docked into the binding pocket three times. During docking the ligand is flexible and its position and internal torsions are sampled using the ICM biased probability Monte Carlo procedure which includes a local minimization after each random move. Each docked ligand was assigned a score according to the weighted components of the ICM-VLS scoring function.

Peptide Synthesis

Synthetic peptides (H4-15, p300 peptides, Lys-CoA-Tat, Ac-DDDD-Tat) were prepared using automated solid phase peptide synthesis and the Fmoc strategy as described previously (Thompson et al., *J. Biol. Chem.* 276, 33721 (2001); Meng et al., *J. Am. Chem. Soc.* 127, 17182 (2005); Guidez et al., *Mol. Cell. Biol.* 25, 5552 (2005); Liu et al., *Nature* 456, 269 (2008); and Liu et al., *Nature* 451, 846 (2008)). Peptides were purified using reversed phase HPLC and their structures confirmed by mass spectrometry.

Purification of Semisynthetic p300 HAT Domain

A variant of the HAT domain of p300 (residues 1287 to 1652) was expressed as a fusion with the VMA intein chitin binding domain as described previously (Thompson et al., *Nat. Struct. Mol. Biol.* 11, 308 (2004). Residues 1529-1560, comprising the regulatory autoacetylation loop, were deleted in the construct, rendering the enzyme constitutively active. The construct also contained an M1652G mutation. *E. coli* BL21(RIL)-DE3 cells containing the construct were grown to OD 600 of 0.6 at 37° C. The incubator was cooled to 16° C., and expression was induced by addition of 500 µM IPTG. Following overnight expression, the cells were centrifuged and resuspended in lysis buffer prior to lysis via three passes through a French pressure cell. Lysates were clarified through centrifugation and incubated with chitin resin for 30 min at 4° C. The resin was washed thoroughly before addition of 200 mM MESNA and a C-terminal peptide corresponding to residues 1653-1666 of p300. The expressed protein ligation reaction was allowed to proceed for 16 h followed by purification over a MonoS 5/50 GL strong cation exchange column (GE Healthcare) using linear gradients of NaCl (50 to 1000 mM). Purified semisynthetic p300 was concentrated and dialyzed against 20 mM HEPES, pH 7.9, 50 mM NaCl, 1 mM DTT, and 10% glycerol (v/v) prior to flash-freezing in liquid N2 and storage at −80° C. Protein concentration was determined by gel and by Bradford assay using BSA as a standard.

Initial Screen of VLS Hits

The top 194 p300 HAT inhibitor candidates identified by VLS were screened using a coupled spectrophotometric assay. In this assay, CoASH produced by the p300 reaction is used by α-ketoglutarate dehydrogenase (α-KGDH) to produce NADH, which can be monitored spectrophotometrically at 340 nm. Reactions were performed at 30° C. in 1 M HEPES, pH 7.9, and contained 200 µM H4-15, 200 µM TPP, 5 mM MgCl2, 1 mM DTT, 50 µg/mL BSA, 200 µM NAD, 2.4 mM α-ketoglutarate, 200 µM acetyl-CoA, 0.1 units α-KGDH, and 100 nM p300. DMSO was kept at a constant 3.3%, and candidate compounds were screened at 100 µM. Reaction mixtures were incubated at 30° C. for 10 min prior to initiation. Reactions were initiated with addition of H4-15 and followed over the linear portion of the progress curve, which provides the initial velocity via linear regression. Percent inhibition was determined by comparison with velocity without candidate added. Compounds that exhibited over 40% inhibition were subjected to further screening steps. To ensure that compounds were not inhibiting α-KGDH instead of p300, compounds were assayed with 0.2 units of α-KGDH, two times the amount used in the initial screen. To ensure that compounds were not inhibiting through nonspecific aggregation, compounds were assayed in the presence of 0.01% Triton X-100. Compounds whose inhibition was greatly decreased either by raising the α-KGDH concentration or by preventing nonspecific aggregation were removed from further consideration.

Compounds that passed the iterative verification process in the initial screen were then tested in a direct radioactive assay. In this assay, production of $^{14}$C-labeled Ac-H4-15 is monitored electrophoretically. Reactions were performed in 20 mM HEPES, pH 7.9, and contained 5 mM DTT, 80 µM EDTA, 40 µg/mL BSA, 100 µM H4-15, and 5 nM p300. DMSO was kept constant at 2.5%, and inhibitors were screened at 25 µM. Reactions were incubated at 30° C. for 10 minutes, initiated with addition of a 1:1 mixture of 12 C-acetyl-CoA and 14 C-acetyl-CoA to a final concentration of 20 µM, and allowed to run for 10 min at 30° C. Reactions are then quenched with addition of 14% SDS (w/v). Turnover was kept below 10%. All compounds were screened in duplicate. Samples were then loaded onto a 16% Tris-Tricine gel along with a BSA standard and run at 140 V for 90 minutes. Gels were washed and dried, and exposed in a PhosphorImager cassette for ~2 days. Bands corresponding to Ac-H4-15 were then quantified using ImageQuant. Compounds exhibiting over 40% inhibition compared to control were then kinetically characterized.

Kinetic Characterization of Verified Inhibitors and Analogs $IC_{50}$ values for the putative p300 HAT inhibitors identified through the initial screen were determined using the direct radioactive assay described above. Reactions were performed in 20 mM HEPES, pH 7.9, and contained 5 mM DTT, 80 µM EDTA, 40 µg/mL BSA, 100 µM 114-15, and 5 nM p300. Putative inhibitors were added over a range of concentrations, with DMSO concentration kept constant (<5%). Reactions were incubated at 30° C. for 10 minutes, then initiated with addition of a 1:1 mixture of $^{12}$C-acetyl-CoA and $^{14}$C-acetyl-CoA to 20 µM. After 10 mM at 30° C., reactions were quenched with 14% SDS (w/v). All concentrations were screened in duplicate. Gels were run, washed, dried, and exposed to a PhosphorImager plate as described above, and production of Ac-H4-15 quantified. Data were fit to the following equation to obtain $IC_{50}$s.

Patterns of inhibition of putative p300 HAT inhibitors were determined in a similar fashion. One substrate was held constant while the other was varied over a range of three inhibitor concentrations (0, 0.5×$IC_{50}$, and $IC_{50}$). AcCoA was varied from 5-120 µM while holding H4-15 constant at 100 µM, and H4-15 was varied from 25-500 µM while holding acetyl-CoA constant at 10 µM. Reactions were performed in duplicate as described above; enzyme concentration and reaction time were varied to keep turnover below 10%. Following quantification, data were globally fit to equations for competitive or noncompetitive inhibition to determine the optimal pattern of inhibition.

Determining Inhibitor Specificity for p300 HAT

C646, C375, and C146 were screened spectrophotometrically against PCAF (p300/CBP-associated factor, a histone acetyltransferase) and AANAT (arylalkylamine N-acetyltransferase, a non-histone acetyltransferase) using a similar coupled assay as described above. PCAF reactions were performed in 100 mM HEPES, pH 7.9, and contained 200 µM TPP, 5 mM MgCl$_2$, 1 mM DTT, 50 mM NaCl, 0.05 mg/mL BSA, 200 µM NAD, 2.4 mM α-KG, 30 µM acetyl-CoA, 0.037 units α-KGDH, 3.3% DMSO, and 10 µM inhibitor. Reactions took place at 30° C. Reactions were initiated by addition of 10 nM PCAF and were followed at 340 nm over the linear portion of the curve below 10% turnover. AANAT reactions were performed in 100 mM NH$_4$ OAc, pH 6.8, and contained 200 µM TPP, 5 mM MgCl$_2$, 1 mM DTT, 50 mM NaCl, 0.05 mg/mL BSA, 200 µM NAD, 2.4 mM α-KG, 200 µM AcCoA, 0.1 units α-KGDH, 3.3% DMSO, and 10 µM inhibitor. Reactions took place at 25° C. Reactions were initiated with addition of 65 nM AANAT, and followed at 340 nm, as above. Percent inhibition values were compared to those with p300, which were repeated using the protocol given above. C646 was further analyzed as a potential HAT inhibitor with yeast GCN5, the Sas2/4/5 complex, MOZ, and Rtt109. Yeast GCN5, MOZ, and the Rtt109/Vps75 complex were purified as described elsewhere (Poux et al., *Proc. Natl. Acad. Sci. USA* 99, 14065 (2002); Tang et al., *Nat. Struct. Mol. Biol.* 15, 738 (2008); and Holbert et al., *J. Biol. Chem.* 282, 36603 (2007). The SAS complex was expressed and purified in *E. coli.* as detailed elsewhere (Shia et al., *J. Biol. Chem.* 280, 11987 (2005) and Sutton et al., *J. Biol. Chem.* 278, 16887 (2003). Briefly, the SAS2, SAS4 and SAS5 proteins were co-expressed using the Duet system (Novagen) in BL21-CodonPlus(DE3)-RIL cells (Strategene). The complex was purified using a combination of nickel affinity, ion exchange (HisTrap SP) and gel filtration (Superdex 200) chromatography.

HAT assays with yeast GCN5, SAS complex, MOZ, and Rtt109/Vps75 complex used the direct radioactive assay described above. Reactions were carried out at 30° C. for times varying from 2 to 4 min under the following reaction conditions: 50 mM Hepes, pH 7.9, 50 mM NaCl, 0.05 mg/ml BSA, 5 mM DTT, 0.05 mM EDTA, 0.25% DMSO, 10 µM of *X. laevis* histone H3, and varying concentrations of C646 (0, 3, 10 µM). The reactions contained either 70 nanograms of Rtt109/Vps75, 15 nanograms of yGcn5, 300 nanograms of the SAS complex or 1 microgram of hMOZ. The amount of enzyme used in each assay was estimated by comparing Coomassie Blue staining of samples with bovine serum albumin standards, analyzed by SDS-PAGE. The mixture was allowed to equilibrate at 30° C. for 10 min before the reaction was initialed with addition of a 1:1 mixture of $^{12}$C-AcCoA and $^{14}$C-AcCoA to a final concentration of 20 µM. After the appropriate time the reaction was quenched with 6x Tris-Tricine gel loading buffer which contained: 0.2 M Tris-Cl pH 6.8, 40% v/v glycerol, 14% w/v SDS, 0.3M DTT, and 0.06% w/v Coomassie Blue. The $^{14}$C-labeled histone substrates were separated from reactants by running the reaction out on a 16.5% Tris-Tricine SDS-PAGE gel. The rate of $^{14}$C-incorporation into histone H3 was quantified by autoradiography. We performed all assays in duplicate, and these generally agreed within 20%.

Time Course Studies

Time courses of p300 HAT with C646 were determined using the radioactive assay described above. Reactions were performed using the conditions detailed above with 1.5 µM C646. Reactions were quenched at particular time intervals, then run on a 16% Tris-Tricine gel and quantified as described above. Similar studies were performed varying the time of p300 HAT pre-incubation with C646. Assays contained the conditions detailed above, with 1.5 µM C646 added at various times prior to initiation with 10 µM acetyl-CoA. Reactions were quenched after 5 min, then run on a 16% Tris-Tricine gel and quantified as described above. All time points were screened in duplicate.

Inhibition with p300 Mutants

Sites for mutation were chosen by examination of the C646 binding model generated during VLS. T1411A, W1466F, Y1467F, and R1410A mutations were installed using QuikChange protocols. p300 variants were expressed in *E. coli* BL21(RIL)-DE3 cells and purified using expressed protein ligation as described above. IC$_{50}$ values for C646 with all mutants were obtained using the methods described above. All assays contained 10 µM of a 1:1 mixture of $^{12}$C-acetyl-CoA and $^{14}$C-acetyl-CoA and 400 µM H4-15. Reaction time was varied between 5 and 10 min to keep turnover below 10%. Enzyme concentrations were altered for each mutant, as active site mutations affected enzyme activity. In a similar fashion, kinetic parameters for each mutant vs. AcCoA were determined. [H4-15] was 400 µM, and DMSO was held constant at 2.5%. Reactions proceeded for 6 minutes before being quenched and run on a 16% Tris-Tricine gel as described above. Data were quantified and fit to the Michaelis-Menten equation.

NMR Studies

The 2D $^1$H-$^1$H correlation spectra were acquired at 30° C. on an 11.7 T Varian INOVA spectrometer using a pentaprobe equipped with z-axis pulse-field gradient coils. Data were processed and analyzed using NMRPipe. The sample contained 600 µL of 10 mM C646 DMSO-d6 solution.

Histone Acetylation Assays in Mouse Cells

C3H 10T1/2 mouse fibroblasts were grown in DMEM with 10% FCS at 37° C. with 5% CO$_2$. Confluent cultures were rendered quiescent in DMEM with 0.5% FCS for 18-20 h prior to treatment. Cells were treated with the following compounds: TSA (10 ng/ml [33 nM]; Sigma), C646 (25 µM), C37 (25 µM). Antibodies were used at the following concentrations: total H3 (1:10000; ab7834; Abcam); H4K12ac (1:2500; 06-761; Upstate). Rabbit anti-H3K9ac (1:10000) antibodies were generated in-house. Histones were isolated from cells by acid extraction, separated by SDS and acid-urea polyacrylamide gel electrophoresis and analyzed by Western blotting.

Cancer Cell Studies

The following cell lines were used: WM35 (melanoma), WM983A (melanoma), 1205Lu (melanoma), H23 (NSCLC), H838 (NSCLC), and H1395 (NSCLC). Melanoma cells were maintained in Dulbecco's Modified Eagle Medium. NSCLCs were maintained in RPMI Medium 1640. Both types of media were supplemented with 10% fetal bovine serum (FBS), penicillin-streptomycin, and L-glutamine. Media, pen-strep, and L-glutamine were purchased from Invitrogen. FBS was purchased from Gemini Bio-Products (#100106). Before treating cells with p300 inhibitors (C646, Lys-CoA-Tat) or control compounds (C37, Ac-Asp-Asp-Asp-Asp-Tat also known as Ac-DDDD-Tat), cells were plated at sub-confluent concentration (~60%) and incubated at 37° C. until attached to the plating surface. Compound stocks (10-20 mM in anhydrous DMSO) were directly added to culture media at desired concentrations. DMSO concentration was kept constant at 0.2% between different treatment conditions. Cells were seeded in 96-well plates at ~5000 cells per well on average, depending on each cell line's doubling time. After attachment, cells were treated with p300 inhibitors, control compounds, or DMSO for 24 h. After treatment, $^3$H-thymidine (1 mCi/ml stock) was added to media at 10 µCi/ml final concentration. Cells were incubated for an additional 5 hours, then trypsinized and collected onto a filter mat using a Cell Harvester (PerkinElmer). Radioactivity was measured with a MicroBeta plate reader (PerkinElmer). Each sample was tested in triplicate.

When inhibition was assessed using the AlamarBlue® assay (Invitrogen, Carlsbad, Calif.), cells were initially seeded at 500 cells per well in a 96-well plate. AlamarBlue® is a non-toxic reagent that measures cellular metabolic activity. Its main ingredient is resazurin, a non-fluorescent indicator dye that is reduced to bright red-fluorescent resorufin in metabolically active cells. AlamarBlue® was added to growth medium at ⅟₁₀ of the total volume (e.g., 20 µl in 200 µl total volume). Cells were treated with C646 ranging from 1 nM to 100 µM. Fluorescence reading was taken from the same plate every day for 5 days to ensure that the saturation point was not reached. Fluorescence intensity is proportional to the number of live cells in the plate.

Cell Cycle Analysis

Cells treated with C646 or DMSO were stained with propidium iodide (PI). Briefly, equal number of cells (greater than 10 6) in 0.5 ml PBS were fixed in 70% ethanol for at least 2 h at 4° C. A stock staining solution containing 10 ml of 0.1% Triton X-100 in PBS, 400 µl of RNase cocktail (equivalent of ~200 units of RNase A) (Ambion), and 200 µl of 1 mg/ml PI was prepared. Fixed cells were spun at 200 g for 5 min (Beckman Coulter Allegra® X-12R, with an SX4750A rotor), re-hydrated in 5 ml PBS, and spun again to remove all traces of ethanol. Cells were stained with 1 ml staining solution for 20 min at 37° C., then immediately analyzed on a FACSCalibur flow cytometer (BD Biosciences) at the Johns Hopkins Flow Cytometry Core Facility. Data acquisition and analysis were performed with the CellQuest software (BD). WinMDI 2.9 (http://facs.scripps.edu.software.html) was also used for data presentation.

NCI-60 DTP Human Tumor Cell Line Screen

The in vitro cancer screen was performed at the National Cancer Institute as described in detail at http://dtp.nci.nih.gov/branches/btb/ivelsp.html. Cells were initially screened with 100 μM C646 for 48 hours (see FIG. 13A). A second screen was then performed using five different concentrations of C646 (see FIGS. 13B and 13C).

Briefly, cells were plated in 96 well plates at a concentration of 5,000-40,000 cells/well. The cells were grown for 24 hours after plating, C646 was added, and the assay was terminated after 48 hours by addition of TCA (10% TCA for adherent cells and 16% TCA for suspension cells). Using the absorbance measurements [time zero, (Tz), control growth, (C), and test growth in the presence of drug at the five concentration levels (Ti)], the percentage growth was calculated at each of the drug concentrations levels. Percentage growth inhibition was calculated as:

$$[(Ti-Tz)/(C-Tz)] \times 100 \text{ for concentrations for which } Ti \geq Tz$$

$$[(Ti-Tz)/Tz] \times 100 \text{ for concentrations for which } Ti < Tz$$

where Tz is time zero, C is control growth, and Ti is test growth in the presence of drug at the five concentration levels.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

INCORPORATION BY REFERENCE

All patents and publications mentioned in this specification are herein incorporated by reference to the same extent as if each independent patent and publication was specifically and individually indicated to be incorporated by reference.

What is claimed is:

1. A method for treating cancer in a subject, the method comprising administering an effective amount of a p300/CBP histone acetyltransferase (HAT) inhibitor selected from the group consisting of a) a compound represented by Formula II:

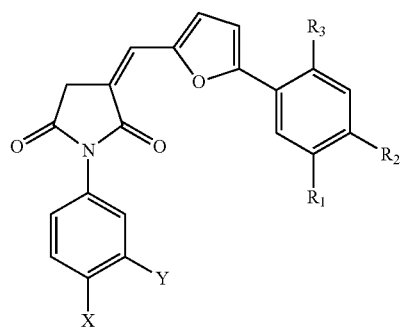

in which
X is H, C(O)-Q or S(O)$_2$-Q;
Y is H, halogen, or C(O)-Q;
R$_1$ and R$_2$ are independently H or C$_1$-C$_4$alkyl; and
R$_3$ is halogen, C(O)-Q, NO$_2$, CN, or CH$_2$OH;
Q is OH, O—C$_1$-C$_4$alkyl, —NH$_2$, or NH(C$_1$-C$_4$alkyl);
or a salt, solvate, or stereoisomer thereof, b) a compound represented by Formula III:

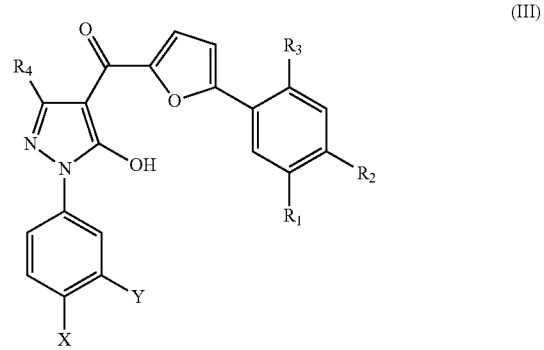

in which
X is H, C(O)-Q or S(O)$_2$-Q;
Y is H, halogen, or C(O)-Q;
R$_1$ and R$_2$ are independently H or C$_1$-C$_4$alkyl; and
R$_3$ is halogen, C(O)-Q, NO$_2$, CN, or CH$_2$OH;
R$_4$ is H or methyl;
Q is OH, O—C$_1$-C$_4$alkyl, —NH$_2$, or NH(C$_1$-C$_4$alkyl);
or a salt, solvate or stereoisomer thereof; and c) a compound selected from the following compounds:

| Compound | Structure |
|---|---|
| 6b | 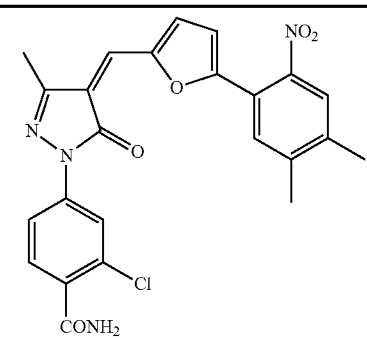 |
| 6g | 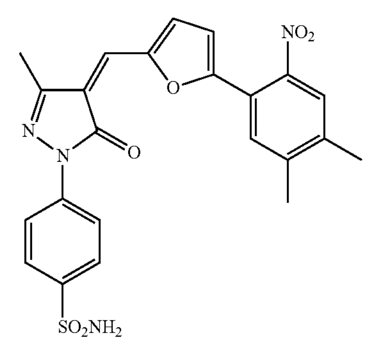 |

-continued

| Compound | Structure |
|---|---|
| 6i | 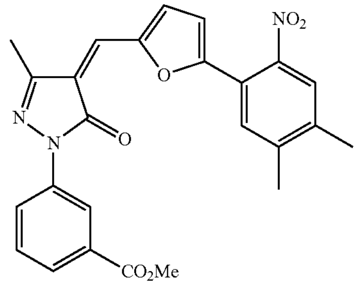 |
| 6j | 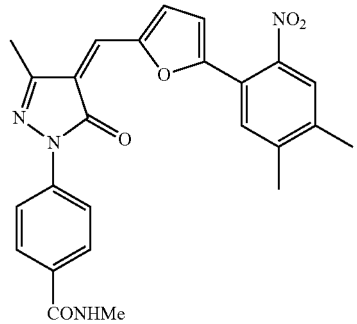 |
| 6l | 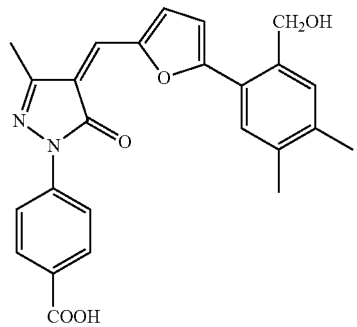 |
| 6m | 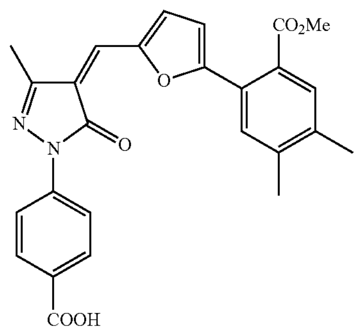 |
| 6n | 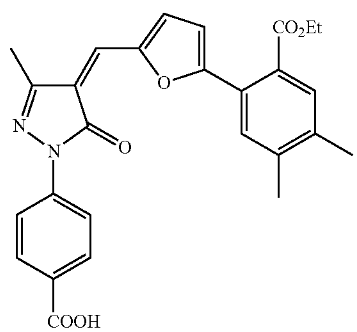 |

-continued

| Compound | Structure |
|---|---|
| 6o | 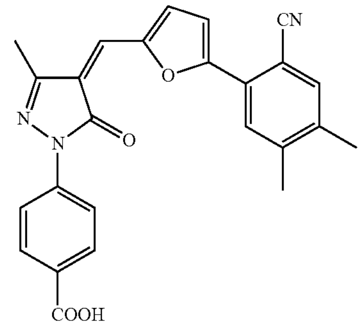 |
| 6q | 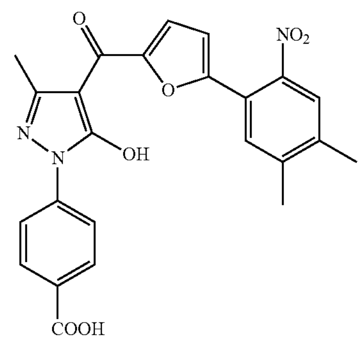 |
| 6r | | or a salt, solvate, or stereoisomer thereof, to a subject in need thereof, wherein the cancer is selected from the group consisting of leukemia, brain cancer, lung cancer, central nervous system (CNS) cancer, melanoma, renal cancer, prostate cancer, colon cancer, ovarian cancer, and breast cancer.

2. The method of claim 1, wherein the p300/CBP HAT inhibitor is a p300-selective inhibitor.

3. The method of claim 1, wherein the method further comprises administering radiation therapy or at least one additional anti-cancer agent.

4. The method of claim 3, wherein the anti-cancer agent is a DNA damaging chemotherapeutic agent.

5. The method of claim 4, wherein the DNA damaging chemotherapeutic agent is cisplatin or temozolamide.

6. A method of inhibiting the growth, proliferation, or survival of a neoplastic cell, the method comprising contacting the cell with an effective amount of a p300/CBP HAT inhibitor selected from the group consisting of a) a compound represented by Formula II:

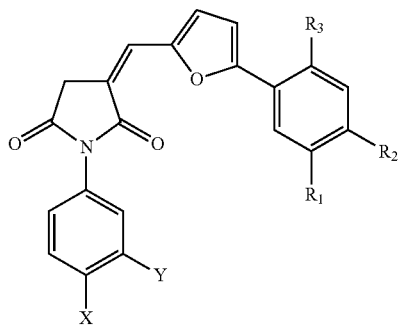

(II)

in which
X is H, C(O)-Q or S(O)$_2$-Q;
Y is H, halogen, or C(O)-Q;
R$_1$ and R$_2$ are independently H or C$_1$-C$_4$alkyl; and
R$_3$ is halogen, C(O)-Q, NO$_2$, CN, or CH$_2$OH;
Q is OH, O—C$_1$-C$_4$alkyl, —NH$_2$, or NH(C$_1$-C$_4$alkyl);
or a salt, solvate, or stereoisomer thereof,
b) a compound represented by Formula III:

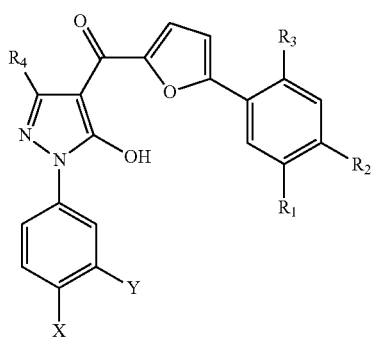

(III)

in which
X is H, C(O)-Q or S(O)$_2$-Q;
Y is H, halogen, or C(O)-Q;
R$_1$ and R$_2$ are independently H or C$_1$-C$_4$alkyl; and
R$_3$ is halogen, C(O)-Q, NO$_2$, CN, or CH$_2$OH;
R$_4$ is H or methyl;
Q is OH, O—C$_1$-C$_4$alkyl, —NH$_2$, or NH(C$_1$-C$_4$alkyl);
or a salt, solvate or stereoisomer thereof; and
c) a compound selected from the following compounds:

| Compound | Structure |
|---|---|
| 6b | (structure with NO$_2$, furan, pyrazolone, phenyl-Cl, CONH$_2$) |
| 6g | (structure with NO$_2$, dimethylphenyl, furan, pyrazolone, phenyl-SO$_2$NH$_2$) |
| 6i | (structure with NO$_2$, dimethylphenyl, furan, pyrazolone, phenyl-CO$_2$Me) |
| 6j | (structure with NO$_2$, dimethylphenyl, furan, pyrazolone, phenyl-CONHMe) |
| 6l | (structure with CH$_2$OH, dimethylphenyl, furan, pyrazolone, phenyl-COOH) |

| Compound | Structure |
|---|---|
| 6m | 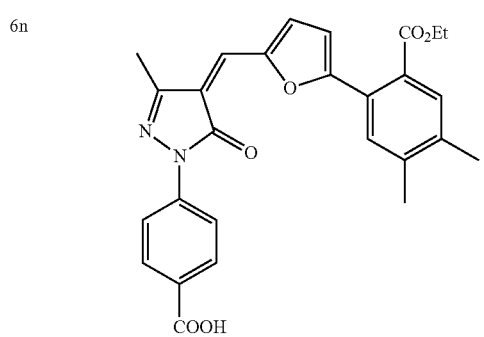 |
| 6n | 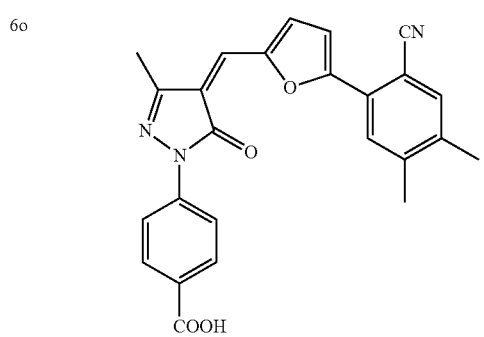 |
| 6o | 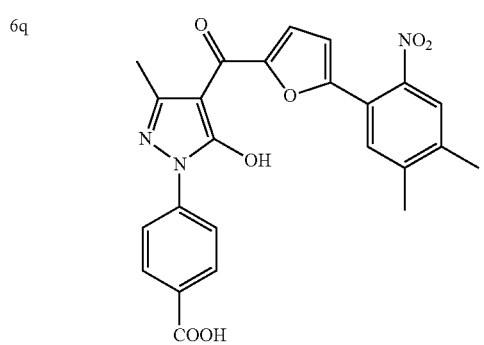 |
| 6q | 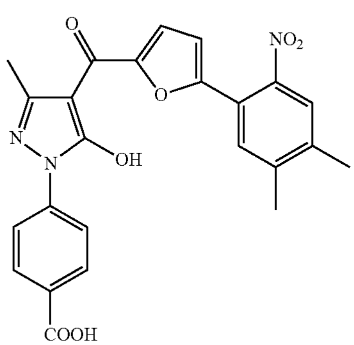 |

| Compound | Structure |
|---|---|
| 6r | 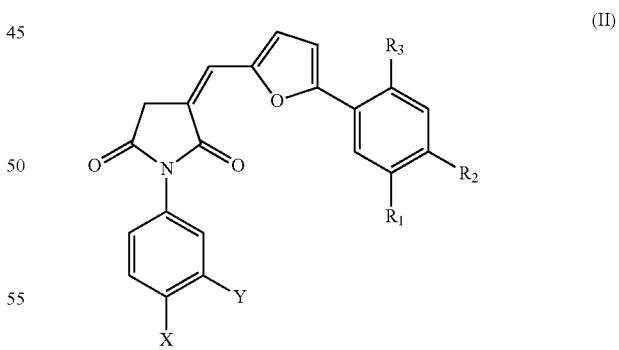 | or a salt, solvate, or stereoisomer thereof, to a subject in need thereof, wherein the neoplastic cell is selected from the group consisting of leukemia cells, brain cancer cells, lung cancer cells, central nervous system (CNS) cancer cells, melanoma cells, renal cancer cells, prostate cancer cells, colon cancer cells, ovarian cancer cells, and breast cancer cells, thereby inhibiting the growth, proliferation or survival of the neoplastic cell.

7. The method of claim 6, wherein the method further comprises exposing the cell to radiation therapy or contacting the cell with at least one additional anti-cancer agent.

8. The method of claim 7, wherein the anti-cancer agent is a DNA damaging chemotherapeutic agent.

9. The method of claim 8, wherein the DNA damaging chemotherapeutic agent is cisplatin or temozolamide.

10. The method of claim 7, wherein the method is carried out in vitro or in vivo.

11. A method of selecting a treatment regimen for a subject diagnosed as having cancer, the method comprising contacting a cancer cell of the subject with an effective amount of a p300/CBP HAT inhibitor selected from the group consisting of a) a compound represented by Formula II:

(II)

in which
X is H, C(O)-Q or S(O)$_2$-Q;
Y is H, halogen, or C(O)-Q;
$R_1$ and $R_2$ are independently H or $C_1$-$C_4$alkyl; and
$R_3$ is halogen, C(O)-Q, NO$_2$, CN, or CH$_2$OH;
Q is OH, O—$C_1$-$C_4$alkyl, —NH$_2$, or NH($C_1$-$C_4$alkyl);
or a salt, solvate, or stereoisomer thereof, b) a compound represented by Formula III:

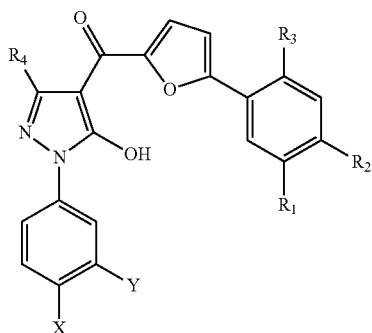

in which
 X is H, C(O)-Q or S(O)$_2$-Q;
 Y is H, halogen, or C(O)-Q;
 $R_1$ and $R_2$ are independently H or $C_1$-$C_4$alkyl; and
 $R_3$ is halogen, C(O)-Q, NO$_2$, CN, or CH$_2$OH;
 $R_4$ is H or methyl;
 Q is OH, O—$C_1$-$C_4$alkyl, —NH$_2$, or NH($C_1$-$C_4$alkyl);
 or a salt, solvate or stereoisomer thereof; and
c) a compound selected from the following compounds:

| Compound | Structure |
|---|---|
| 6b | 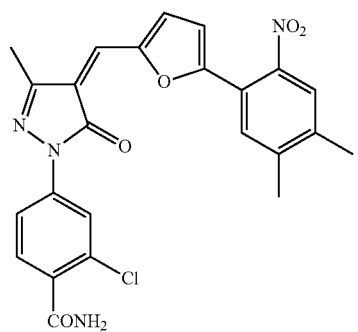 |
| 6g | 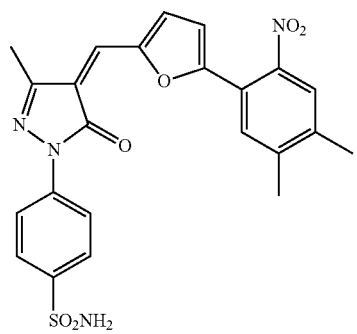 |

-continued

| Compound | Structure |
|---|---|
| 6i | 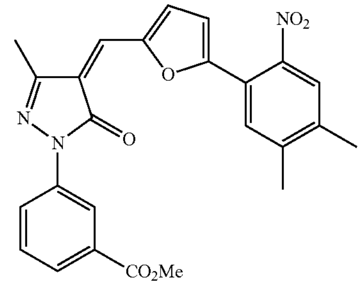 |
| 6j | 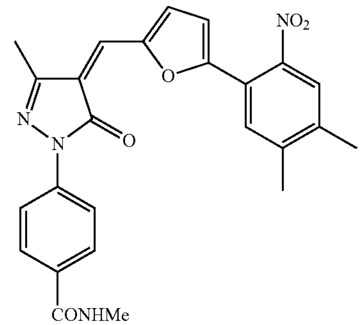 |
| 6l | 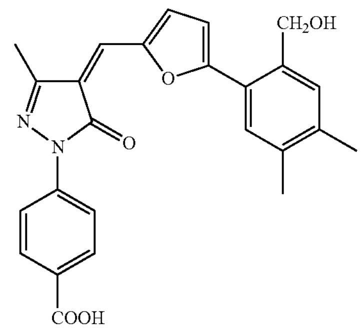 |
| 6m | 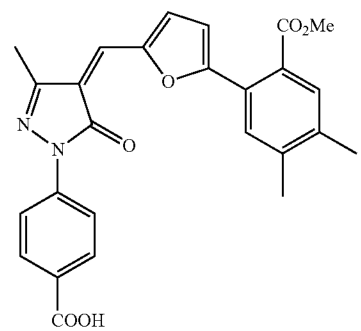 |
| 6n | 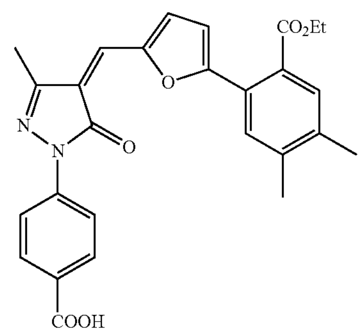 |

| Compound | Structure |
|---|---|
| 6o | 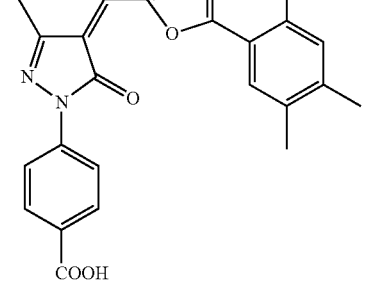 |
| 6q | 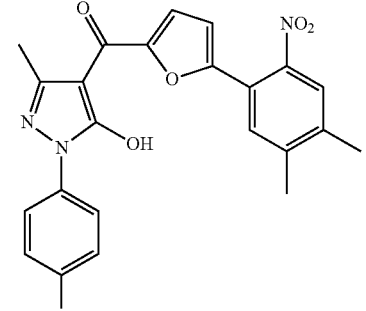 |
| 6r | 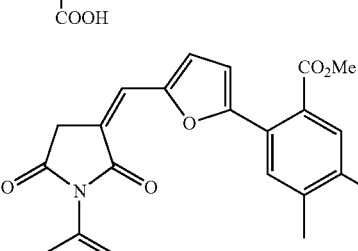 | or a salt, solvate, or stereoisomer thereof, to a subject in need thereof, wherein the cancer is selected from the group consisting of leukemia, brain cancer, lung cancer, central nervous system (CNS) cancer, melanoma, renal cancer, prostate cancer, colon cancer, ovarian cancer, and breast cancer, and detecting an alteration in the expression of one or more biomarkers selected from the group consisting of CENPE, MAD2L1, BUB1, TTK, CENPF, NEK2, FBXO5, CDC25C, BRCA1, CDKN2C, KNTC1, ANLN, FOXM1, TPX2, CDC25A, CCNA2, UBE2C, GMNN, E2F1, DLGAP5, PKMYT1, TIMELESS, SMC1A, CCNB1, CHEK1, TACC3, CCNE2, KIF20B, RFWD3, NUSAP1, BUB1B, BRCA2, C15orf42, BLM, ZWILCH, E2F2, CDC6, GTSE1, PLK4, CKS2, ZWINT, ESPL1, KIF2C, SKA2, SKA1, SKA3, HIST2H2AA3, HIST2H2AB, HIST1H2BM, HIST3H2A, HIST1H2AG, HMGB2, HIST2H2AA3, HIST2H2AC, HJURP, HIST1H2BK, CHAF1A, HIST1H1A, HIST1H2AB, HIST1H2BB, HIST1H1C, HIST1H1D, HIST1H3F, HIST1H2BL, HIST1H2AK, HIST1H1B, H2AFX, MCM2, ASF1B, CHAF1B, HELLS, NDC80, CENPA, KIF18A, CDCA5, CCDC99, TRIAP1, BTG2, FAS, BAX, RPS27L, CITED2, MDM2, CSNK1D, TP53I3, PHLDA3, ACVR1B, DDIT3, TP53INP1, POLA1, TOP2A, SUV39H1, POLE, CENPH, FANCG, ESCO2, FEN1, POLQ, RAD51, NEIL3, HMGB3, HMGB1, RFC5, RFC3, RFC2, MCM4, RECQL, MCM6, RAD51, EXO1, RECQL4, RPA2, RAD51AP1, MCM7, SMC4, XRCC2, MKI67, KIF24, SLFN11, HSP90AA1, RRM1, KIF18B, KIF4A, ACSM4, PLK1, RAD54L, RFC5, MCM8, KIF22, BRIP1, KIF14, HSPA1B, TK1, KIFC1, DDX12, RECQL, MCM6, TRIP13, MASTL, PBK, AURKA, ERCC6L, SCYL3, CDC2, CIT, GSG2, KIF11, KIF20A, RAD51, ATAD2, N4BP2, RFC3, CHEK2, KIF4B, ATAD5, RECQL4, KIF15, FIGNL1, KIF23, MCM5, RFC2, MCM3, KATNAL1, MELK, ORC1L, PLK4, MCM7, DDX12, DDX11, SMC2, AURKB, NCAPD2, NCAPD2, and LBR, in response to the compound, wherein detection of an alteration indicates that the cancer is susceptible to treatment with the compound, and wherein the treatment regimen comprises administering the compound to the subject if the cancer is determined to be susceptible to treatment with the compound.

12. The method of claim 11, wherein the subject was treated with radiation therapy or at least one additional anti-cancer agent.

13. The method of claim 12, wherein the anti-cancer agent is a DNA damaging chemotherapeutic agent.

14. The method of claim 13, wherein the DNA damaging chemotherapeutic agent is cisplatin or temozolamide.

15. A method of monitoring therapeutic efficacy of a p300/CBP HAT inhibitor in a subject diagnosed as having cancer, the method comprising detecting expression of one or more biomarkers selected from the group consisting of CENPE, MAD2L1, BUB1, TTK, CENPF, NEK2, FBXO5, CDC25C, BRCA1, CDKN2C, KNTC1, ANLN, FOXM1, TPX2, CDC25A, CCNA2, UBE2C, GMNN, E2F1, DLGAP5, PKMYT1, TIMELESS, SMC1A, CCNB1, CHEK1, TACC3, CCNE2, KIF20B, RFWD3, NUSAP1, BUB1B, BRCA2, C15orf42, BLM, ZWILCH, E2F2, CDC6, GTSE1, PLK4, CKS2, ZWINT, ESPL1, KIF2C, SKA2, SKA1, SKA3, HIST2H2AA3, HIST2H2AB, HIST1H2BM, HIST3H2A, HIST1H2AG, HMGB2, HIST2H2AA3, HIST2H2AC, HJURP, HIST1H2BK, CHAF1A, HIST1H1A, HIST1H2AB, HIST1H2BB, HIST1H1C, HIST1H1D, HIST1H3F, HIST1H2BL, HIST1H2AK, HIST1H1B, H2AFX, MCM2, ASF1B, CHAF1B, HELLS, NDC80, CENPA, KIF18A, CDCA5, CCDC99, TRIAP1, BTG2, FAS, BAX, RPS27L, CITED2, MDM2, CSNK1D, TP53I3, PHLDA3, ACVR1B, DDIT3, TP53INP1, POLA1, TOP2A, SUV39H1, POLE, CENPH, FANCG, ESCO2, FEN1, POLQ, RAD51, NEIL3, HMGB3, HMGB1, RFC5, RFC3, RFC2, MCM4, RECQL, MCM6, RAD51, EXO1, RECQL4, RPA2, RAD51AP1, MCM7, SMC4, XRCC2, MKI67, KIF24, SLFN11, HSP90AA1, RRM1, KIF18B, KIF4A, ACSM4, PLK1, RAD54L, RFC5, MCM8, KIF22, BRIP1, KIF14, HSPA1B, TK1, KIFC1, DDX12, RECQL, MCM6, TRIP13, MASTL, PBK, AURKA, ERCC6L, SCYL3, CDC2, CIT, GSG2, KIF11, KIF20A, RAD51, ATAD2, N4BP2, RFC3, CHEK2, KIF4B, ATAD5, RECQL4, KIF15, FIGNL1, KIF23, MCM5, RFC2, MCM3, KATNAL1, MELK, ORC1L, PLK4, MCM7, DDX12, DDX11, SMC2, AURKB, NCAPD2, NCAPD2, and LBR, in a cancer cell of the subject before and after administration of the p300/CBP HAT inhibitor, wherein the cancer cell is selected from the group consisting of leukemia cells, brain cancer cells, lung cancer cells, central nervous system (CNS) cancer cells, melanoma cells, renal cancer cells, prostate cancer cells, colon cancer cells, ovarian cancer cells, and breast cancer cells, and comparing the expression of the biomarker before and after treatment, wherein detection of an alteration in expression indicates the therapeutic efficacy of the inhibitor.

16. The method of claim 15, wherein the p300/CBP HAT inhibitor is a p300-selective inhibitor.

17. The method of claim 15, wherein the p300/CBP HAT inhibitor is selected from the group consisting of a) a compound represented by Formula II:

(II)

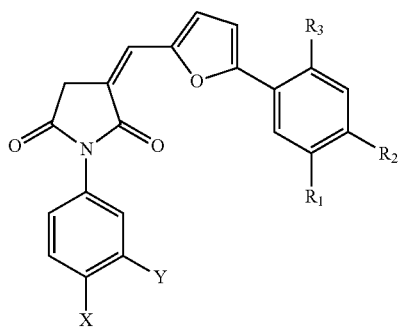

in which
X is H, C(O)-Q or S(O)₂-Q;
  Y is H, halogen, or C(O)-Q;
  $R_1$ and $R_2$ are independently H or $C_1$-$C_4$alkyl; and
  $R_3$ is halogen, C(O)-Q, $NO_2$, CN, or $CH_2OH$;
  Q is OH, O—$C_1$-$C_4$alkyl, —$NH_2$, or NH($C_1$-$C_4$alkyl);
  or a salt, solvate, or stereoisomer thereof,
b) a compound represented by Formula III:

(III)

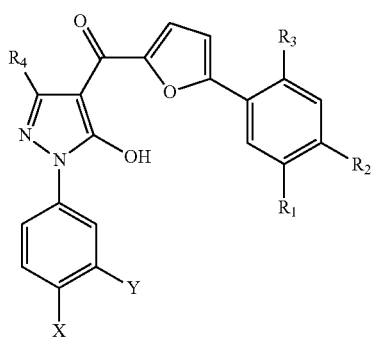

in which
  X is H, C(O)-Q or S(O)₂-Q;
  Y is H, halogen, or C(O)-Q;
  $R_1$ and $R_2$ are independently H or $C_1$-$C_4$alkyl; and
  $R_3$ is halogen, C(O)-Q, $NO_2$, CN, or $CH_2OH$;
  $R_4$ is H or methyl;
  Q is OH, O—$C_1$-$C_4$alkyl, —$NH_2$, or NH($C_1$-$C_4$alkyl);
  or a salt, solvate or stereoisomer thereof; and
c) a compound selected from the following compounds:

| Compound | Structure |
|---|---|
| 6b | 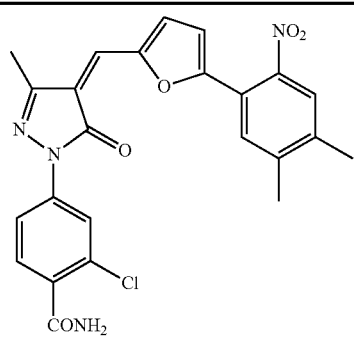 |
| 6g | 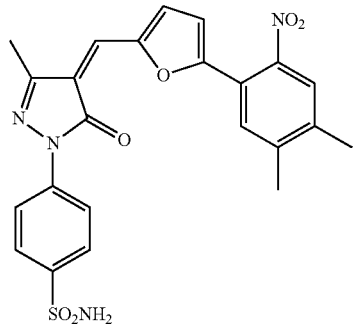 |
| 6i | 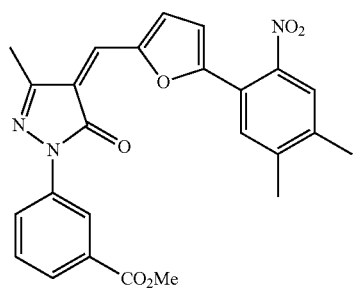 |
| 6j | 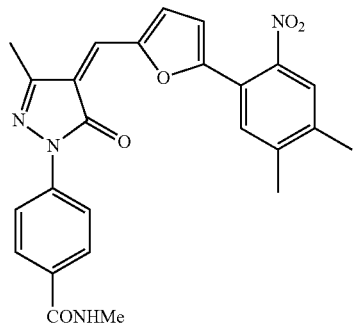 |
| 6l | 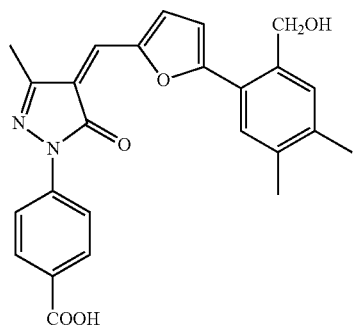 |

| Compound | Structure |
|---|---|
| 6m | 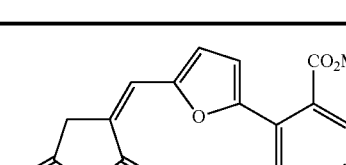 |
| 6n | 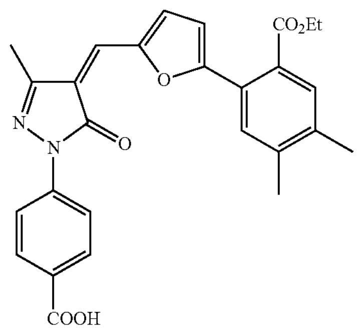 |
| 6o | 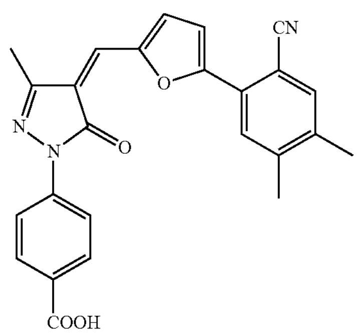 |
| 6q | 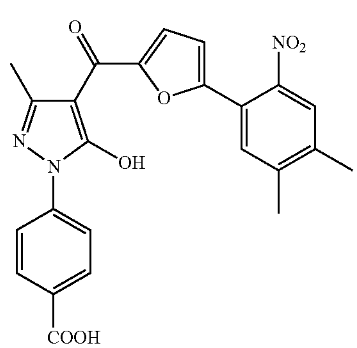 |

| Compound | Structure |
|---|---|
| 6r | | or a salt, solvate, or stereoisomer thereof.

18. The method of claim 17, wherein the subject was treated with radiation therapy or at least one additional anti-cancer agent.

19. The method of claim 18, wherein the anti-cancer agent is a DNA damaging chemotherapeutic agent.

20. The method of claim 19, wherein the DNA damaging chemotherapeutic agent is cisplatin or temozolamide.

21. A method for treating cancer in a subject, the method comprising administering an effective amount of a p300/CBP HAT inhibitor selected from the group consisting of a) a compound represented by Formula II:

(II)

in which
  X is H, C(O)-Q or S(O)$_2$-Q;
  Y is H, halogen, or C(O)-Q;
  $R_1$ and $R_2$ are independently H or $C_1$-$C_4$alkyl; and
  $R_3$ is halogen, C(O)-Q, $NO_2$, CN, or $CH_2OH$;
  Q is OH, O—$C_1$-$C_4$alkyl, —$NH_2$, or NH($C_1$-$C_4$alkyl);
  or a salt, solvate, or stereoisomer thereof, b) a compound represented by Formula III:
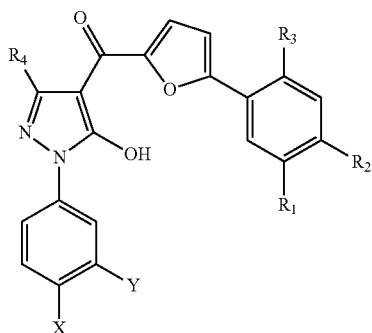
(III)
in which
X is H, C(O)-Q or S(O)$_2$-Q;
Y is H, halogen, or C(O)-Q;
$R_1$ and $R_2$ are independently H or $C_1$-$C_4$alkyl; and
$R_3$ is halogen, C(O)-Q, NO$_2$, CN, or CH$_2$OH;
$R_4$ is H or methyl;
Q is OH, O—$C_1$-$C_4$alkyl, —NH$_2$, or NH($C_1$-$C_4$alkyl);
or a salt, solvate or stereoisomer thereof; and
c) a compound selected from the following compounds:
| Compound | Structure |
|---|---|
| 6b | |
| 6g | |
| 6i | 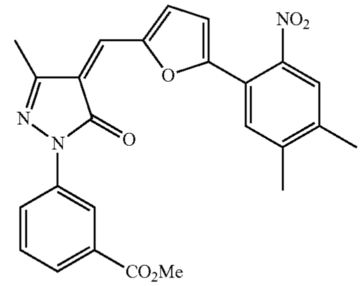 |
| 6j | 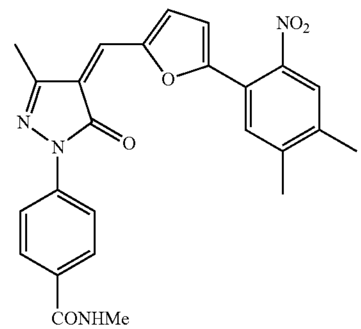 |
| 6l | 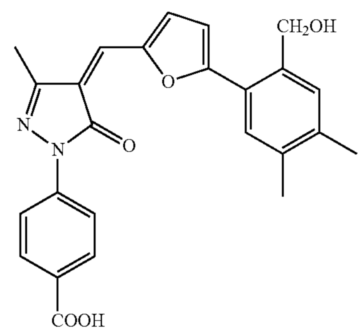 |
| 6m | 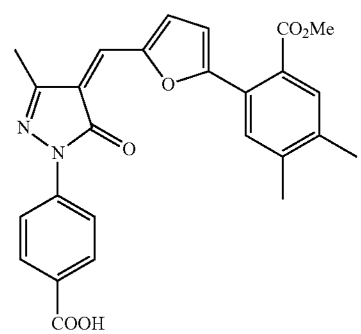 |
| 6n | 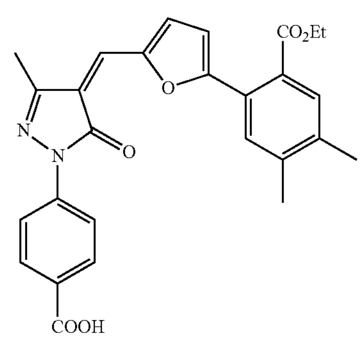 |

| Compound | Structure |
|---|---|
| 6o | 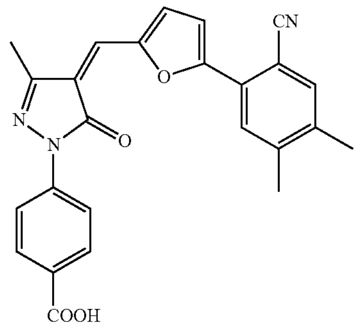 |
| 6q | 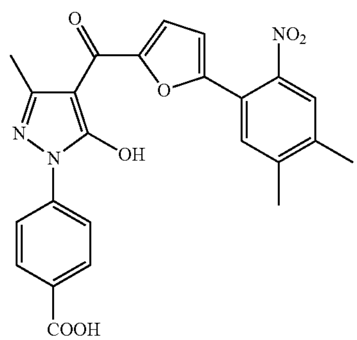 |

| Compound | Structure |
|---|---|
| 6r | 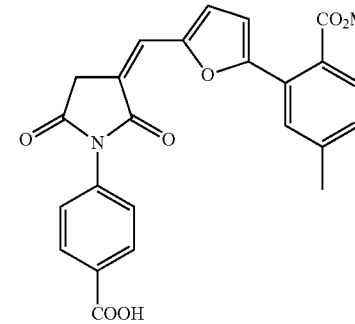 | or a salt, solvate, or stereoisomer thereof, in combination with radiation therapy or at least one additional anti-cancer agent to a subject in need thereof, wherein the cancer is leukemia, brain cancer, lung cancer, CNS cancer, melanoma, renal cancer, prostate cancer, colon cancer, ovarian cancer, or breast cancer.

22. The method of claim 21, wherein the anti-cancer agent is a DNA damaging chemotherapeutic agent.

23. The method of claim 22, wherein the DNA damaging chemotherapeutic agent is cisplatin or temozolamide.

* * * * *